United States Patent
Warner et al.

(10) Patent No.: US 6,853,472 B2
(45) Date of Patent: Feb. 8, 2005

(54) ELECTROLYTES FOR ELECTROOPTIC DEVICES COMPRISING IONIC LIQUIDS

(75) Inventors: Benjamin P. Warner, Los Alamos, NM (US); T. Mark McCleskey, Los Alamos, NM (US); Anoop Agrawal, Tucson, AZ (US); John P. Cronin, Tucson, AZ (US); Juan C. L. Tonazzi, Tucson, AZ (US); Anthony K. Burrell, Los Alamos, NM (US)

(73) Assignee: The Regents of the University of California, Los Alamos, NM (US)

(*) Notice: Subject to any disclaimer, the term of this patent is extended or adjusted under 35 U.S.C. 154(b) by 44 days.

(21) Appl. No.: 10/600,807

(22) Filed: Jun. 20, 2003

(65) Prior Publication Data

US 2004/0021928 A1 Feb. 5, 2004

Related U.S. Application Data

(60) Provisional application No. 60/390,611, filed on Jun. 21, 2002.

(51) Int. Cl.[7] .......................... G02F 1/153; G02F 1/15; H01B 1/00; C08F 4/06; H01M 6/18
(52) U.S. Cl. ........................ 359/270; 359/265; 359/275; 252/500; 252/600; 252/62.2; 526/120; 525/259; 429/307; 544/347; 546/257
(58) Field of Search ........................ 359/265, 267, 359/270, 275; 252/500, 583, 600, 62.2; 526/120, 122; 525/259; 429/307; 544/347; 546/257

(56) References Cited

U.S. PATENT DOCUMENTS

| | | | | |
|---|---|---|---|---|
| 3,451,741 A | * | 6/1969 | Manos | 359/275 |
| 3,453,038 A | * | 7/1969 | Kissa et al. | 359/275 |
| 3,637,611 A | * | 1/1972 | Takeya et al. | 526/120 |
| 3,651,019 A | * | 3/1972 | Asscher et al. | 525/259 |
| 4,671,619 A | | 6/1987 | Kamimori et al. | 350/357 |
| 4,902,108 A | | 2/1990 | Byker | 359/265 |
| 5,140,455 A | | 8/1992 | Varaprasad et al. | 359/275 |
| 5,729,379 A | | 3/1998 | Allemand et al. | 359/270 |
| 5,827,602 A | | 10/1998 | Koch et al. | 429/194 |
| 5,864,419 A | | 1/1999 | Lynam | 359/265 |
| 5,940,201 A | | 8/1999 | Ash et al. | 359/267 |
| 5,998,617 A | | 12/1999 | Srinvasa et al. | 544/347 |
| 6,045,724 A | | 4/2000 | Varaprasad et al. | 252/583 |
| 6,122,093 A | | 9/2000 | Lynam | 359/275 |

(List continued on next page.)

FOREIGN PATENT DOCUMENTS

| | | | | |
|---|---|---|---|---|
| JP | 08329479 | 6/1998 | | C07C/57/145 |
| JP | 0193363 | 12/2001 | | H01M/10/40 |
| WO | 0163350 | 8/2001 | | G02F/1/153 |

OTHER PUBLICATIONS

Rika Hagiwara and Yasuhiko Ito, "Room Temperature Ionic Liquids of Alkylimidazolium Cations and Fluoroanions," Journal of Fluorine Chemistry, vol. 105, pp. 221–227, 2000.
Charles M. Gordon, "New Developments in Catalysis Using Ionic Liquids," Applied Catalysis A: General, vol. 222, pp. 101–117, 2001.

(List continued on next page.)

*Primary Examiner*—Loha Ben
(74) *Attorney, Agent, or Firm*—Samuel L. Borkowsky

(57) ABSTRACT

Electrolyte solutions of soluble bifunctional redox dyes in molten salt solvent may be used to prepare electrooptic devices with enhanced stability toward ultraviolet radiation. The solvents include lithium or quaternary ammonium cations, and perfluorinated sulfonylimide anions selected from trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$).

23 Claims, 12 Drawing Sheets

U.S. PATENT DOCUMENTS

| | | | | |
|---|---|---|---|---|
| 6,141,137 | A | 10/2000 | Byker et al. | 359/265 |
| 6,172,794 | B1 | 1/2001 | Burdis | 359/269 |
| 6,178,034 | B1 | 1/2001 | Allemand et al. | 359/265 |
| 6,241,916 | B1 | 6/2001 | Claussen et al. | 252/583 |
| 6,245,262 | B1 | 6/2001 | Varaprasad et al. | 264/1.31 |
| 6,246,505 | B1 | 6/2001 | Teowee et al. | 359/241 |
| 6,266,177 | B1 | 7/2001 | Allemand et al. | 359/265 |
| 6,310,714 | B1 | 10/2001 | Lomprey et al. | 359/265 |
| 6,317,248 | B1 | 11/2001 | Agrawal et al. | 359/265 |
| 6,319,428 | B1 * | 11/2001 | Michot et al. | 252/500 |
| 6,327,070 | B1 | 12/2001 | Heuer et al. | 359/269 |
| 6,344,918 | B1 | 2/2002 | Berneth et al. | 359/275 |
| 6,362,914 | B2 | 3/2002 | Baumann et al. | 359/265 |
| 6,365,068 | B1 * | 4/2002 | Michot et al. | 252/500 |
| 6,365,301 | B1 | 4/2002 | Michot et al. | 429/307 |
| 6,372,159 | B1 | 4/2002 | Berneth et al. | 252/583 |
| 6,420,036 | B1 | 7/2002 | Varaprasad et al. | 428/432 |
| 6,519,072 | B2 | 2/2003 | Nishikitani et al. | 359/272 |
| 2002/0012155 | A1 | 1/2002 | Baumann et al. | |
| 2003/0030883 | A1 | 2/2003 | Giri et al. | |

OTHER PUBLICATIONS

Martyn J. Earle, Paul B. McCormac, and Kenneth R. Seddon, "Diels–Alder Reactions in Ionic Liquids," Green Chemistry, pp. 23–25, Feb. 1999.

J. Sun, M. Forsyth, and D. R. MacFarlane, "Room–Temperature Molten Salts Based on the Quaternary Ammonium Ion," J. Phys. Chem. B. vol. 102, pp. 8858–8865, 1998.

"Ultraviolet Stabilizers," Modern Plastics World Encyclopedia, pp. C–120–C–123, 2001.

Mark J. Muldoon, Andrew J. McClean, Charles M. Gordon, and Ian R. Dunkin, "Hydrogen Abstraction From Ionic Liquids by Benzophenone Triplet Excited States," Chem. Commun., pp. 2364–2365, 2001.

D. Behar, P. Neta, and Carl Schultheisz, "Reaction Kinetics in Ionic Liquids as Studied by Pulse Radiolysis: Redox Reactions in the Solvents Methyltributylammonium Bis(trifluoromethylsulfonyl)imide and N–Butylpyridinium Tetrafluoroborate," J. Phys. Chem. A, vol. 106, pp. 3139–3147, 2002.

Punam Giri, Leroy J. Kloeppner, K. L. Baumann, J. R. Lomprey, and Thomas F. Guarr, "Ultraviolet Stabilizing Materials Having a Solubilizing Moiety," U. S. Patent Application Publication 2003/0030883, published on Feb. 13, 2003.

A. W. Czanderna, D. K. Benson, G. J. Jorgensen, J.–G. Zhang, C. E. Tracy, and S. K. Deb, "Durability Issues and Service Lifetime Prediction of Electrochromic Windows for Buildings Applications," Solar Energy Materials & Solar Cells, vol. 56, pp. 419–436, 1999.

Dave Thieste, Harlan J. Byker, Kelvin Baumann, and Ramanujan Srinivasa, "Near Infrared–Absorbing Electrochromic Compounds and Devices Comprising the Same," PCT Application WO 99/45081, published Sep. 10, 1999.

Clemens Bechinger, Suzanne Ferrere, Arie Zaban, Julian Sprague, and Brian A. Greeg,"Photoelectrochromic Windows and Displays," Nature, vol. 383, pp. 608–610, Oct. 1996.

Mark Niemeyer, "σ–Donor Versus $\eta^6\pi$–Arene Interactions in Monomeric Europium(II) and Ytterbium(II) Thiolates— An Experimental and Computational Study," Eur. J. Inorg. Chem., pp. 1969–1981, 2001.

Kirk–Othmer Encyclopedia of Chemical Technology, $4^{th}$ edition, vol. 3, pp. 1016–1018, pp. 1107–1109; and vol. 15, pp. 446–447.

Alan B. McEwen et al., "Non–Flammable Electrolytes," WO 01/93363, published Dec. 6, 2001.

Watanabe Masayoshi et al., "Normal Temperature–Melting Salt and Electrochemical Device Using the Same," Japan 10–168028, issued Jun. 23, 1998.

Christophe Michot et al., "Materials Useful as Electrolytic Solutes," U.S. Appl. Ser. No. 6,365,301 issued Apr. 2, 2002.

Desarju V. Varaprasad et al., "Electrochromic Polymeric Solid Films, Manufacturing Electrochromic Devices Using Such Solid Films, and Processes for Making Such Solid Films and Devices," U.S. Appl. No. 6,420,036, issued Jul. 16, 2002.

Harlan J. Byker, "Single–Compartment, Self–Erasing, Solution–Phase Electrochromic Devices, Solutions for Use Therein and Uses Thereof," U.S. Pat. No. 4,902,108, issued Feb. 20, 1990.

Ramanujan Srinivasa et al., "Electrochromic Compounds," U.S. Pat. No. 5,998,617, issued Dec. 7, 1999.

Desaraju V. Varaprasad et al., "Large Area Electrochromic Window," U.S. Pat. No. 6,045,724, issued Apr. 4, 2000.

Desaraju V. Varaprasad et al., "Electrochromic Polymeric Solid Films, Manufacturing Electrochromic Devices Using Such Solid Films, and Processes for Making Such Films and Devices," U.S. Pat. No. 6,245,262, issued Jun. 12, 2001.

Kevin L. Ash et al., "Electrochromic Mirror with Two Thin Glass Elements and a Gelled Electrochromic Medium," U.S. Appl. No. 5,940,201, issued Aug. 17, 1999.

Niall R. Lynam, "Near–Infrared Reflecting, Safety Protected, Electrochromic Vehicular Glazing," U.S. Appl. No. 5,864,419, issued Jan. 26, 1999.

Niall R. Lynam, "Reduced Ultraviolet Radiation Transmitting, Safety Protected Electrochromic Glazing Assembly," U.S. Appl. No. 6,122,093, issued Sep. 19, 2000.

Kelvin L. Baumann et al., "Electrochromic Materials with Enhanced Ultraviolet Stability and Devices Comprising Same," U.S. Pat. No. 6,362,914, issued Mar. 26, 2002.

Jeffrey R. Lomprey et al., "Color–Stabilized Electrochromic Devices," U.S. Pat. No. 6,310,714, issued Oct. 30, 2001.

Desaraju V. Varaprasad et al., "High Performance Electrochemichromic Solutions and Devices Thereof," U.S. Pat. No. 5,140,455, issued Aug. 18, 1992.

Kelvin L. Baumann et al., "Electrochromic Materials with Enhanced Ultraviolet Stability and Devices Comprising Same," U. S. Patent Publication 2002/0012155, issued Jan. 31, 2002.

Horst Berneth et al., "Electrochromic Contrast–Plate," U.S. Pat. No. 6,344,918, issued Feb. 5, 2002.

Victor R. Koch et al., "Hydrophobic Ionic Liquids," U.S. Appl. No. 5,827,602, issued Oct. 27, 1998.

Anoop Agrawal et al., "Busbars for Electrically Powered Cells," U.S. Appl. No. 6,317,248, issued Nov. 13, 2001.

Jeffrey R. Lomprey, "Substituted Metallocenes for Use as Anodic Electrochromic Materials, and Electrochromic Media and Devices Comprising the Same," WO 01/63350, published Aug. 30, 2001.

Horst Berneth et al., "UV–Protected Electrochromic Solution," U.S. Pat. No. 6,372,159, issued Apr. 16, 2002.

Harlan J. Byker et al., "Electrochromic Media for Producing a Preselected Color," U.S. Pat. No. 6,141,137, issued Oct. 31, 2000.

Yoshinori Nishikitani et al., "Electrochromic Device," U.S. Pat. No. 6,519,072, issued Feb. 11, 2003.

Uwe Claussen et al., "Electrochromic System," U.S. Pat. No. 6,241,916, issued Jun. 5, 2001.

Dave Thieste et al., "Near Infrared–Absorbing Electrochromic Compounds and Devices Comprising the Same," WO 99/45081, published Sep. 10, 1999.

Tadatoshi Kamimori et al., "Electro–optic Device," U.S. Pat. No. 4,671,619, issued Jun. 9, 1987.

Pierre–Marc Allemand et al., "Electrochromic Devices," U.S. Pat. No. 5,729,379, issued Mar. 17, 1998.

Pierre–Marc Allemand et al., "Electrochromic Devices," U.S. Pat. No. 6,178,034, issued Jan. 23, 2001.

Pierre–Marc Allemand et al., "Electrochromic Devices," U.S. Pat. No. 6,266,177, issued Jul. 24, 2001.

Helmut–Werner Heuer et al., "Electrochromic Assembly Based on Poly(3,4–ethylenedioxythiophene) Derivatives in Combination With a Lithium Niobate Counterelectrode," U.S. Pat. No. 6,327,070, issued Dec. 4, 2001.

Mark Samuel Burdis, "Electrochromic Devices," U.S. Pat. No. 6,172,794, issued Jan. 9, 2001.

Gimtong Teowee et al., "Photochromic Devices," U.S. Pat. No. 6,246,505, issued Jun. 12, 2001.

* cited by examiner

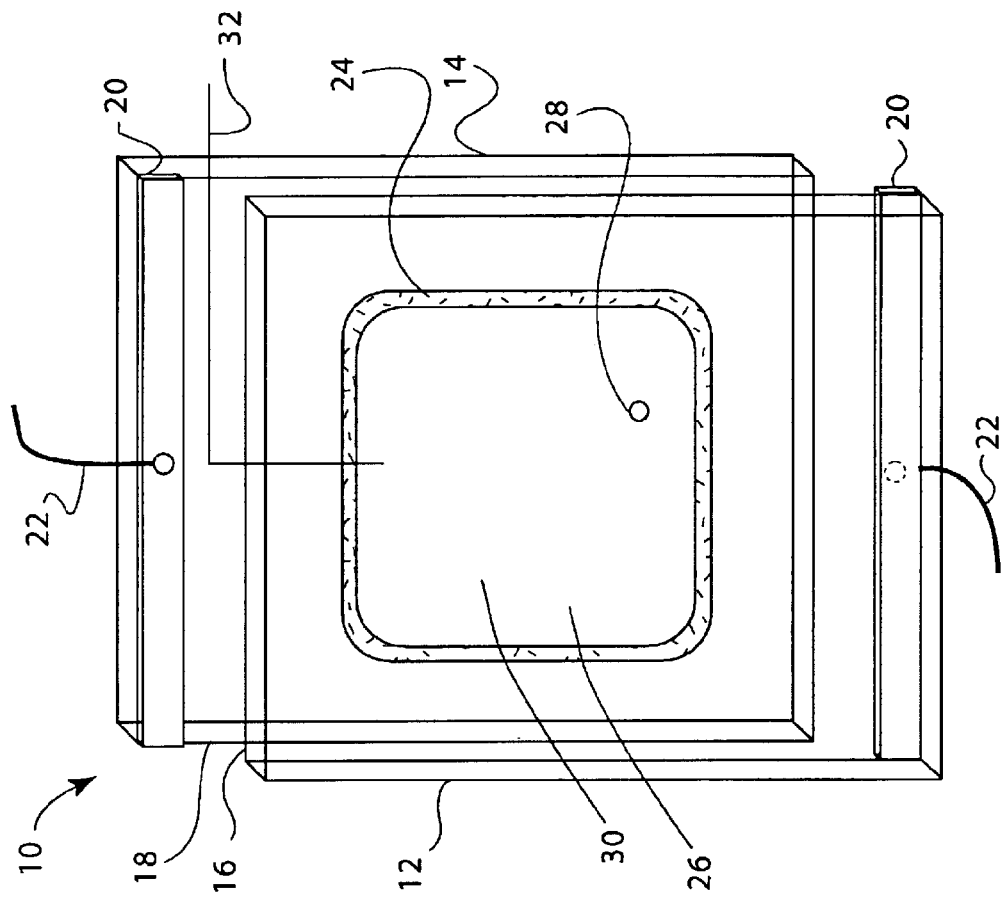
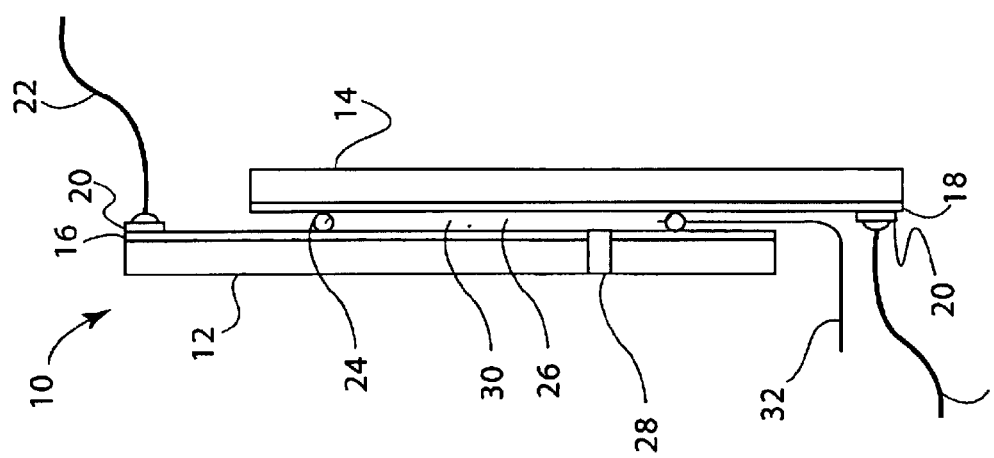

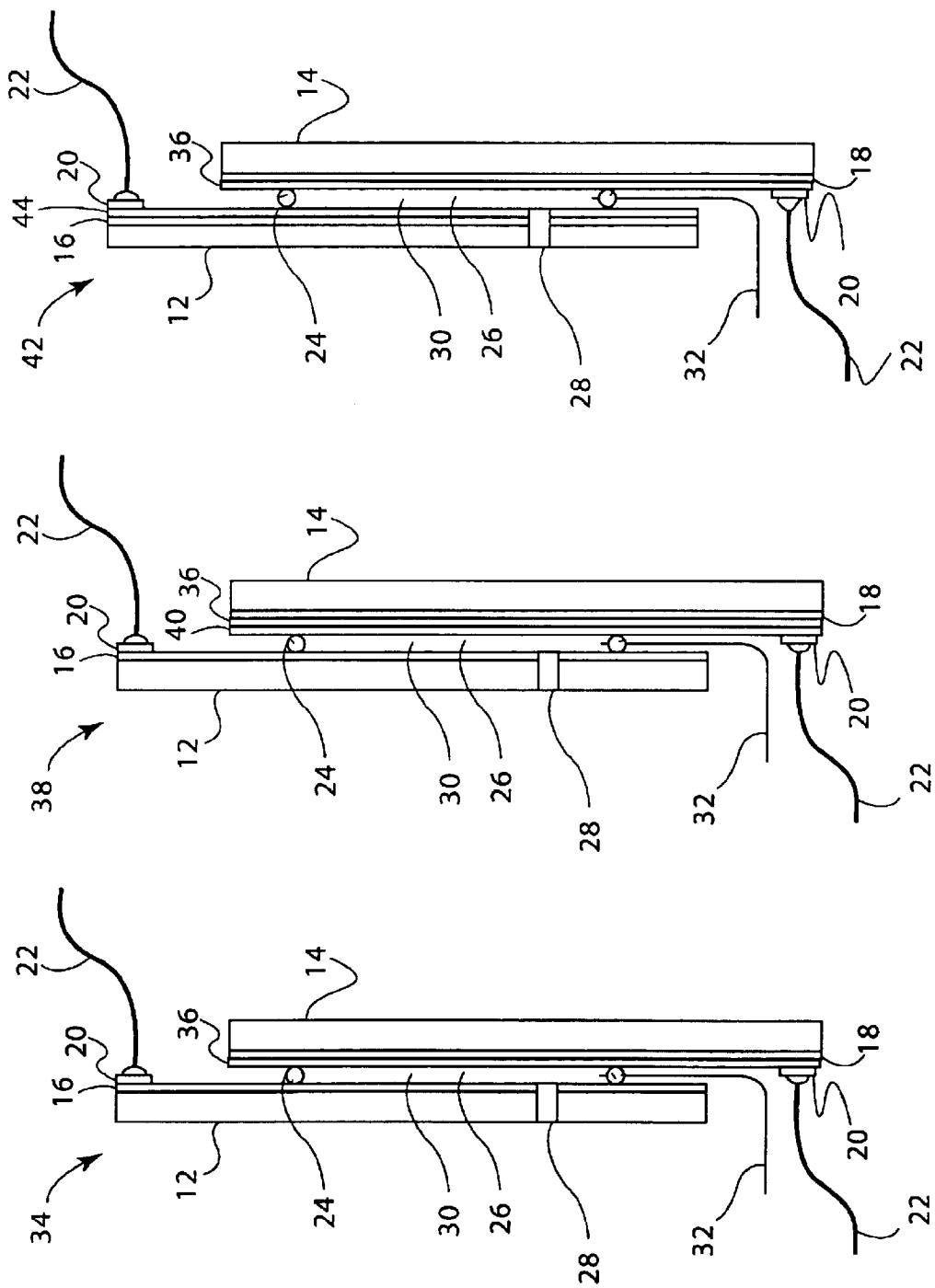

ELECTROLYTES FOR ELECTROOPTIC DEVICES COMPRISING IONIC LIQUIDS

RELATED APPICATIONS

This application claims the priority of U.S. Provisional Patent Application 60/390,611 entitled "Electrolytes for Electrooptic Devices Comprising Ionic Liquids," which was filed on Jun. 21, 2002, incorporated by reference herein.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to electrolyte solutions and electrooptic devices and more particularly to electrolyte solutions of UV stabilizing dyes in ionic liquid solvents and to electrooptic devices employing these solutions.

BACKGROUND OF THE INVENTION

Electrooptic devices are devices in which an applied electrical voltage produces a change in the optical properties of the device. Electrooptic devices are used for many applications such as variable transmission windows used for management of solar heat gain in buildings and variable transmission automotive mirrors. A specific type of an electrooptic device is an electrochromic device, i.e. a device that changes color in response to an applied voltage.

Electrochromic (EC) devices provide reversible modulation of light and are useful for several applications. Some of the applications are rearview mirrors for automobiles, trucks, buses, scooters and motorcycles; windows for automobiles, other transportation (including road, rail, water and air) and buildings, eyewear and attenuation or modulation of artificial lighting, displays, contrast enhancement filters (including variable transmission filters for helmet mounted displays). The only successful commercial application thus far has been for automotive rearview mirrors. High cost and lack of durability have limited commercial window applications of these EC devices.

The durability limitation of the EC devices arises in part due to the electrolytes and solvents used in the prior art. The typical high dielectric solvents used in present day devices may have one or more of the following drawbacks: high volatility, high moisture sensitivity, hydrophilicity, a narrow range of electrochemical stability, chemical reactivity, and susceptibility to light-induced degradation (typically from ultraviolet or UV light). One of the requirements of solvents for EC devices is that the other chemical components of the EC device are soluble and chemically stable with them.

Recent progress with ionic liquids has shown that certain problems associated with conventional solvents may be overcome by the use of a variety of ionic liquid solvents that are organic solvents that are composed of ammonium cations and trifluorosulfonyl-containing anions. In addition to overcoming the aforementioned problems, these solvents have a low flammability, thus making products incorporating them safer than products incorporating more conventional organic solvents.

A limitation of the use of ionic liquids for electrooptic devices is that many of the known components of electrochromic devices have limited solubility in ionic liquids. Furthermore, the intrinsic limitations, e.g. electrochemical stability, of known electrochromic dyes and additives, are matched to conventional organic solvents, and therefore these dyes and other additives do not allow the full exploitation of the advantageous properties of the ionic liquids. The use of ionic liquids is described, for example, in PCT Patent Application WO 01/93363 to A. McEwen et al. entitled "Non-Flammable Electrolytes," in Japanese Patent 98168028 to M. Watanabe et al. entitled "Room Temperature Molten Salts and Electrochemical Devices Using the Salts," and in U.S. Pat. No. 6,365,301 to C. Michot et al. entitled "Materials Useful as Electrolytic Solutes," which issued on Apr. 2, 2002, all of which are incorporated by reference herein. These papers and patents describe the use of ionic liquids for use in electrolytes, but fail to give specific details of electrolyte compositions and characteristics of the electrochromic devices made using ionic liquids.

There remains a need for electrooptic devices with greater durability.

Therefore, an object of the present invention is to provide an electrooptic device with greater durability.

Another object of the present invention is to provide electrolyte solutions for electrooptic devices.

Still another object of the invention is to provide soluble dye compounds for use with ionic liquids for electrooptic devices.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the objects and purposes of the present invention, as embodied and broadly described herein, the present invention includes an electrolyte solution having a Tg of less than about −40° C. that includes at least one bifunctional redox dye compound dissolved in an ionic liquid solvent. One type of redox dye compound useful with the invention includes a redox active anodic moiety and a redox active cathodic moiety. Another type of redox dye compound includes an energy receptor moiety and either a redox active anodic moiety or a redox active cathodic moiety. Preferred cations of the ionic liquid solvent include lithium cation and quaternary ammonium cations, where preferred quaternary ammonium cations are pyridinium, pyridazinium, pyrimidinium, pyrazinium, imidazolium, pyrazolium, thiazolium, oxazolium, triazolium, tetraalkylammonium, N-methyl morpholinium, cations of the formula $[(CH_3CH_2)_3N(R_1)]^+$, wherein $R_1$ is alkyl having 2–10 carbons, cations of the formula $[(CH_3)_2(CH_3CHCH_3)N(R_2)]^+$, wherein $R_2$ is alkyl having 2–10 carbons, cations having the structural formula

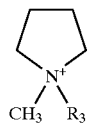

wherein $R_3$ is alkyl having 2–10 carbons, and cations having the structural formula

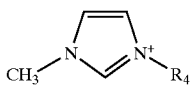

wherein $R_4$ is alkyl having 2–10 carbons, and preferred anions include trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

The invention also includes an electro-optic device having at least one chamber and, as the electrolyte medium inside the chamber, an electrolyte solution of a bifunctional redox dye compound dissolved in ionic liquid solvent and having a Tg of less than about −40° C. One type of redox dye compound useful with the invention includes a redox active anodic moiety and a redox active cathodic moiety. Another type of redox dye compound includes an energy receptor moiety and either a redox active anodic moiety or a redox active cathodic moiety. Preferred cations of the ionic liquid solvent include lithium cation and quaternary ammonium cations, where preferred quaternary ammonium cations include pyridinium, pyridazinium, pyrimidinium, pyrazinium, imidazolium, pyrazolium, thiazolium, oxazolium, triazolium, tetraalkylammonium, N-methyl morpholinium, cations of the formula [($CH_3CH_2)_3N(R_1)]^+$, wherein $R_1$ is alkyl having 2–10 carbons, cations of the formula [($CH_3)_2(CH_3CHCH_3)N(R_2)]^+$, wherein $R_2$ is alkyl having 2–10 carbons, cations having the structural formula

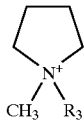

wherein $R_3$ is alkyl having 2–10 carbons, and cations having the structural formula

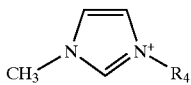

wherein $R_4$ is alkyl having 2–10 carbons, and preferred anions include trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

The invention also includes dye compounds for use with electrooptic devices.

The invention also includes a method for filling an empty electrooptic device with warm ionic liquid electrolyte solution, the device having relatively closely spaced plates, each plate having an inwardly facing conductive surface, the plates being sealed around their periphery by a seal that encloses an area of each plate. The method involves introducing a small opening into the seal of an empty device and placing the empty device into a chamber along with a container of an electrolyte solution that includes ionic liquid solvent. After evacuating the chamber, the empty device is lowered into the electrolyte solution such that the opening in the seal is located under the surface of the solution. At least a portion of the electrolyte solution is warmed to at least 40° C. Upon exposure of the solution to gas pressure greater than the pressure in the empty device, the warm electrolyte solution moves into the device. After filling the device with electrolyte solution, the gap is sealed.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings:

FIG. 1a shows a cutaway, edge-on view of an embodiment of an electrochromic device of the invention;

FIG. 1b shows a perspective view of the embodiment of the electrochromic device of FIG. 1a;

FIG. 2 shows a cutaway, edge-on view of an embodiment of an electrochromic device of the invention that includes an electrochemically active coating;

FIG. 3 shows a cutaway, edge-on view of an embodiment of an electrochromic device of the invention that includes an electrochemically active coating and an ion-selective transport layer;

FIG. 4 shows a cutaway, edge-on view of an embodiment of an electrochromic device of the invention that includes two electrochemically active coatings;

DETAILED DESCRIPTION OF THE INVENTION

Figure 5C:
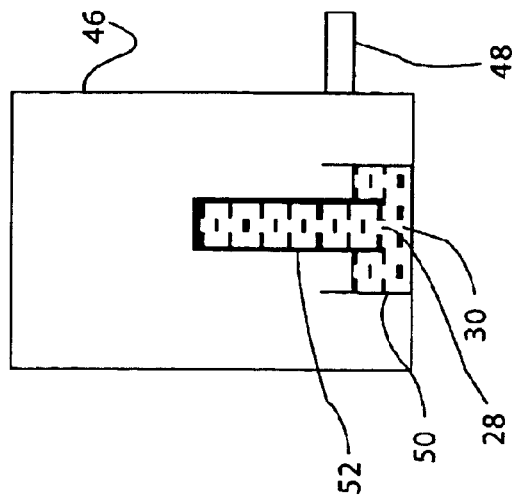
FIGS. 5a–c show a schematic representation for a vacuum-backfill process.

The invention relates to electrooptic devices that employ ionic liquids as electrolyte solvents. Ionic liquids are molten salts that have melting points at or below room temperature. For the purposes of the invention, the terms "ionic liquid" and "molten salt" have the same meaning. A non-exhaustive list of these materials is provided by R. Hagiwara and Y. Ito in "Room Temperature Ionic Liquids of Alkylimidazolium Cations and Fluoroanions", J. Fluorine Chem. vol. 105, (2000), pp. 221–227. Ionic liquid solvents of this invention do not include the mineral acids (such as sulfuric acid).

There are only a few papers and patents that suggest the use of ionic liquids in electrolytes (in PCT Patent Application WO 01/93363 to A. McEwen et al. entitled "Non- Flammable Electrolytes," in Japanese Patent 98168028 to M. Watanabe et al. entitled "Room Temperature Molten Salts and Electrochemical Devices Using the Salts," and in U.S. Pat. No. 6,365,301 to C. Michot et al. entitled "Materials Useful as Electrolytic Solutes," which issued on Apr. 2, 2002). These papers and patents do not provide specific details of electrolytic compositions for EC devices and also do not describe the characteristics of EC devices made from such liquids.

The present invention relates to electrolytes and other components and constructions of EC devices using ionic liquids as solvents. The present invention relates to employing ionic liquid solvents in display devices, where individual electrodes allow pictures, words, and other images to be created and controlled through EC behavior. Processing methods are disclosed for manufacturing electrooptic devices.

Careful choice of ionic liquid solvents can offer several benefits, which include a wider range for electrochemical stability (greater than 4V and in some cases greater than 6V); high hydrophobicity; a high decomposition temperature (ionic liquids used with the invention do not boil but they decompose, the decomposition temperatures should be higher than 150° C. and more preferably higher than 200° C.); a negligible vapor pressure (see, for example, C. M. Gordon in "New developments in catalysis using ionic liquids, Applied Catalysis: General A, vol. 222, (2001) pp. 101–117; and J. M. Earle in "Diels-Alder Reactions in Ionic Liquids," Green Chemistry, vol. 1 (1999) pp. 23–25); non-flammability (non-ignitable by a flame, see WO 01/93363); low UV susceptibility (for non-conjugated cations, no absorption peaks between 290 and 400 nm); and high conductivity.

Ionic liquid solvents useful with the invention include salts of organic cations in combination with either organic or inorganic anions. Preferred anions of the invention contain fluorine, and include trifluoromethylsulfonate ("triflate," $CF_3SO_3^-$), bis(trifluoromethylsulfonyl)imide ($N(CF_3SO_2)_2^-$), bis(perfluoroethylsulfonyl)imide ($(C_2F_5SO_2)_2N^-$)), tris(trifluoromethylsulfonyl)methide ($(CF_3SO_2)_3C^-$)), tetrafluoroborate ($BF_4^-$), hexafluorophosphate ($PF_6^-$), hexafluoroantimonate ($SbF_6^-$), and hexafluoroarsenate ($AsF_6^-$). Of these anions, trifluoromethylsulfonate ("triflate," $CF_3SO_3^-$), bis(trifluoromethylsulfonyl)imide ($N(CF_3SO_2)_2^-$), bis(perfluoroethylsulfonyl)imide ($(C_2F_5SO_2)_2N^-$)), tris(trifluoromethylsulfonyl)methide ($(CF_3SO_2)_3C^-$)) are preferred. The most preferred anion is bis(trifluoromethylsulfonyl)imide anion ($N(CF_3SO_2)_2^-$) because of its low cost and high hydrophobicity. The bis(trifluoromethylsulfonyl)imide anion is sometimes referred to in the prior art as bis(trifluoromethanesulfonyl)amide or bis(trifluoromethanesulfonyl)imide, and has the structural formula

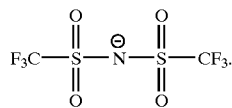

Preferred organic cations of molten salts used with the invention include, but are not limited to, pyridinium, pyridazinium, pyrimidinium, pyrazinium, imidazolium, pyrazolium, thiazolium, oxazolium, and triazolium. A preferred list of quaternary ammonium based ionic liquids are all those with a glass transition temperature ($T_g$) lower than −40° C. given in Table 1 of the publication by J. Sun, M. Forsyth, and D. R. MacFarlane entitled "Room-Temperature Molten Salts Based on the Quaternary Ammonium Ion," J. Phys. Chem. B, 1998, vol. 102, pages 8858–8864, and in U.S. Pat. No. 5,827,602 to V. R. Koch et al. entitled "Hydrophobic Ionic Liquids," which issued Oct. 27, 1998, both incorporated by reference herein.

Preferred ionic liquids include tetraalkylammonium cations because ionic liquids made from these cations have minimal optical absorbance in the ultraviolet portion of the spectrum, which gives molten salts based on these cations enhanced photochemical stability (see, J. Sun et al., vide supra). Quaternary ammonium cations useful with the invention may be substituted with H, F, phenyl, alkyl groups with 1 to 15 carbon atoms, and other chemical substituents. Cations may even have bridged ring structures.

Most preferred quaternary ammonium cations have the formula $(CH_3CH_2)_3N(R_1)$, wherein $R_1$ is alkyl having 2–10 carbons; or have the formula $(CH_3)_2(CH_3CHCH_3)N(R_2)$, wherein $R_2$ is alkyl having 2–10 carbons; or have the structural formula

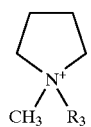

wherein $R_3$ is alkyl having 2–10 carbons; or have the structural formula

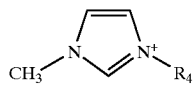

wherein $R_4$ is alkyl having 2–10 carbons.

Most preferably, the ionic liquid solvent is N-butyl-N-methylpyrrolidinium bis(trifluoromethylsulfonyl)imide.

Since EC devices can be used in a wide range of temperatures (e.g., automotive windows may be subjected from −40° C. to 95° C. or higher), the high electrochemical stability window assures that the even when the electrochemical potentials for reducing or oxidizing EC materials change with temperature, they will be within the stability window of the ionic liquid solvent. High hydrophobicity ensures that water does not become an integral part of the electrolyte and generate electrochemical reactions that are not reversible.

High boiling points and low vapor pressures of ionic liquids are useful properties from the electrooptic device fabrication perspective. Most of the EC devices are back-filled in vacuum (the vacuum backfill process is described in detail later). The low vapor pressure does not contaminate the vacuum systems, keeps the electrolyte composition constant and does not entrap bubbles in the filling process. This also enhances chemical safety in the work place. Low flammability is important from a safety perspective, particularly when used in buildings and in transportation.

Preferred ionic liquid solvents used with the present invention do not significantly absorb ultraviolet radiation having a wavelength above 290 nanometers (nm), and therefore do not degrade when exposed to these wavelengths to byproducts that can lead to irreversible coloration, gas formation and/or formation of electrochemically active/inactive species.

The preferred ionic liquid solvents are those that can result in formulations with a Tg below 0° C., preferably below −20° C. and most preferably below −40° C. As will be shown in EXAMPLE 8 (vide infra), Tg can be measured from viscosity data.

To make EC devices of practical use, several ingredients may be required in the electrolyte. Depending on device construction and its application, EC devices may require UV stabilizers, other co-solvents (propylene carbonate, methyl sulfolane, for example) and salts, redox dyes, viscosity modifiers, gelling materials, dyes that impart permanent colors, including those which absorb in the near infra-red region (wavelengths between 700 and 2500 nm) and opacifiers. Several types of EC devices, electrolyte solutions, and other constituents are described below. Some that include liquid or laminatable solid electrolytes are shown in FIGS. 1 to 4.

Reference will now be made in detail to the present preferred embodiments of the invention. Similar or identical structure is identified using identical callouts. FIG. 1a shows an edge-on view, and FIG. 1b shows a perspective view, of an embodiment of an electrochromic device of the invention. Devices of this configuration are referred to as single compartment devices in the art, because the electrochemical activity takes place in a single layer of material (i.e. the electrolyte) between the conductive electrodes. FIGS. 1a–b shows electrochromic device 10, which includes first substrate 12 and second substrate 14. It should be understood that the substrates are not limited to any particular shape or material, such as plastic, or glass, and that one electrode may be made of an opaque substrate such as metal or metal-coated plastic or metal-coated glass. Preferred metals include aluminum, silver, chromium, rhodium, stainless steel, and silver alloys in which the silver is alloyed with gold, palladium, platinum, or rhodium. Curved substrates, for example, may also be used. For convenience, small flat pieces of glass may be employed as substrates. Device 10 includes first conductive layer 16 on first substrate 12 and second conductive layer 18 on second substrate 14. Conductive layers are typically indium tin oxide, or fluorine-doped indium tin oxide, but any conductive coating, such as thin layers of metal or conducting polymers may be used. Conductive layer 18 is needed if second substrate 14 is not conductive, for example if second substrate 14 is made of glass or plastic. However, conductive layer 18 is optional if second substrate 14 already is conductive, for example if second substrate 14 is made of metal or metal-coated glass or metal coated plastic. When second substrate 14 is conductive, then second substrate 14 functions as both a structural substrate and a conductive layer. Electrochromic device 10 includes metallic bus bars 20, one attached to an end portion of first conductive layer 16 and another attached to an end portion of second conductive layer 18. If second substrate 14 is electrically conductive, then the bus bar 20 may be directly attached to second substrate 14. Wire 22 is soldered or otherwise attached to each bus bar 20 for connecting to a voltage source (a battery or the like, not shown).

Bus bars 20 are made from a suitable conductive metallic material and provide good electrical contact with the conductive layers or the substrate. Examples of bus bar materials include silver frits, solder alloys, metallic strips, wires and clips. Preferred materials include copper, copper alloys (such as copper-beryllium alloys), and tin plated copper.

Electrochromic device 10 includes electrically non-conductive gasket 24, which forms a seal with first conductive layer 16 and with second conductive layer 18 or with second substrate 14 if second conductive layer 18 is not used to provide chamber 26. Preferably, the width of chamber 26, which is the width between first conductive layer 16 and second conductive layer 18, is from about 20 microns to about 5000 microns. More preferably, the chamber width is from about 40 microns to about 500 microns.

Gasket 24 should be chemically stable to molten salt electrolyte used with the invention, substantially impermeable to water and the atmosphere (especially to oxygen and carbon dioxide), and robust over a wide temperature range, preferably from temperatures of about −40° C. to about 100° C. Gasket 24 provides electrical insulation between the two conducting surfaces so that substantially all electrical current passes through electrolyte solution 30. Typically, thickness of gasket 24 determines the distance between first conductive layer 16 (i.e. the working electrode) and second conductive layer 18 (i.e. the counter electrode), and affects the volume of chamber 26 and internal resistance of device 10.

Device 10 includes at least one port 28 for filling chamber 26 with solution 30 of molten salt. Port 28 may be located at any convenient location (through gasket 24, through first substrate 12, through second substrate 14, for example). Only one port is needed if vacuum-backfill techniques are used to fill chamber 26 with solution 30, but additional ports (for the purpose of, for example, pressure relief) may be present if different fill methods are used. After filling chamber 26, port(s) 28 are plugged.

Electrolyte solution 30 is non-volatile and hydrophobic, and provides high concentrations of cations and anions that offer minimal resistance to current. Solution 30 in chamber 26 remains in electrical contact with first conductive layer 16 and second conductive layer 18 (or with second substrate 14 if second conductive layer 18 is not used).

The bulk of electrolyte solution 30 is ionic liquid solvent. Solution 30 also includes at least one anodic and at least one cathodic material. The anodic material and cathodic material may each be a moiety of a single bifunctional redox compound. The anodic material and/or cathodic material may be ionic in order to improve their solubility in the ionic liquid solvent, and their associated anions are preferably identical to those of the ionic liquid solvent.

The cation of the molten salt solvent is preferably tetraalkylammonium, alkyl-substituted pyrrolidine, or alkyl-substituted imidazole. The anion of the molten salt is preferably perchlorate, tetrafluorborate, hexafluorophosphate, trifluoromethylsulfonate ($CF_3SO_3^-$), bis (trifluoromethylsulfonyl)imide (($CF_3SO_2)_2N^-$), bis (perfluoroethylsulfonyl)imide (($CF_3CF_2SO_2)_2N^-$) and tris (trifluoromethylsulfonyl)methide (($CF_3SO_2)_3C^-$).

Most preferably, the molten salt is N-butyl-N-methylpyrrolidinium bis(trifluoromethylsulfonyl)imide.

Solution 30 may optionally contain thixotropic agents, such as dispersed, electrochemically inert inorganic materials such as silica or alumina to facilitate injection into chamber 26.

Solution 30 may also contain one or more coloring agents to afford a desired color in either a darkened state or a bleached state.

The bifunctional dyes used with the invention provide stabilization toward ultraviolet radiation. Solution 30 may contain additional soluble ultraviolet (UV) stabilizers (see, for example: Modern Plastics World Encyclopedia (2001) p-C-120 to C-122, Chemical Week Publishing, NY, incorporated by reference herein).

Solution 30 may also contain one or more stiffening agents to increase the viscosity of solution 30 while maintaining conductivity. This is desirable in order to minimize the spread of solution 30 if device 10 is damaged. Stiffening agents include, but are not limited to, organic monomers and polymers such as poly(acrylonitrile), poly(vinylidene fluoride), poly(hexafluoropropylene), poly(vinylalcohol), poly(vinylacetate), poly(methylmethacrylate) and their copolymers. These polymers may be formed in situ. They may be crosslinked in situ by polymerization of monomers (see, for example, U.S. Pat. No. 6,420,036 to D. V. Varaprasad et al. entitled "Electrochromic Polymeric Solid Films, Manufacturing Electrochromic Devices Using Such Solid Films, and Processes for Making Such Solid Films and Devices," which issued Jul. 16, 2002, incorporated by reference herein). Poly(methylmethylacrylate) (PMMA), for example, may be formed by adding methyl methylacrylate to the molten salt and then adding benzoyl peroxide to initiate the polymerization.

Solution 30 optionally includes one or more soluble co-solvents that decrease the viscosity of solution 30 and do not interfere with the durability and function of the reversible mirror. Preferably, co-solvents are aprotic and have high boiling points (preferably above 150° C.), low melting points (preferably below −30° C.), and are present in concentrations from about 0.5% to about 30%. Preferable co-solvents include propylene carbonate, N-methyl pyrrolidinone, perfluorodecalin, and perfluorodecane.

Optionally, device 10 may include pseudo-reference electrode 32 for evaluating the electric potential of conductive layer 16. Pseudo-reference electrode 32 may be in the form of a silver wire inserted through gasket 24 such that pseudo reference electrode 32 does not contact conductive layer 16 or conductive layer 18. Pseudo-reference electrodes may take other forms. A minor portion of first conductive layer 16 or second conductive layer 18, for example, may be separated away by etching a separation line to provide a pseudo-reference electrode.

The invention may be used with a standard, glass, multiple-pane window by substituting one or more panes of the multiple-pane window with an electrooptic device of the invention. The glass panes may be coated with low-emissivity materials that block/attenuate UV, infrared, and/or visible light.

There are many patents that describe EC devices. Some that describe EC devices utilizing non-ionic liquid electrolytes include U.S. Pat. No. 4,902,108 to H. J. Byker entitled "Single Compartment, Self-Erasing, Solution Phase Electrochromic Devices, Solutions for Use Therein, and Uses Thereof," which issued Feb. 20, 1990; U.S. Pat. No. 5,998,617 to S. Ramanujan et al. entitled "Electrochromic Compounds," which issued Dec. 7, 1999; and U.S. Pat. No. 6,045,724 to D. V. Varaprasad et al. entitled "Large Area Electrochromic Window," which issued Apr. 4, 2000, all incorporated by reference herein. Others that describe EC devices that utilize solid electrolytes include U.S. Pat. No. 6,245,262 to D. V. Varaprasad et al. entitled "Electrochromic Polymeric Solid Films, Manufacturing Electrochromic Devices Using Such Solid Films, and Processes for Making Such Films and Devices," which issued on Jun. 12, 2001, and U.S. Pat. No. 5,940,201 to K. L. Ash et al. entitled "Electrochromic Mirror With Two Thin Glass Elements and a Gelled Electrochromic Medium," which issued on Aug. 17, 1999, all incorporated by reference herein. Generally, plasticising the polymers with the liquid electrolytes produces solid electrolytes. The solvents described in these patents are neutral polar materials such as nitrites (e.g., glutaronitrile, 3-hydroxypropionitrile), sulfolanes (e.g., 3-methylsulfolane), ethers (e.g., polyethylene oxide, polypropyleneoxide and tetraglyme), alcohols (ethoxyethanol, ethanol), ketones and esters (e.g., gamma-butyrolactone, propylene carbonate, ethylene carbonate), and mixtures of these. While a more detailed list of the solvents and other components is described in these patents, none disclose the use of ionic liquids.

The UV stability of reported electrooptic devices has been improved with UV filters and additives (see, for example U.S. Pat. No. 5,864,419 to N. R. Lynam entitled "Near-Infrared Reflecting, Ultraviolet Protected, Safety Protected, Electrochromic Vehicular Glazing," which issued on Jan. 26, 1999; U.S. Pat. No. 6,122,093 to N. R. Lynam entitled "Reduced Ultraviolet Radiation Transmitting, Safety Protected Electrochromic Glazing Assembly," which issued on Sep. 19, 2000; U.S. Pat. No. 6,362,914 to K. L. Baumann et al. entitled "Electrochromic Materials With Enhanced Ultraviolet Stability and Devices Comprising the Same," which issued on Mar. 26, 2002; and U.S. Pat. No. 6,310,714 to J. R. Lomprey et al. entitled "Color-Stabilized Electrochromic Devices," which issued on Oct. 30, 2001). In U.S. Pat. 5,140,155 to D. V. Varaprasad et al. entitled "High Performance Electrochemichromic Solutions and Devices Thereof," which issued on Aug. 18, 1992, the choice of solvents is made based on UV absorption properties of the solvent. The most cost effective method is to add a UV stabilizer to the electrolyte.

While the ionic liquids used with the invention are UV stable materials, EC devices of the invention that include these materials may still require additional stabilizers for the protection of the other ingredients such as polymers and dyes, and also to reduce any interaction of electrode/electrolyte promoted by light. For the purposes of the present invention, UV stabilizers include materials that absorb UV (ultraviolet) radiation, and materials that quench species generated by the UV to minimize damage caused by UV radiation. Any UV stabilizer or any of the other ingredients, including dyes must be soluble in the electrolyte within the temperature ranges in which the device is used. Since most applications are for mirrors, windows and devices that are subjected to the weathering elements, UV stabilizers must be compatible over a wide temperature range. A preferred minimum temperature range for devices to operate is from 0° C. to 50° C., a more preferred range is from −20° C. to 70° C., and a most preferred range is from −40° C. to 105° C. A non-exhaustive list of UV stabilizers can be found in Modem Plastics Encyclopedia, pages C120 to C122, 2001, Chemical Week Associates publication, New York, incorporated by reference herein. Some of the preferred UV stabilizers are benzophenone and derivatives thereof because these materials are compatible with several ionic liquids (see M. Muldoon et al. in "Hydrogen abstraction from ionic liquids by benzophenone triplet excited states," Chem. Commun., (2001) p. 2364–2365; D. Behar et.al. in "Reaction Kinetics in Ionic liquids as Studied by Pulse Radiolysis: Redox Reactions in the Solvents methyltributylammonium bis(trifluromethylsulfonyl)imide and n-butylpyridinium tetrafluoroborate," J. Phys. Chem. A., (2002), vol. 106, p. 3139–3147). Other preferred UV stabilizers are benzotriazoles (and derivatives thereof) and triazines (and derivatives thereof). The addition of UV stabilizers can also assist in decreasing the freezing point of the electrolytes, as they may constitute 0.01% to 40% of the weight of the molten salt solution.

UV stabilizers typically result in an average absorbance greater than 1 between the wavelengths of 290 and 400 nm (90% of attenuation of UV) and more preferably in an absorbance greater than 2 (99% attenuation of UV), as measured with a path length of one centimeter and a concentration of about 1% by weight of the UV stabilizer in the ionic liquid. This absorbance is measured by subtracting the absorbance of the ionic liquid without the UV stabilizer from the absorbance of the solution that contains the UV stabilizer.

In U.S. Patent Application Publication 2002/0012155 to K. L. Baumann et al. entitled "Electrochromic Materials With Enhanced Ultraviolet Stability and Devices Comprising the Same," which was published on Jan. 31, 2002, and in U.S. Pat. No. 6,344,918 to H. Berneth entitled "Electrochromic Contrast Plate," which issued on Feb. 5, 2002, both incorporated by reference herein, compounds are described that include a redox active dye moiety bridged to an energy receptor moiety (i.e. a UV stabilizer moiety) so that the same molecule is able to absorb UV and also function as a redox dye. For the purposes of the present invention, this is a type of compound is referred to herein more generally as a "bifunctional redox dye".

An advantage of using these bifunctional redox dyes (having tethered UV stabilizer moieties) is that the UV stability of the entire device is increased.

Additional examples of bifunctional redox dyes having a dye moiety attached to a UV stabilizer moiety are described in U.S. Pat. No. 6,362,914 to K. Baumann et al., entitled "Electrochromic Materials with Enhanced Ultraviolet Stability and Devices Comprising the Same," which issued Mar. 26, 2002, incorporated by reference herein. The '914 patent describes a cathodic compound prepared by attachment of a viologen dye to an UV stabilizer moiety, which is referred to in the '914 patent as an "energy receptor site". Typically, UV stabilizer moieties include benzophenones or benzotriazoles, which can be covalently attached to either an anodic or cathodic dye moiety. The UV stabilizer moiety of the compound absorbs the UV radiation and prevents damage to the dye moiety. A specific example of such a compound described in the '914 patent is 1-methyl-1-[1-benzotriazole-2-hydroxy-3-t-butyl-5-propyl(propionate)-[benzene]]-4,4-bipyridinium bis(tetrafluoroborate). For use in an ionic liquid electrooptic device of the present invention, a different compound is employed, one in which at least one tetrafluoroborate and preferably both tetrafluoroborate anions are replaced with trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) or tris(trifluoromethylsulfonyl)methide (($CF_3SO_2)_3C^-$), most preferably with bis(trifluoromethylsulfonyl)imide (($CF_3SO_2)_2N^-$). A compound containing bis(trifluoromethylsulfonyl)imide, for example, may be prepared by anion exchange of the corresponding tetrafluoroborate anion-based compound with bis(trifluoromethylsulfonyl)imide anion. Alternatively, this type of compound may be synthesized by the electrochemical oxidation of the anodic moiety (e.g. a phenazine moiety) in an ionic liquid comprising a bis(trifluoromethylsulfonyl)imide anion, or by the electrochemical reduction and re-oxidation of the cationic moiety (e.g. a viologen moiety) in the same ionic liquid.

Examples of cathodic moieties of bifunctional redox dyes of the present invention include those defined by the following structural formulae:

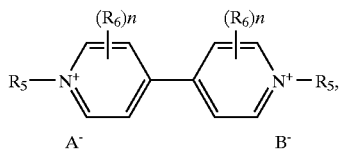

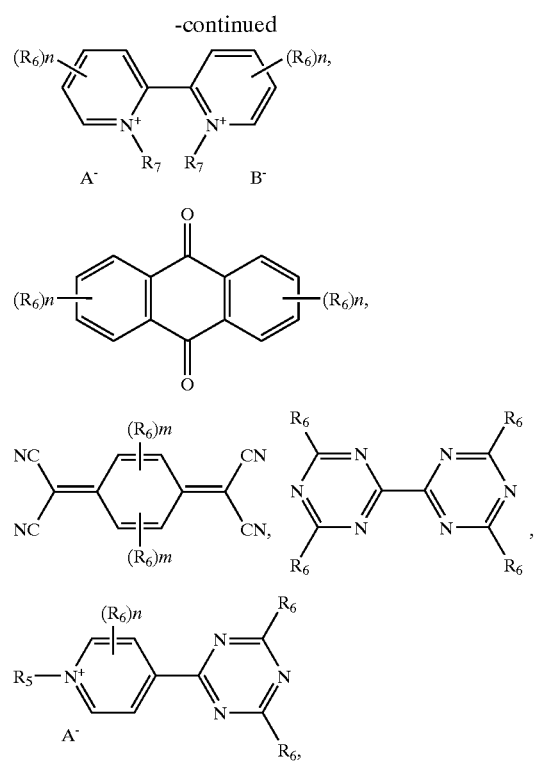

wherein $R_5$ is independently selected from alkyl $C_1$ to $C_{20}$, alkynyl $C_2$ to $C_{20}$, and aryl $C_5$ to $C_{20}$. $R_5$ may optionally contain one or more of an ester, carboxylic acid, metal carboxylate, ether, aryl, amine, urethane, ammonium, thioester, alkene, and alkyne functional group, and additionally may function as a bridge to an energy receptor moiety. $R_6$ is independently selected from hydrogen, alkyl $C_1$ to $C_{10}$, alkynyl $C_2$ to $C_{10}$, aryl $C_5$ to $C_{20}$, and may optionally contain one or more of an ester, carboxylic acid, metal carboxylate, ether, aryl, amine, urethane, ammonium, thioester, alkene, and alkyne functional groups, and additionally may function as a bridge to an energy receptor moiety. $R_7$ is independently selected from alkyl $C_1$ to $C_5$ or an ethyl, propyl or ethylene bridge; n=0–4; m=0–2. Anion $A^-$ is a trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) or tris(trifluoromethylsulfonyl)methide (($CF_3SO_2)_3C^-$) anion, and anion $B^-$ is a halogen anion, $ClO_4^-$, $BF_4^-$, $PF_6^-$, $AsF_6^-$, $SbF_6^-$, $CH_3COO^-$, $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) or tris(trifluoromethylsulfonyl)methide (($CF_3SO_2)_3C^-$) anion. Energy receptor moieties include those having the following chemical structures:

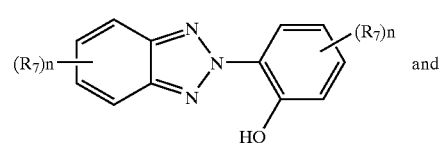

and

-continued

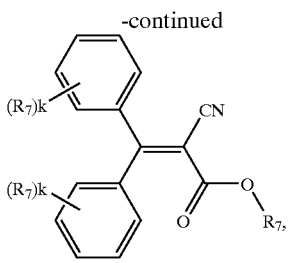

wherein $R_7$ is independently selected from alkyl $C_1$ to $C_{20}$, alkynyl $C_2$ to $C_{20}$, and aryl $C_5$ to $C_{20}$, and may optionally contain one or more of an ester, carboxylic acid, metal carboxylate, ether, aryl, amine, urethane, ammonium, thioester, alkene, and alkyne functional group, and additionally may function as a bridge to the energy receptor moiety. In these formulas, n=0–4 and k=0–5. Any of the above cathodic moieties when suitably bridged to any of the energy receptor moieties forms a bifunctional redox dye, and all of these compounds are examples of bifunctional redox dyes of the invention.

Examples of anodic moieties of bifunctional redox dyes of the present invention include those defined by the following structural formulae:

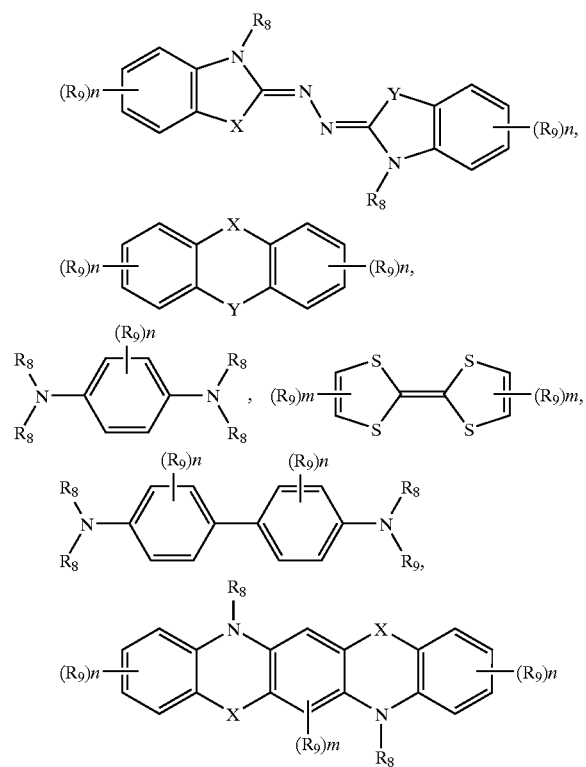

wherein X and Y are independently selected from NH, $NR_8$, S, and O. $R_8$ is independently selected from alkyl $C_1$ to $C_{20}$, alkynyl $C_2$ to $C_{20}$, and aryl $C_5$ to $C_{20}$ and may optionally contain one or more of an ester, carboxylic acid, metal carboxylate, ether, aryl, amine, urethane, ammonium, thioester, alkene, and alkyne functional group, etc, and additionally may function as a bridge to an energy receptor moiety. $R_9$ is independently selected from alkyl $C_1$ to $C_{10}$, alkyl $C_2$ to $C_{10}$, aryl $C_5$ to $C_{20}$, and may optionally contain one or more of an ester, carboxylic acid, metal carboxylate, ether, aryl, amine, urethane, ammonium, thioester, alkene, and alkyne functional group, and additionally may function as a bridge to an energy receptor moiety, and n=0–4, and m=0–2. The energy receptor moiety is one having the structure

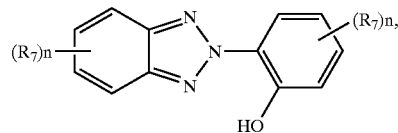

or having the structure

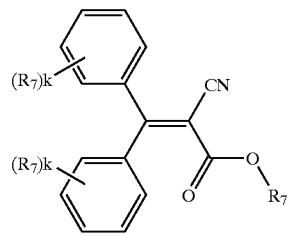

wherein $R_7$ is independently selected from alkyl $C_1$ to $C_{20}$, alkynyl $C_2$ to $C_{20}$, and aryl $C_5$ to $C_{20}$ and may optionally contain one or more of an ester, carboxylic acid, metal carboxylate, ether, aryl, amine, urethane, ammonium, thioester, alkene, and alkyne functional group, and additionally may function as a bridge to the energy receptor moiety, n=0–4, and k=0–5. These compounds, which have both an anodic dye moiety and an energy receptor moiety in the same molecule are also examples of bifunctional redox dyes of the invention, and when they are oxidized in ionic liquid solvent, a radical cation is formed that is charge counterbalanced with the anion of the ionic liquid solvent.

An important aspect of the invention is that the bifunctional redox dyes of the invention are soluble in the preferred ionic liquid solvents of the invention in their oxidized, reduced and any intermediate states. These dyes are reduced and/or oxidized in the device when the voltage is applied. This oxidation or reduction is reversible. Furthermore, one or more of the oxidized or reduced species should be different in color as compared to its earlier state (before application of the voltage). It should be understood that these species are also redox dyes. The dyes reduced at the cathode are cathodic dyes and the dyes oxidized at the anode are anodic dyes. In an invention device of the type shown in FIG. 1, several of these may be present, but at least one cathodic or one anodic dye should be present in the electrolyte. A bifunctional redox dye may include in a single molecule, both an anodic moiety and a cathodic moiety, and this type of dye may undergo both oxidation and reduction at the two electrodes.

Preferred cathodic moieties of the bifunctional dyes of the invention include viologens, which are cationic. Preferred viologens are N,N'-diethylviologen ("ethyl viologen"), N,N'-dimethylviologen ("methyl viologen") and N,N'-dibenzylviologen ("benzyl viologen") associated with fluorine containing anions such as $BF_4^-$, $PF_6^-$, $AsF_6^-$, $SbF_6^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). Preferred anions are trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

Preferred anodic moieties of the bifunctional dyes of the present invention include metallocenes (particularly ferrocenes), phenazines, phenothiazines, fulvalenes, and substutited 1,4- or 1,2-phenylenediamines, including their derivatives and combinations. Some preferred phenazines are 5,10-dihydro-5,10-dimethylphenazine; 5,10-dihydro-5,10-diethylphenazine; 5,10-dihydro-5,10-dioctylphenazine or any other 5,10-dihydro-5,10-dialkyphenazine. Preferred phenylenediamines include TMPD (N,N,N',N'-tetramethylphenyldiamine) and TMBZ (N,N,N',N'-tetramethylbenzydine). A preferred fulvalene is tetrathiafulvalene. For a listing of ferrocene derivatives useful with the invention, see U.S. Pat. No. 6,317,248 to A. Agrawal entitled "Busbars for Electrochemically Powered Cells," which issued on Nov. 13, 2001, and PCT application WO 01/63350 to J. R. Lomprey entitled "Substituted Metallocenes for use as Anodic Electrochromic Materials, and Electrochromic Media and Devices Comprising the Same," both incorporated by reference herein. Preferred ferrocenes of the invention include electron-donating groups that are attached to one or both of the cyclopentadiene rings, such as tertiary-butylferrocene and decamethylferrocene. Some of these anodic dyes may have to be fluorinated to increase their solubility in specific ionic solvents. Typically, the concentration of any of the dyes (cathodic and anodic) is less than 0.1 molar, preferably less than 0.05 molar.

At least one of the cathodic or anodic moieties of the bifunctional redox dye must be electrochromic in the reduced or the oxidized state with an absorption in the visible region of the electromagnetic radiation. As the dye moiety reversibly goes back to its non-activated form, the absorption should also reverse, meaning either shift or decrease to its earlier state.

Two or more separate dye compounds are often used with electrochromic devices to control the device properties such as the color of the device, the kinetics, etc. (see, for example, U.S. Pat. No. 6,141,137 to H. J. Byker et al. entitled "Electrochromic Media for Producing a Preselected Color," which issued on Oct. 31, 2000, incorporated by reference herein. Electrochemical considerations for choosing dyes are given in U.S. Pat. No. 4,902,108 (vide supra). Bifunctional redox dyes having an anodic moiety and a cathodic moiety in the same molecule have recently been reported. Examples of these types of compounds can be found in U.S. Pat. No. 6,372,159 to H. Berneth et al. entitled "UV-Protected Electrochromic Solution," which issued on Apr. 16, 2002, in U.S. Pat. No. 6,519,072 Y. to Nishikitani et al., entitled "Electrochromic Device," which issued Feb. 11, 2003, and in U.S. Pat. 6,241,916 to U. Claussen et al., entitled "Electrochromic system," which issued Jun. 5, 2001, and PCT application WO 01/163350 to Lomprey et al. (vide supra), all incorporated by reference herein. The U.S. Pat. Nos. 6,519,072 and 6,241,916 describe dyes where the anodic and the cathodic dyes are not separate molecules, but instead, each is present as either an anodic moiety or a cathodic moiety, and connected in the same molecule. The cyclic voltammogram of such a molecule displays at least one reduction peak and at least one oxidation peak that are derived from the compound when measured from the resting state (i.e. when there is no applied electrochemical potential). Either the reduction or oxidation process, and preferably both the reduction and oxidation processes, are accompanied by an increase in the molar extinction coefficient at at least one wavelength in the visible range.

The present invention includes bifunctional redox dyes that include a cathodic moiety covalently bridged to an anodic moiety. These compounds often have good UV stability. An example of such a UV stable dye is produced when a ferrocene moiety is coupled with a viologen moiety using an appropriate linker or bridge, and it was shown that a material of this type provides both anodic and cathodic redox in the electrolytes for electrochromic devices using conventional non-ionic solvents.

Bifunctional redox dyes having anodic and the cathodic moieties may be bridged with energy receptor moiety display to increase their UV stability even more. These types of dyes, when used with ionic liquid solvents according to the present invention are expected to provide electrooptic devices that would be most suitable for outside environment use, both in colored and bleached states. Some modifications to the UV stabilizers for use in conventional non-ionic solvents are given as an example in U.S. Patent Application Publication 2003/0030883 to P. Giri et al. entitled "Ultraviolet Stabilizing Materials Having a Solubilizing Moiety," which was published on Feb. 13, 2003.

The present invention includes bifunctional compounds having both anodic and cathodic moieties, wherein one or more are cationic moieties in the resting state, oxidized state, or reduced state, and are charge balanced by trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$), and preferably by bis(trifluoromethylsulfonyl)imide (($CF_3SO_2$)$_2N^-$). These compounds may be synthesized by anion exchange, for example, by reacting the salts described in U.S. Pat. No. 6,519,072 (vide supra) with lithium bis(trifluoromethylsulfonyl)imide ($Li(CF_3SO_2)_2N^-$) in water. Alternatively, compounds in which some of the cationic charges are balanced with bis(trifluoromethylsulfonyl)imide anions may be synthesized by the electrochemical oxidation of the anodic moiety (e.g. a ferrocene moiety) in an ionic liquid solvent comprising a bis(trifluoromethylsulfonyl)imide anion. Compounds in which some of the cationic charges are balanced with bis(trifluoromethylsulfonyl)imide anions may also be synthesized by the electrochemical reduction and re-oxidation of the cationic moiety (e.g. a viologen moiety) in an ionic liquid comprising a bis(trifluoromethylsulfonyl)imide anion. The present invention also includes the use of these compounds in an electrooptic device.

Preferably, the cathodic moiety of bifunctional dyes of the invention includes viologens (which have a bipyridinium ion-pair structures) or anthraquinones, while the anodic moiety has a pyrazoline, metallocene, phenylenediamine, benzidine, phenazine, phenoxadine, phenothiazine, or tetrathiafulvalene structure, or is a metal salt that can be oxidized in the ionic liquid solvent.

Electrochromic compounds in which the anodic and cathodic moieties are present in the same molecule, and including at least one anion that is the same as the anion of the ionic liquid solvent, preferably viologens with a bipyridinium ion-pair structure represented by the structural formula

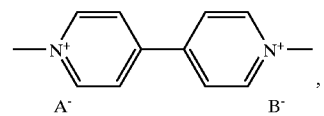

which exhibits cathodic electrochromic characteristics, and a metallocene structure represented by formulae

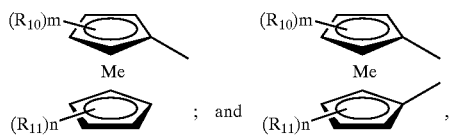

which exhibits anodic electrochromic characteristics. For these compounds, $A^-$ is selected from trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$), and $B^-$ is selected from halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). $R_{10}$ and $R_{11}$ are each independently a hydrocarbon group selected from alkyl, alkenyl and aryl groups having 1 to 10 carbon atoms, in the case where $R_{10}$ or $R_{11}$ is an aryl group, the aryl group may form a condensed ring together with a cyclopentadienyl ring. Also, m=0–4, n=0–4, and Me represents Cr, Co, Fe, Mn, Ni, Os, Ru, V, Mo(X)(Q), Nb(X)(Q), Ti(X)(Q), V(X)(Q) or Zr(X)(Q) wherein X and Q are each independently selected from hydrogen, halogen, an alkyl group having 1 to 12 carbon atoms, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). Examples of the alkyl group are methyl, ethyl, i-propyl, n-propyl, n-butyl, t-butyl, n-pentyl, n-hexyl, and cyclohexyl groups. The aryl group is exemplified by the phenyl group. Particularly preferred are methyl, ethyl, and propyl groups. In the case where $R_{10}$ or $R_{11}$ is an aryl group, the aryl group may form a condensed ring by bonding to a cyclopentadienyl ring and $R_{10}$ or $R_{11}$ may be a group cross-linking two cyclopentadienyl rings in the metallocene structure. Both m and n are preferably 0 or 1, and particularly preferably 0. Me is preferably Fe.

Preferred electrochromic compounds in which the anodic and cathodic moieties are present in the same molecule, and including at least one cationic moiety, are metallocene-bipyridine derivatives represented by the following formulae:

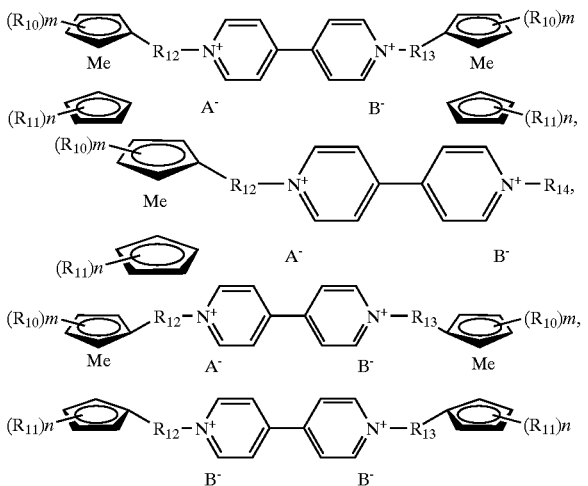

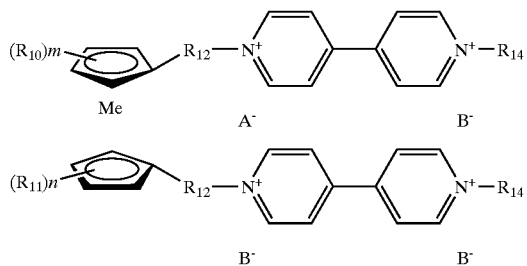

wherein $A^-$ is selected from trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$), and $B^-$ is selected from halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). $R_{10}$ and $R_{11}$ are each independently a hydrocarbon group selected from an alkyl group, alkenyl and aryl group having 1 to 10 carbon atoms, in the case where $R_{10}$ or $R_{11}$ is an aryl group, the aryl group may form a condensed ring together with a cyclopentadienyl ring. Also, m=0–4 and n=0–4. $R_{12}$ and $R_{13}$ are each independently a hydrocarbon residue having 1 to 20, preferably 1 to 10 carbon atoms, and $R_{14}$ is a hydrocarbon group selected from the group consisting of an alkyl, cycloalkyl, alkenyl, aryl, or aralkyl group having 1 to 20, preferably 1 to 10 carbon atoms, a heterocyclic group having 4 to 20, preferably 4 to 10 carbon atoms, and a substituted hydrocarbon or heterocyclic group obtained by substituting part of hydrogens of the hydrocarbon group or heterocyclic group with a substituent group. Me represents Cr, Co, Fe, Mn, Ni, Os, Ru, V, Mo(X)(Q), Nb(X)(Q), Ti(X)(Q), V(X)(Q) or Zr(X)(Q) wherein X and Q are each independently selected from hydrogen, halogen, an alkyl group having 1 to 12 carbon atoms, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). Examples of the hydrocarbon residue for $R_{12}$ and $R_{13}$ are hydrocarbon groups such as alkylene groups and various divalent groups having an ester-bond unit, ether-bond unit, amide-bond unit, thioether-bond unit, amine-bond unit, urethane-bond unit, or silyl unit in the part of hydrocarbon groups. The divalent group having an ester-bond unit may be exemplified by those represented by the formula —R—COO—R— or —R—OCO—R— wherein R is an alkylene group having 1 to 8 carbon atoms. Specific examples of the ester-bond unit are —$C_4H_8$—COO—$C_2H_4$—, —$C_4H_8$—OCO—$C_2H_4$—, —$C_4H_8$—COO—$C_4H_8$—, and —$C_4H_8$—OCO—$C_4H_8$—. The divalent group having an ether-bond unit may be exemplified by those represented by the formula —R—O—R— wherein R is an alkylene group having 1 to 10 carbon atoms. Specific examples of the ether-bond unit are —$C_4H_8$—O—$C_2H_4$— and —$C_4H_8$—O—$C_4H_8$—. The divalent group having an amide-bond unit may be exemplified by those represented by the formula —R—CONH—R— or —R—NHCO—R— wherein R is an alkylene group having 1 to 8 carbon atoms. Specific examples of the amide-bond unit are —$C_4H_8$—CONH—$C_2H_4$—, —$C_4H_8$—NHCO—$C_2H_4$—, —$C_4H_8$—CONH—$C_4H_8$—, and —$C_4H_8$—NHCO—$C_4H_8$—. The divalent group having a thioether-bond unit may be those represented by the formula —R—S—R— wherein R is an alkylene group having 1 to 10 carbon atoms. Specific examples of the thioether-bond unit are —$C_4H_8$—S—$C_2H_4$— and —$C_4H_8$—S—$C_4H_8$—. The divalent group having an amine-bond unit may be exemplified by those represented by the formula —R—NH—R— wherein R is an alkylene group having 1 to 10 carbon atoms and the formula —R—NH-Ph- wherein R is an alkylene group having 1 to 10 carbon atoms and Ph is an arylene group or a substituted arylene group having 1 to 12 carbon atoms. Specific examples of the amine-bond unit are —$C_4H_8$—NH—$C_2H_4$— and —$C_4H_8$—NH—$C_4H_8$—. The divalent group having a urethane-bond unit may be exemplified by those represented by the formula —R—OCONH—R— or —R—NHCOO—R— wherein R is an alkylene group having 1 to 8 carbon atoms. Specific examples of the urethane-bond unit are —$C_4H_8$—OCONH—$C_2H_4$—, —$C_4H_8$—NHCOO—$C_4H_8$—, —$C_4H_8$—OCONH—$C_4H_8$—, and —$C_4H_8$—NHCOO—$C_4H_8$—. The divalent groups having a silyl-bond unit may be represented by those represented by the formula —R—Si(R')$_2$—R— wherein R is an alkylene group having 1 to 8 carbon atoms and R' is methyl or ethyl. Specific examples of the silyl-bond unit are —$C_4H_8$—Si($CH_3$)$_2$—$C_2H_4$—, —$C_4H_8$—Si($CH_3$)$_2$—$C_4H_8$—, —$C_4H_8$—Si($C_2H_5$)$_2$—$C_2H_4$—, and —$C_4H_8$—Si($C_2H_5$)$_2$—$C_4H_8$—. Examples of the alkyl group for $R_{14}$ are methyl, ethyl, i-propyl, n-propyl, n-butyl, t-butyl, n-pentyl, n-hexyl, and n-heptyl groups. An example of the cycloalkyl group is cyclohexyl. Examples of the aryl group are phenyl, tolyl, xylyl, and naphthyl. Examples of the alkenyl group are vinyl and allyl groups. Examples of the aralkyl group are benzyl and phenylpropyl groups. Examples of the heterocyclic aromatic group are 2-pyridyl, 4-pyridyl, 2-pyrimidyl, and isoquinoline groups.

In the case where $R_{14}$ is a substituted hydrocarbon residue or heterocyclic group, examples of the substituent are alkoxy, alkoxycarbonyl, and acyl group having 1 to 10, preferably 1 to 5 carbon atoms, halogen, and cyano (—CN group), hydroxyl, nitro, and amino groups. Examples of the alkoxy group are methoxy and ethoxy groups. The alkoxycarbonyl group is exemplified by methoxycarbonyl. The acyl group is exemplified by acetyl. Examples of the halogen group are Cl and F. Examples of the substituted hydrocarbon residue are methoxyphenyl, chlorophenyl, fluorophenyl, methoxychlorophenyl, cyanophenyl, acetylphenyl, methoxycarbonylphenyl, and methoxynapthyl groups.

These metallocene-bipyridine bifunctional redox dyes of the invention may be synthesized by first synthesizing a precursor as described in U.S. Pat. No. 6,519,072 (vide supra) and then exchanging some or all of the anions by, for example, suspending or dissolving the precursor in water and combining it with an excess of lithium bis(trifluoromethylsulfonyl)imide. A precipitate forms, is collected, and then recrystallized to obtain the purified ferrocene-bipyridine bis(trifluoromethylsulfonyl)imide.

U.S. Pat. No. 6,241,916 to U. Claussen et al. (vide supra) describes bifunctional redox dyes having a covalent bridge that separates an anodic moiety from a cathodic moiety. Many of these dyes include anions such as tetrafluoroborate, perchlorate, methanesulfonate, trifluoromethanesulfonate, perfluorobutanesulfonate, benzenesulfonate, hexafluorophosphate, hexafluoroarsenate and hexafluorosilicate ($SiF_6^{2-}$), perfluorinated main group compounds, sulfonates, and perchlorate, but none include sulfonamides or perfluorosulfonimides. By contrast, bifunctional dyes of the present invention include at least one anion selected from bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$). Preferably, all of the anions are bis(trifluoromethylsulfonyl)imide (($CF_3SO_2$)$_2N^-$), bis(perfluoroethylsulfonyl)imide (($CF_3CF_2SO_2$)$_2N^-$) or tris(trifluoromethylsulfonyl)methide (($CF_3SO_2$)$_3C^-$). And more preferably, all of the anions are bis(trifluoromethylsulfonyl)imide (($CF_3SO_2$)$_2N^-$). The present invention also includes the radical cations of these dyes with these same anions.

The electrochromic system according to the invention also include bifunctional dyes having the formula

$Cat_1$-$An_1$, or having the formula

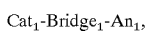

$Cat_1$-$Bridge_1$-$An_1$, or having the formula

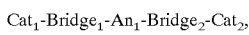

$Cat_1$-$Bridge_1$-$An_1$-$Bridge_2$-$Cat_2$, or having the formula

$An_2$-$Bridge_2$-$Cat_1$-$Bridge_1$-$An_1$, in which $Cat_1$ and $Cat_2$ independently represent cathodic moieties, and $An_1$ and $An_2$ independently represent anodic moieties. $Bridge_1$ and $Bridge_2$ independently represent a bridge member. These bifunctional redox dyes include at least one anion selected from bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$). The present invention also includes the radical cations of these dyes having these anions. Preferably, $Cat_1$ and $Cat_2$ independently represent the following structural formulae:

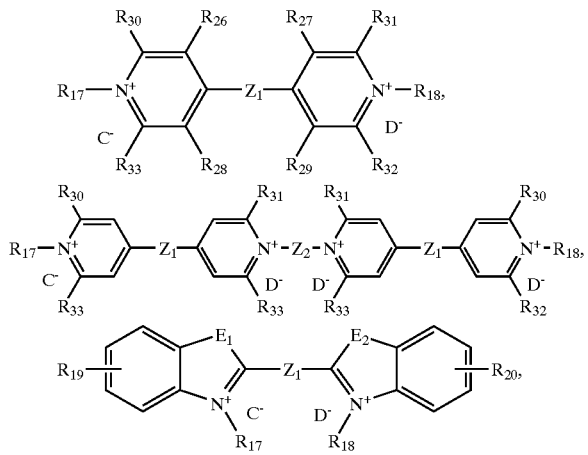

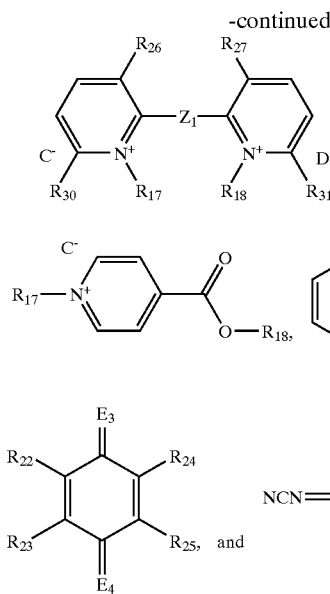

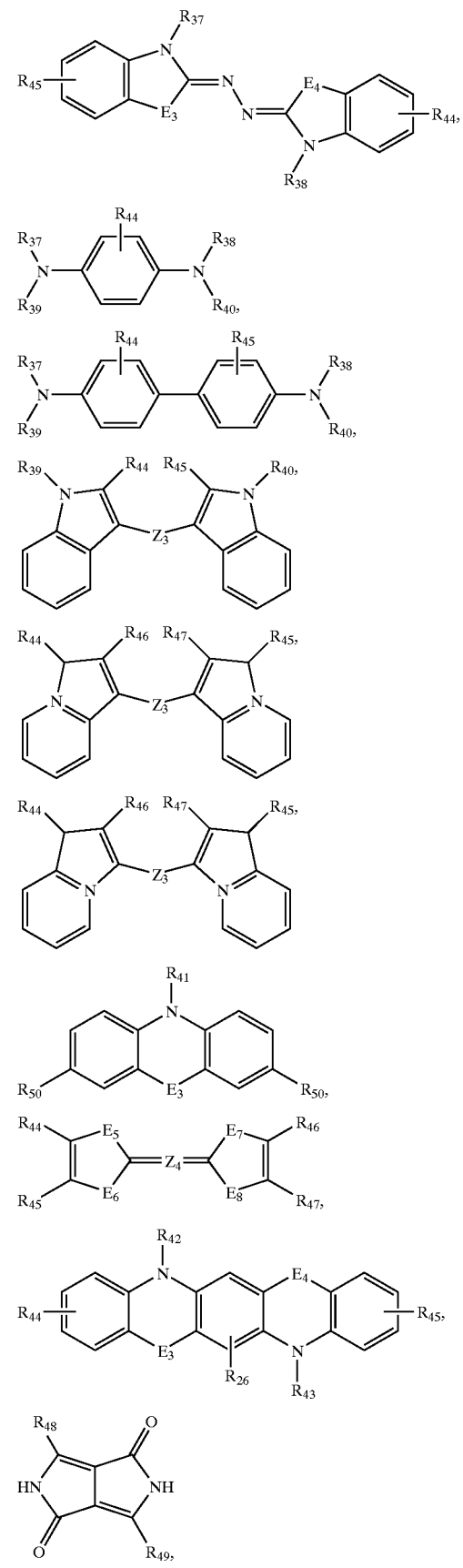

in which $R_{17}$ and $R_{18}$ independently of one another denote $C_1$ to $C_{18}$ alkyl, $C_2$ to $C_{12}$ alkenyl, $C_3$ to $C_7$ cycloalkyl, $C_7$ to $C_{15}$ aralkyl or $C_6$ to $C_{10}$ aryl or $R_{17}$ and $R_{18}$ together form a —(CH$_2$)$_2$—, —(CH$_2$)$_3$—, or —CH═CH— bridge, $R_{19}$, $R_{20}$ and $R_{22}$ to $R_{25}$ independently of one another denote hydrogen, $C_1$ to $C_{18}$ alkyl, $C_1$ to $C_{18}$ alkoxy, halogen, cyano, nitro or $C_1$ to $C_{18}$ alkoxycarbonyl or $R_{22}$ and $R_{23}$ and/or $R_{24}$ and $R_{25}$ form a —CH═CH—CH═CH— bridge. $R_{26}$, $R_{27}$, $R_{28}$ and $R_{29}$ independently of one another denote hydrogen or, in pairs, a —(CH$_2$)$_2$—, —(CH$_2$)$_3$— or —CH═CH— bridge, $E_3$ and $E_4$ independently of one another denote O, N—CN, C(CN)$_2$ or N—C$_6$ to C$_{10}$ aryl, $R_{34}$ and $R_{35}$ independently denote hydrogen, $C_1$ to $C_{18}$ alkyl, $C_1$ to $C_{18}$ alkoxy, halogen, cyano, nitro, $C_1$ to $C_{18}$ alkoxycarbonyl or $C_6$ to $C_{10}$ aryl. $R_{30}$ to $R_{33}$ independently of one another denote hydrogen or $C_1$ to $C_6$ alkyl, or $R_{30}$ and $R_{26}$ and/or $R_{31}$ and $R_{27}$ form a —CH═CH—CH═CH— bridge. $E_1$ and $E_2$ independently of one another denote O, S, NR$_{36}$ or C(R$_{36}$)$_2$ or $E_1$ and $E_2$ together form a —N—(CH$_2$)$_2$—N— bridge, $R_{36}$ denotes $C_1$ to $C_{18}$ alkyl, $C_2$ to $C_{12}$ alkenyl, $C_4$ to $C_7$ cycloalkyl, $C_7$ to $C_{15}$ aralkyl or $C_6$ to $C_{10}$ aryl. $Z_1$ denotes a direct bond, —CH═CH—, —C(CH$_3$)═CH—, —C(CN)═CH—, —CCl═CCl—, —C(OH)═CH—, —CCl═CH—, —C≡C—, —CH═N—N═CH—, —C(CH$_3$)═N—N═C(CH$_3$)— or —CCl═N—N═CCl—. $Z_2$ denotes —(CH$_2$)$_r$— or —CH$_2$—C$_6$H$_4$—CH$_2$—, where r=1–10. C$^-$ is selected from bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), and D$^-$ is selected from halogen anion, ClO$_4^-$, BF$_4^-$, PF$_6^-$, AsF$_6^-$, SbF$_6^-$, CH$_3$COO$^-$, CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), wherein bonding to the bridge member Bridge$_1$ or Bridge$_2$ is effected via one of the radicals $R_{17}$–$R_{36}$, and the radicals mentioned then represent a direct bond.

An$_1$ and An2 independently represent one of the following structural formulae:

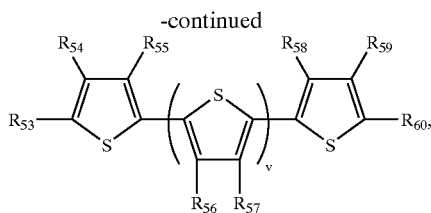

or $An_1$ or $An_2$ independently represent metal salts that include titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II). $R_{37}$ to $R_{43}$ independently of one another denote $C_1$ to $C_{18}$ alkyl, $C_2$ to $C_{12}$ alkenyl, $C_3$ to $C_7$ cycloalkyl, $C_7$ to $C_{15}$ aralkyl or $C_6$ to $C_{10}$ aryl, and $R_{41}$ to $R_{43}$ additionally denote hydrogen, $R_{44}$ to $R_{50}$ independently of one another denote hydrogen, $C_1$ to $C_{18}$ alkyl, $C_1$ to $C_{18}$ alkoxy, halogen, cyano, nitro, $C_1$ to $C_{18}$ alkoxycarbonyl or $C_6$ to $C_{10}$ aryl and $R_{48}$ and $R_{49}$ additionally denote an optionally benzo-fused aromatic or quasiaromatic five- or six-membered heterocyclic ring and $R_{50}$ additionally denotes $N(R_{51})(R_{52})$. $R_{44}$ and $R_{45}$ and/or $R_{46}$ and $R_{47}$ form a —$(CH_2)_3$—, —$(CH_2)_4$—, —$(CH_2)_5$— or —CH=CH—CH=CH— bridge. $Z_3$ denotes a direct bond or a —CH=CH— or —N=N— bridge, =$Z_4$=denotes a direct double bond or a =CH—CH= or =N—N= bridge. $E_3$ to $E_4$, $E_{10}$ and $E_{11}$ independently of one another denote O, S, $NR_{51}$, $C(R_{51})_2$, C=O or $SO_2$. $E_5$ to $E_8$ independently of one another denote S, Se or $NR_{51}$, $R_5$, and $R_{52}$ independently of one another denote $C_1$ to $C_{12}$ alkyl, $C_2$ to $C_8$ alkenyl, $C_3$ to $C_7$ cycloalkyl, $C_7$ to $C_{15}$ aralkyl or $C_6$ to $C_{10}$ aryl. $R_{53}$ to $R_{60}$ independently of one another denote hydrogen, $C_1$ to $C_6$ alkyl, $C_1$ to $C_4$ alkoxy, cyano, $C_1$ to $C_4$ alkoxycarbonyl or $C_6$ to $C_{10}$ aryl, or $R_{53}$ and $R_{54}$ and $R_{59}$ and $R_{60}$ independently of one another together form a —$(CH_2)_3$—, —$(CH_2)_4$— or —CH=CH—CH=CH— bridge, v=0–10, and bonding to the bridge member $Bridge_1$ or $Bridge_2$ is effected by one of the radicals $R_{37}$–$R_{54}$, $R_{59}$, or $R_{60}$ and the radicals mentioned then represent a direct bond, and $Bridge_1$ or $Bridge_2$ independently represents a bridge member of the formula —$(CH_2)_n$— or —$(Y_1)_s$—$(CH_2)_m$—$(Y_2)_o$—$(CH_2)_p$—$(Y_3)_q$—, each of which is optionally substituted by $C_1$ to $C_4$ alkoxy, halogen or phenyl. $Y_1$ to $Y_3$ independently of one another represents O, S, $NR_{61}$, COO, CONH, NHCONH, cyclopentanediyl, cyclohexanediyl, phenylene, naphthylene, or beta-dicarbonyl. $R_{61}$ denotes $C_1$ to $C_6$ alkyl, $C_2$ to $C_6$ alkenyl, $C_4$ to $C_7$ cycloalkyl, $C_7$ to $C_{15}$ aralkyl or $C_6$ to $C_{10}$ aryl, n=0–12, m=0–b 8, p=0–12, o=0–6, q=0–1, and s=0–1.

It should also be understood that the invention also includes the corresponding radical anions of the aforementioned cathodic compounds, the radical anions being generated in situ during electrochemical reduction, and for charge balance, necessarily include ammonium cations of the type present in the ionic liquid solvent.

Electrochromic compounds of the invention also include bifunctional redox dyes having a redox active cathodic moiety that provides the dye with its color properties, and a redox active metal species such as titanium (III), titanium (IV), vanadium (III), vanadium (IV), vanadium (V), iron (II), iron (III), cobalt (II), cobalt (III), copper (I), copper (II), silver (I), silver (II), indium (I), indium (III), tin (II), tin (IV), antimony (III), antimony (V), bismuth (III), bismuth (V), cerium (III), cerium (IV), samarium (II), samarium (III), dysprosium (II), dysprosium (III), ytterbium (II), ytterbium (III), europium (II), europium (III). A specific example of such a material, which includes a bipyridinium ion pair structure and Eu, was prepared (see EXAMPLE 12, vide infra).

EC devices of the present invention may also be prepared from electrolyte solutions of ionic liquid solvents, redox active cathodic dyes (viologens, for example) and a redox active metal in which the dye and metal form a bifunctional dye in the form of a metal-arene complex (metal-arene complexes are described in, for example, M. Niemeyer, "Sigma-Donor versus $\eta^6$—Arene Interactions in Monomeric Europium(II) and Ytterbium(II) Thiolates: An Experimental and Computational Study," Eur. J. Inorg. Chem. (2001), pp. 1969–1981).

Bifunctional redox dyes of the present invention that are in the form of metal-arene complexes have the formula $$[Cat_1][M]$$

where M is a metal salt that includes a metal such as titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II). An example of this type of bifunctional dye was prepared (see EXAMPLE 11, vide infra).

Another class of redox dyes used with the invention is the class of charge transfer compounds. Charge transfer compounds, sometimes referred to as charge transfer complexes, include at least one electron rich aromatic compound and at least one electron deficient aromatic compound; the electron rich compound and electron deficient compound combine in ionic liquid solvent to form the charge transfer compound. The UV-VIS spectrum of the charge transfer compound is not a simple linear combination of the spectra of the electron rich compound and electron deficient constituents (see FIG. 13), and have other properties such as enhanced solubility. The spectrum of the green, charge transfer compound formed by combining 5,10-dihydro-5,10-dimethylphenazine (a white compound) with diethyl viologen bis[bis(trifluoromethylsulfonyl)imide] (another white compound) in a 1:1 ratio includes absorption bands different from any present in the absorption spectra for either 5,10-dihydro-5,10-dimethylphenazine or N,N'-diethylviologen bis[bis(trifluoromethylsulfonyl)imide].

The present invention also includes electrooptic devices employing electrolyte solutions of charge transfer compounds and dissolved in ionic liquids. The present invention also includes charge transfer compounds having anions that are redox-inert colorless anions, where at least one anion is chosen from bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). Preferably at least one anion is bis(trifluoromethylsulfonyl)imide (($CF_3SO_2)_2N^-$). More preferably all of the anions are identical and chosen from bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$). Most preferably, the only anion is bis(trifluoromethylsulfonyl)imide (($CF_3SO_2)_2N^-$).

There are several other additives employed to change specific properties of the electrolyte solution of the invention. One of these is a viscosity modifier. Viscosity modifiers can be soluble polymers and fillers such as fumed silica, fine alumina, etc. Additives also include co-solvents, such as other ionic and non-ionic liquids. Some of these are used to change their physical properties of the electrolyte solution, such as the melting point. Additives may also change electronic properties (speed of response, current/time characteristics) of the electrolyte, and thus of electrooptic devices of the invention employing the electrolyte, by changing the viscous drag on the dyes. Some of these, which are described in U.S. Pat. No. 5,140,455, decrease the leakage current or the back reaction. Although ionic liquids are themselves conducting, other ionic species such as solid salts may also be added to depress their freezing points, change the ionic conductivity or provide other characteristics (e.g., ions for intercalation, etc.) as discussed later. Further, the presence of high concentrations of ionic species may suppress the bleaching reaction.

A mixture of a conventional solvent (i.e. a non-ionic solvent) and an ionic liquid, or a mixture of two or more ionic liquids provides electrolyte solutions with the high ionic concentrations of an ionic liquid and the low viscosity characteristic of conventional non-ionic solvents. Solvent mixtures may allow viscosity control, change in ionic conductivity, change in freezing point, change in kinetics of the electrooptic reactions, change in solubility (e.g. of other added ingredients such as dyes and UV stabilizers), enhanced processability, or other characteristics. Typically, it is preferred to keep the volume of a conventional organic solvent at less than 80% of the electrolyte solution, more preferably less than 30% and most preferably less than 20%. Another way of measuring the concentration is by molarity, i.e. moles of ions per liter of solution. A preferred concentration of all ionic species in the electrolyte solution is greater than 1 mol/l and more preferably greater than 2 moul/l and most preferably greater than 3 mol/l. Assuming no change in volume after mixing 1-butyl-3-imidazolium bis(trifluoromethanesulfonyl)imide and propylene carbonate in a 80%/20% mixture by volume, a 2.7 molar (M) concentration of the ionic species is present. As shown in EXAMPLES 8 and 9 (vide infra), mixed ionic liquid-conventional solvent systems provide benefits such as lowered Tg, as well as high coloration uniformity, and an acceptable leakage current (the leakage current of a device is measured by applying a steady voltage to hold the device in a given state of optical transmission or reflection and then measuring the current in the steady state).

The most preferred non-ionic co-solvents are propylene carbonate, ethylene carbonate, sulfolane, methyl sulfolane, and gamma-butyrolactone. Many other solvents that can be used as co-solvents can be found in U.S. Pat. No. 6,245,262 to D. Varaprasad et al. (vide supra). Non-ionic solvents in the U.S. Pat. No. 6,245,262 are referred to as plasticizers, and include triglyme, tetraglyme, acetonitrile, benzylacetone, 3-hydroxypropionitrile, methoxypropionitrile, 3-ethoxypropionitrile, butylene carbonate, propylene carbonate, ethylene carbonate, glycerine carbonate, 2-acetylbutyrolactone, cyanoethyl sucrose, gamma-butyrolactone, 2-methylglutaronitrile, N,N'-dimethylformamide, 3-methylsulfolane, methylethyl ketone, cyclopentanone, cyclohexanone, 4-hydroxy-4-methyl-2-pentanone, acetophenone, glutaronitrile, 3,31-oxydipropionitrile, 2-methoxyethyl ether, triethylene glycol dimethyl ether, or combinations thereof.

Self-erasing electrochromic devices constructed as shown in FIG. 1 show exceptionally even coloration. Devices of this construction have at least one electrochemically active material, sometimes referred to as a redox active material or redox dye, providing a redox reaction that is accompanied by a color change. The devices constructed as per FIG. 1 are also referred to as single compartment, as all the electrochemical activity takes place only in one compartment defined by the electrolyte layer contained within two conductors and the gasket. Self-erasing refers to the spontaneous or automatic reversal of the electrooptic coloration, which occurs shortly (e.g. typically seconds to minutes, but may be longer depending on the electrolyte composition) after the activating power to the device is removed. The device then returns to its non-powered state of coloration. Reversion to the optical properties of the device in the non-powered state should occur quickly, e.g. in less than five minutes, and preferably in less than thirty seconds, for a electrochromic dimming mirror; these times refer to the time for bleaching and coloration to 50% of the coloration range. Desirable coloration and bleaching times depend on the use of the electrooptic device. Electrochromic windows can have much slower coloration times and should have much slower bleaching times, sometimes referred to as the open circuit memory as described in A. W. Czandena et al. in "Durability issues and service lifetime prediction of electrochromic windows for buildings applications," Solar Energy Materials and Solar Cells, vol. 56, (1999), pp. 419–436, incorporated herein by reference. A. W. Czanderna et al. describe many of the desirable properties of electrochromic architectural windows. Electrooptic displays, such as computer displays, should have faster kinetics, while signage that is occasionally updated can have slower kinetics. Self-bleaching occurs because the devices have a competing back reaction in the powered state that is measured by the leakage current in the steady state for a given coloration for a given driving power characteristics (voltage). Some back reaction is required for self-erasure, e.g. for automotive rear-view mirrors. However, high values cause many other problems, such as uneven bleaching as described below. The forward reaction, e.g. coloration, is enhanced by the high ionic concentration of the electrolyte solutions that are part of the present invention, while the back reaction, e.g. bleaching, is slowed by the viscosity of the liquid electrolytes and the concentration of the ionic species. Fast forward reactions and slow back reactions lead to more uniform voltage across the area of the device and highly uniform coloration of the electrooptic devices of the present invention. The uniform coloration in the present invention is beneficial in several ways. First, uniform coloration allows larger area devices to be made, wherein these devices color uniformly when the power is applied via the conductors, typically busbars, at the perimeter of the device. In typical devices where the ionic concentration is low, the devices color deeper close to the busbar region at the perimeter then in the middle, as the size of the device increases. A second advantage of the conductivity of the ionic liquids used in electrooptic devices of the invention is that the voltage across the device is more uniform, reducing electrophoretic segregation of the redox dyes in the activated. By contrast, in electrooptic devices using conventional non-ionic solvents, electrophoretic separation of the redox dyes leads to formation of colored bands near the busbars when the power is left for long periods, e.g., for tens of minutes and longer. Third, the back reaction and forward reaction usually do not uniformly increase with temperature, and in electrooptic devices using conventional non-ionic solvents the difference in rates between the forward reaction and back reaction may be so high that a uniformly coloring device at 25° C. may color non-uniformly at 40° C. Again, non-uniformity tends to increase with increasing size of the device, most deleteriously with the increase in the distance between the busbar and the part of the electrodes farthest from the busbar. Temperature variation particularly affects exterior automotive mirrors, which are typically larger than the interior mirrors and may be heated to remove frost in cold weather or they may require coloration during the day to increase safety to be able to reduce solar glare. With increasing mirror size non-uniformity and temperature induced non-uniformity becomes more evident and this problem may be less severe in the electrooptic device of the present invention as compared with electrooptic devices using conventional non-ionic solvents.

Figure 10:
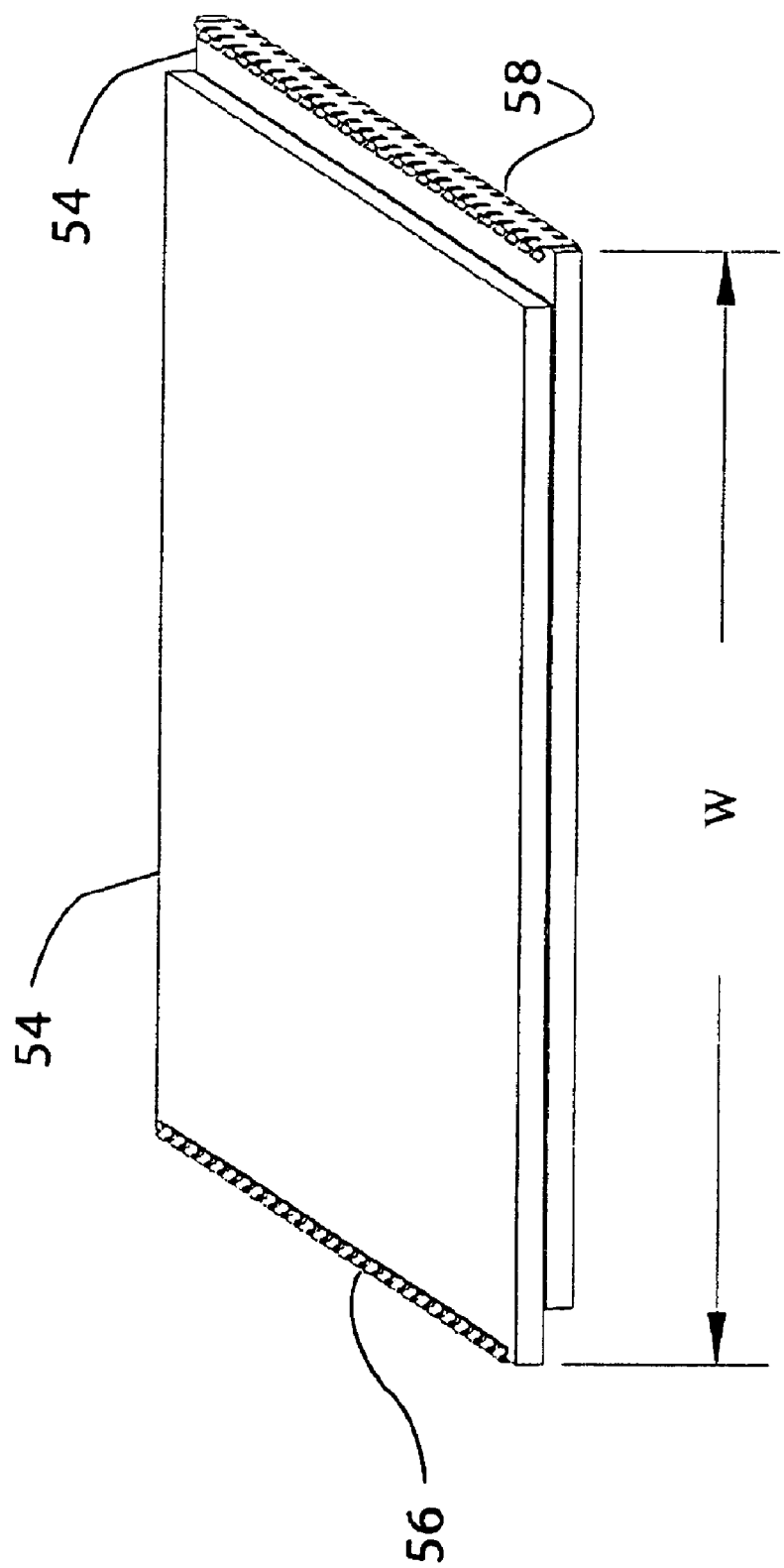
FIG. 10 shows the method for measuring the distance between the busbars of an embodiment of the present invention.

The concentration of ionic species in the electrolytes of EC devices is the sum-total of all the species that are salt-like (i.e. which have an anion and a cation) including ionic liquids, salts, dyes, etc. Another way of measuring the device size is to measure the distance between the opposite polarity busbars as shown in FIG. 10. FIG. 10 shows an electrochromic device made using two substrates 54 with their conductive sides facing inwards. The busbars for the two opposite electrodes 56 and 58 are shown at a distance "W". The shapes of the mirrors may be such that this distance may not be constant, thus average numbers are used. Also, the EC device size may be measured by measuring the width within the perimeter seal. For most practical devices, however, "W" is not significantly different from this as the seal and the busbar width only adds a few millimeters on each side. Distance "W" between the busbars for interior auto mirrors may be in the range of about 5 cm to 8 cm and for outside auto mirrors may range from about 7 cm to 20 cm. The thickness of the electrolyte layer for electrooptic devices made from this invention is generally lower than 1 mm, and more preferably lower than 0.5 mm. For automotive electrochromic mirrors this distance is preferably lower than 0.25 mm, so that self-erasure rate is acceptable.

Any value of leakage current is acceptable as long as the device colors uniformly and self-erasure occurs at an acceptable rate. Thus leakage current may be different for different sized mirrors. For an interior mirror having a size of about 25 cm by about 6 cm, the leakage current should preferably be lower than 0.5 mA/cm$^2$ of the active area of the device.

Polymerizable materials, such as co-reacting monomers, addition-reaction monomers, catalysts, initiators, etc., may be added to the electrolytes. Monomers can be polymerized in-situ after introducing the electrolyte into the device, or they may be solidified as a film and then laminated. Also the composition depends on the method of processing, such as curing by thermal, UV or other radiative method. Since the monomeric additives may become incompatible after polymerization, one has to be careful in exercising the choice of material. Details on materials, processing, etc. are described in U.S. Pat. No. 6,245,262, and in U.S. Pat. No. 5,940,201. Generally, the preferred ones are based on epoxy, urethane and acrylic chemistry. To keep the shrinkage low for in-situ polymerization, the concentration of additives is typically below 25% of the solvent.

Non-electrochemically active dyes (to give desired colors), surfactants and other modifiers may be added to the electrolyte solution, depending on the desired device characteristics and processability. These are described in the above references. As an example, near-IR absorbers have also been added (see: D. Thieste et al. in PCT Application WO 99/45081 entitled "Near Infrared-Absorbing Electrochromic Compounds and Devices Comprising the Same," incorporated by reference herein) so that the devices can absorb in an extended solar range for window applications.

EC devices of the present invention may contain other layers deposited on one of the electrodes. Schematics of these devices are shown in FIGS. 2 and 3. Device 34 shown in FIG. 2 is similar to the device 10, shown in FIG. 1, except that device 34 has the additional electrochemically active layer 36. Electrochemically active layer 36 is deposited on either conductive layer 16 or conductive layer 18 (or on substrate 12 or substrate 14 if they are themselves conductive) or both; for convenience, electrochemically active layer 36 is shown as deposited on second conductive layer 18. Examples of materials used for preparing electrochemically active layers are tungsten oxide, Prussian blue, molybdenum oxide, vanadium oxide, polyaniline, polythiophene, polypyrrole, and derivatives and mixtures of these materials (devices made with these layers are described in U.S. Pat. No. 4,671,619 to T. Kamimori et al. entitled "Electro-optic Device," which issued on Jun. 9, 1987, and in U.S. Pat. No. 5,729,379 to P-M. Allemand et al. entitled "Electrochromic Devices," which issued on Mar. 17, 1998, both incorporated by reference herein).

Any of the layers 16, 18, and 36 themselves may include several layers. The conductive layer of tin oxide, for example, may be deposited on top of an anti-iridescent coating. The electrochemically active layer may be a composite of two different layers of materials.

In this construction, solution 30 will include an ionic liquid and at least one redox-active compound. For example, if tungsten oxide is used, which is a cathodic layer, then at least one anodic material (e.g., ferrocene, phenothiazine) is used in the electrolyte. The electrolyte may also contain salts of lithium, sodium and potassium, etc. During the coloration, ions ($Li^+$, $Na^+$, $K^+$) from the electrolyte are reversibly injected into the tungsten oxide. It is preferred that if such salts are used the related anion is similar to, or the same as the one of the ionic liquid solvent. A material that combines the redox property of a dye and a source of lithium is lithium iodide salt (see, for example, U.S. Pat. No. 4,671,619 to T. Kamimori et al.).

An example of an anodic electrochemically active layer 36 is polyaniline, which can be used with a cathodic dye such as a viologen in the electrolyte solution of the invention.

There may be additional functional coatings to modify the functionality of the device 34 in FIG. 2. One example is device 38, shown in FIG. 3, which is identical to device 34 except that electrochemically active layer 36 is further coated with an ion selective transportation layer 40 which primarily allows e.g., lithium to go through but blocks or retards the motion of the larger ions present in the solution 30. Ion selective transportation layer 40 limits the back reaction and increases the memory of the devices. This is a useful feature for large windows as coloration is more uniform. Ion selective transportation layers and devices are described in U.S. Pat. No. 6,178,034 to P. M. Allemand et al. entitled "Electrochromic Devices," which issued on Jan. 23, 2001, hereby incorporated by reference.

In some EC devices there may be two intercalation layers as shown in FIG. 4. FIG. 4 shows device 42, which is similar to device 34, except that each of conductive layers 16 and 18 is coated with an electrochemically active layer. FIG. 4 depicts first conductive layer 16 as being coated with electrochemically active layer 44 and second conductive layer 18 coated with electrochemically active layer 36. One of the electrochemically active layers, layer 44 or layer 36, must be electrochromic; the other electrochemically active layer 44 or 36 (counterelectrode, CE) may be electrochromic or only store the ions reversibly. If the electrochromic layer includes tungsten oxide or molybdenum oxide, then the other electrochemically active layer may include polyaniline, nickel oxide, iridium oxide and vanadium oxide. Examples of non-electrochromic layers that store ions are cerium-titanium and vanadium-titanium oxide. During the device assembly, one of these layers is typically pre-reduced or intercalated with cations, such as lithium. The device changes its optical properties when the ions are ejected from the counterelectrode and injected in the electrochromic layer. For anodic electrochromic layers ejection of charge also leads to a change in color. Solution 30 in device 42 may include a UV stabilizer in addition to the ionic liquid solvent. Solution 30 in device 42 may optionally include a salt that has cations that may be transported from the CE to the electrochromic layer and vice-versa. As an example if lithium is being intercalated in the electrodes, then a lithium salt may be added to the electrolyte. One may even add a source of protons as long as the source of protons, typically an acid is able to dissociate in the electrolytic medium. Further, the anion of the added salt should be preferably similar to the anion of the ionic liquid. Examples of preferred lithium salts are lithium trifluoromethylsulfonate, lithium bis (trifluoromethylsulfonyl)imide, lithium bis (perfluoroethylsulfonyl)imide, and lithium tris (trifluoromethylsulfonyl)methide. Examples of electrochromic layers, counterelectrodes and device assembly can be found in the following patents: U.S. Pat. No. 6,266,177 to P. M. Allemand entitled "Electrochromic Devices," which issued on Jul. 24, 2001, U.S. Pat. No. 6,327,070 to H.-W. Heuer et al. entitled "Electrochromic Assembly Based on Poly(3,4-ethylenedioxythiophene) Derivatives in Combination With a Lithium Niobate Counterelectrode, which issued on Dec. 4, 2001, and U.S. Pat. No. 6,172,794 to M. S. Burdis entitled "Electrochromic Devices," which issued on Jan. 9, 2001).

Other chromogenic devices that use electrolytes can also benefit from the electrolyte solutions of the present invention. These are called User Controlled Photochromic Devices (UCPC) and photoelectrochemical devices (see, for example, U.S. Pat. No. 6,246,505 to G. Teowee et al. entitled "Photochromic Devices," which issued on Jun. 12, 2001, and C. Bechinger et al. "Photoelectrochromic Windows and Displays," Nature, vol. 383 (1996) pp. 608–610). In these devices the coloration is photoactivated and may be controlled by the user. These could be similar in construction to device 42 shown in FIG. 4.

The invention also includes a method for preparing electrooptic devices by vacuum backfilling. Many kinds of electrooptic devices can be manufactured by vacuum-backfill techniques, including electrochromic, electroreflective, and electroluminscent devices, and including mirrors, windows, filters, lighted panels and displays.

The electrooptic devices comprising ionic liquids of the present invention may be conveniently manufactured using a vacuum-backfill method. The negligible vapor pressures of ionic liquids allow vacuum-backfill techniques to be employed without the concerns of bubble formation and solvent contamination of the filling apparatus, as is the case with conventional non-ionic solvents. Further, and importantly, the negligible vapor pressure of ionic liquids even at elevated temperatures (see EXAMPLE 14) ensures that the solvent does not evaporate and therefore change the concentration of the solutes dissolved in the solvent.

As explained earlier, due to the low vapor pressure of the ionic liquids this is a very attractive method for device assembly. In this process, an empty cell (without electrolyte) with a fill port and the electrolyte in a separate vessel are placed in a chamber and evacuated. The fill port of the cell is then lowered into the electrolyte while still under vacuum. The chamber vacuum is then released while the fill port is still submerged in the electrolyte solution. If the viscosity of the solution is high (e.g. greater than 10 centipoise (cP)), the electrolyte solution is warmed by contacting the electrolyte solution with the warm, empty cell during the filling process; by warming the electrolyte or by conducting the filling operation in a heated chamber; or by some other means. The ambient pressure on the electrolyte forces it to fill the cell. The filled cell is removed and the fill port is sealed.

Figure 5B:
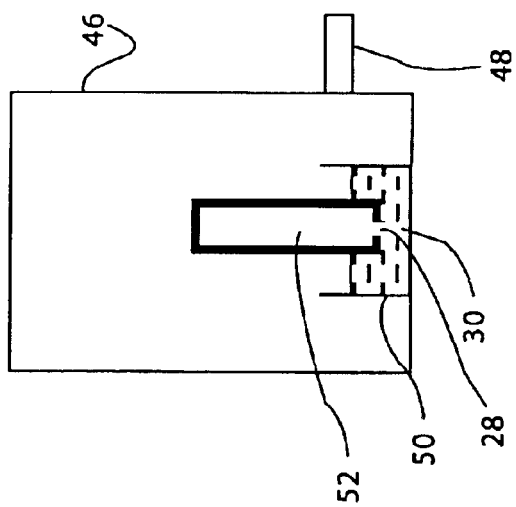
Figure 5A:
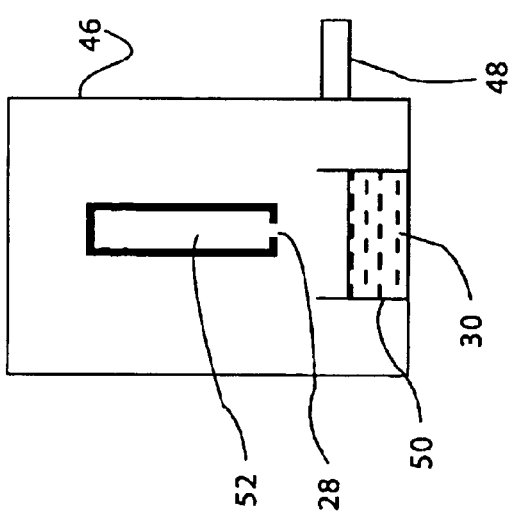

FIG. 5a shows a vacuum chamber 46. Port 48 is used for evacuating or introducing air or a gas (e.g., inert gas) into chamber 46. FIG. 5a shows the backfill process after a vacuum has been established in chamber 46. Chamber 46 may have other ports for introducing electrolytes and cells, which are not shown. The chamber contains vessel 50, which holds a solution 30. Chamber 52 formed by two substrates and a gasket (e.g. chamber 26 formed by gasket 24, first substrate 12, and second substrate 14, along with any coatings on those substrates). The gasket has a fill port 28 that is used to fill the chamber 52 with the solution 30. Fill port 28 can be one or more holes in the substrates. The substrates may have other layers as shown in FIGS. 1 through 4 already incorporated before the cavity formation. To start the backfilling process one or more of the empty cells along with the electrolyte is introduced in the chamber. The ionic liquid solution 30, comprising one or more ionic liquids, optionally a non-ionic co-solvent, one or more redox dye, optionally one or more UV stabilizers, optionally one or more in situ polymerizable monomers, and optionally one or more polymerization catalysts and/or initiators, is also introduced into the vacuum chamber. The cell and the ionic liquid solution are kept apart while the chamber is evacuated. If the fill solution has an appreciable vapor pressure, as is the case with non-ionic conventional solvents as described in U.S. Pat. No. 5,140,455, then the solvent will evaporate and prevent the establishment of a vacuum greater than the vapor pressure of the solvent. Also, if the fill solution has an appreciable vapor pressure, as is the case with non-ionic conventional solvents as described in U.S. Pat. No. 5,140, 455, then the evaporation of the solvent, especially under vacuum, and especially at elevated temperatures, may alter the concentration of solutes from their optimal values; since ionic liquids do not evaporate under conditions in which conventional solvents evaporate, the concentrations of the solutes do not change. Since the vapor pressure of the ionic liquids is negligible, the chamber is evacuated quickly, and further, electrolyte is not consumed by the vacuum system. In addition, for conventional liquids a bubble is always left in the backfilled cavity, and this is dependent on the vapor pressure, e.g., see U.S. Pat. No. 5,140,455 for a detailed description of this phenomenon. Since the vapor pressure of the ionic liquids of the present invention is negligible, the vacuum chamber may be quickly and efficiently evacuated, without consumption of solvent by the vacuum system or formation of bubbles. The fill port of the cell is then lowered into the ionic liquid while the vacuum chamber is under vacuum, as shown in FIG. 5b. The chamber vacuum is then released while the fill port is still submerged in the electrolyte, and optionally, the chamber is pressurized above atmospheric pressure. The pressure difference between the outside of the cell and the inside of the cell causes the ionic liquid to fill the cell as shown in FIG. 5c, which depicts chamber 46 after the vacuum has been replaced with a pressure of inert gas or air that is higher than the vacuum that was previously established, and preferably atmospheric or higher pressure has been established in chamber 46. The filled cell is removed from the vacuum chamber and the fill port is sealed with an adhesive that cures thermally or by radiation such as by UV radiation. The vapor pressure of propylene carbonate, an often used material for the electrolytes is 0.03 mm of mercury at 20° C. Sulfolane is also employed in electrochromic devices as an additive; it has a melting point of 27.6° C. and it has a vapor pressure of 0.0062 mm at this temperature. The vapor pressure of the ionic liquids is negligible (Gordon, C. M., New developments in catalysis using ionic liquids, Applied Catalysis: General A, vol. 222, (2001) page101–117, Earle, J. M., *Diels-Alder reactions in ionic liquids*, Green Chemistry, vol. 1 (1999), pp. 23–25). For the purpose of this invention, a vapor pressures lower than 0.003 mm of mercury, preferably lower than 0.001 mm of mercury under backfilling conditions is a negligible pressure. Negligible pressure is defined by a test in which a solvent is placed in an open container with a 1.5 cm$^2$ opening under a vacuum of 0.1 mm Hg at 100° C. for 1 hour. Under these conditions the loss of solvent due to evaporation should be less than 1 mg, and preferably less than 0.1 mg.

Other fill techniques, such as those described in U.S. Pat. No. 5,140,455 may also be used to manufacture the electrooptic devices of the present invention. These other fill techniques include injection fill techniques where the electrolyte under pressure is forced into the cavity. It is preferred to provide another hole in the cavity to vent the gas as it is filled, alternatively, the injection fill device may also provide the venting function.

The following EXAMPLES demonstrate the operability of the invention.

EXAMPLE 1

Figure 6:
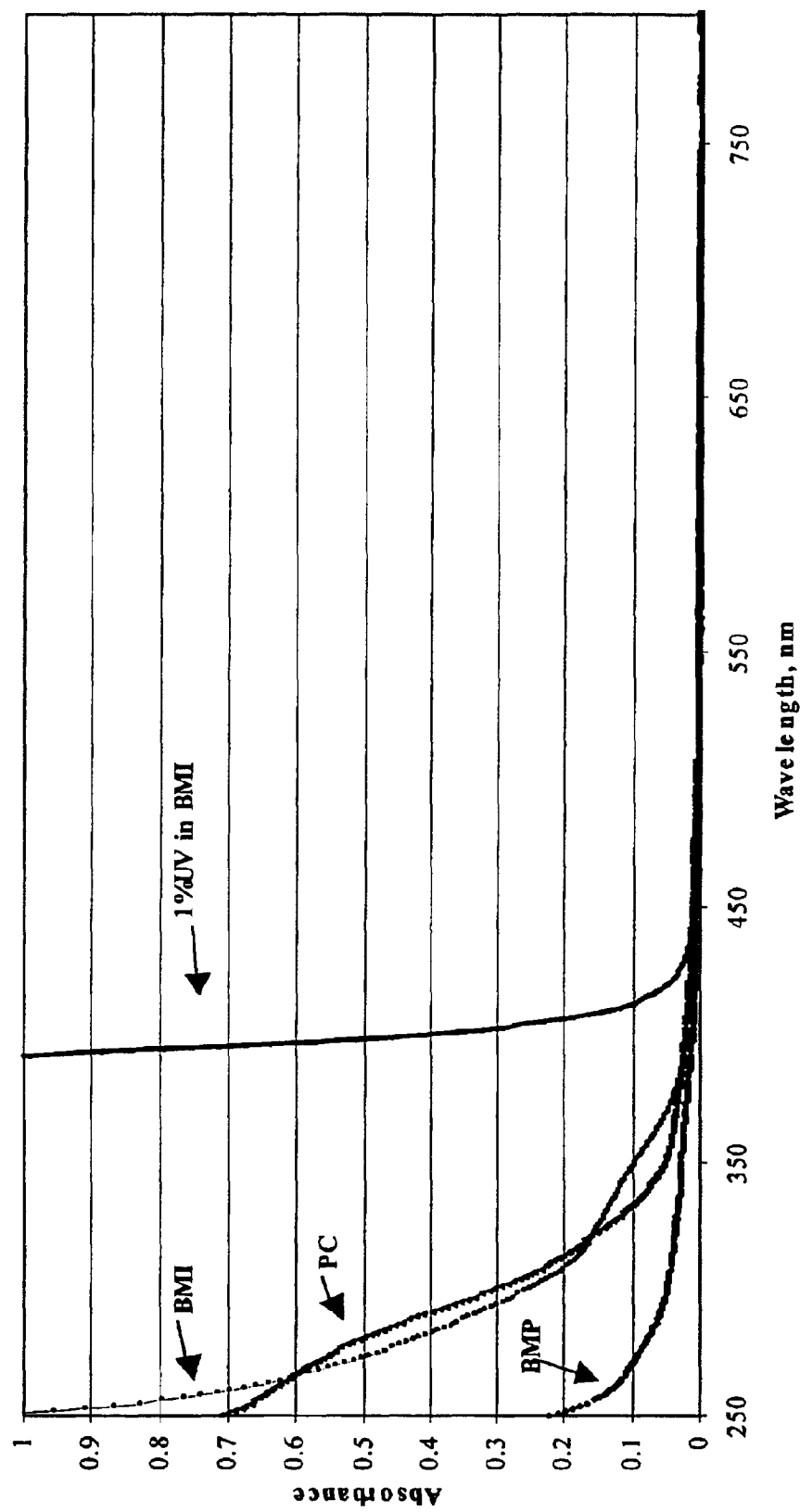
FIG. 6 shows the absorption spectra of several solvents.

Absorbance spectrum of UV stabilizer in ionic liquid solvent. The absorbance spectra propylene carbonate, 1-Butyl-3-methylimidazolium bis(trifluoromethylsulfonyl)imide (BMI), N-butyl-N-methylpyrrolidinium bis(trifluoromethylsulfonyl)imide (BMP), and a solution of BMI with 1% commercial UV stabilizer called Uvinul 3035 (ethyl 2-cyano-3,3-diphenyl-acrylate, available from BASF, Mount Olive, N.J.) were measured between 800 and 250 nm. Both BMI and BMP are ionic liquid solvents used with the invention. BMI has higher absorbance in the UV (below 400 nm) than BMP, due to its more conjugated nature. The solution of BMI with 1% UV stabilizer was a clear liquid that did not form a precipitate at −30° C. after 15 hours. The absorbance spectra of the four solutions are shown in FIG. 6.

EXAMPLE 2

Figure 7:
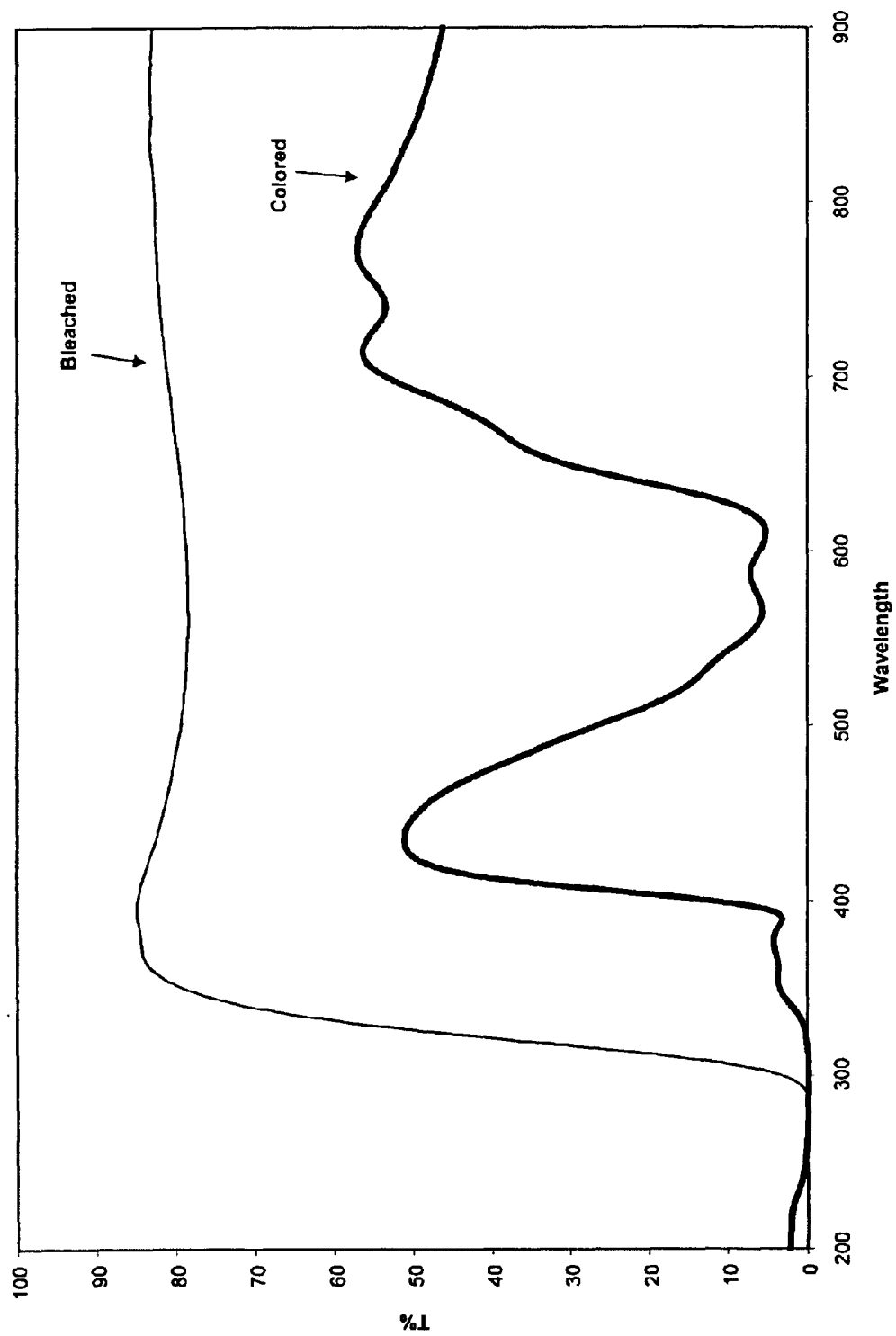
FIG. 7 shows the transmission spectra of an electrochromic device that includes redox dyes in the electrolyte in colored and the bleached state.
Figure 8:
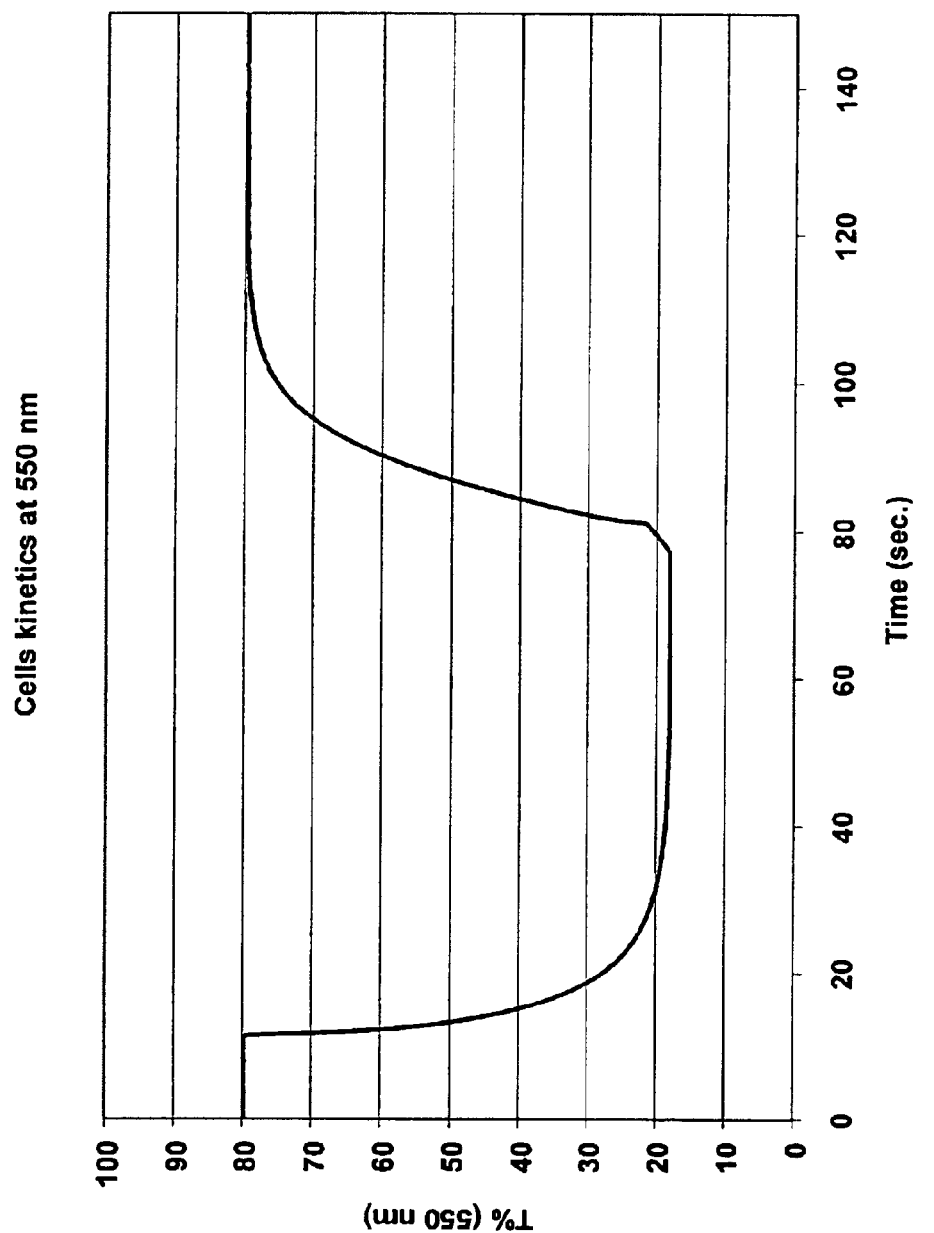
FIG. 8 shows a kinetic trace of an electrochromic device containing redox dyes in the electrolyte.

Electrochromic window device with electrolyte solution including redox dye. ITO substrate (15 Ω/sq) was cut into two 5.25"×3.7" rectangular pieces. Two holes about 3 mm in diameter were drilled into one piece near the corners of one of the diagonals. The substrates were then washed, dried and stored under clean room conditions. An epoxy containing 105 micron glass bead spacers was dispensed around the edges of one of the substrates, and the second substrate was placed on top of it to make a cavity such that the two substrates were slightly off-centered along the long side of the rectangular edge. This exposed edge on both substrates was later used to apply a busbar and make electrical connections. The epoxy seal was cured at a temperature of 120° C. The cavity was filled at room temperature with a liquid electrolyte solution containing 0.015M of the charge transfer complex formed by N,N'-dimethylviologen bis(trifluoromethanesulfonyl)imide (methyl viologen imide salt), 0.015M N,N,N',N'-tetramethyl-1,4-phenylenediamine in 1-butyl-3-methylimidazolium bis(trifluoromethanesulfonyl)imide. After the cavity was filled, the two holes were plugged with Teflon balls (preferably the diameter of the ball is 5 to 30% bigger than the diameter of the hole) and further sealed using cover glass and an epoxy. A solder strip was applied to the exposed ITO on each substrate along the long sides of the cavity using an ultrasonic solder. Electrical wires were then attached to these solder strips. The electrochromic performance of the window device was determined by placing the device in a spectrometer and monitoring the color kinetics at 550 nm while a color potential of 1.0 volts was applied. This device colored uniformly to a deep blue color and reversed to the original colorless state upon bleaching by shorting the electrical leads from the two electrodes. FIG. 7 shows the spectra in the colored and the bleached state. The kinetic trace for the device is shown at 550 nm in FIG. 8.

EXAMPLE 3

Figure 9:
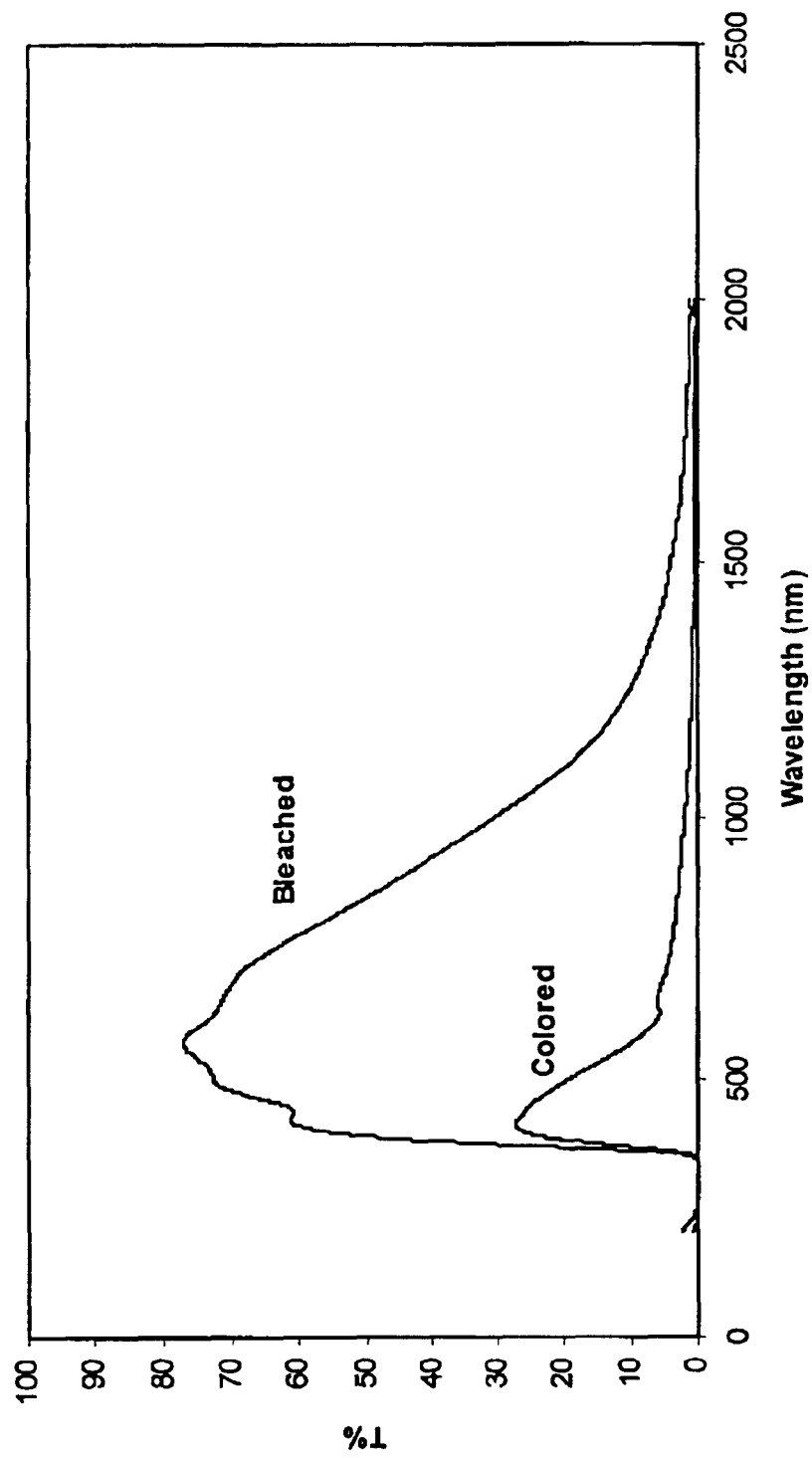
FIG. 9 shows transmission spectra of an electrochromic device that includes a layer of tungsten oxide in colored and the bleached state.

Electrochromic window device having a tungsten oxide coating. Two half wave ITO substrates (15 Ω/sq) were prepared as described in EXAMPLE 2 except that the substrate that was not drilled into was coated with a 300 nm thick tungsten oxide coating (on the conductive side) containing 30 mole % of lithium oxide (based on tungsten atoms). This coating was applied by a wet chemical method as described in U.S. Pat. No. 6,266,177. Any other method such as chemical vapor deposition and physical vapor deposition could have been used to deposit the tungsten oxide layer. The coating was fired at a temperature of 135° C. in a humid atmosphere, and then at 250° C. in air. It was then fabricated into a cell as described in EXAMPLE 1. The cavity thickness was 175 microns. The cavity was filled with electrolyte containing 0.1 molar lithium bis(trifluoromethanesulfonyl)imide, 0.015M ferrocene, 1 weight % Uvinul 3035 (from BASF, Mount Olive, N.J.) dissolved in 1-butyl-3-methylimidazolium bis(trifluoromethanesulfonyl)imide and the fill holes were plugged as described earlier in EXAMPLE 1. The electrochromic performance of the device was determined by placing the cell in a spectrometer and following the color kinetics at 550 nm while a color potential of 1.2 volts was applied followed by a bleach potential of −0.6 volts. In the transmissive (bleached) state the cell had a transmission of 76% T and fully colored of 12% T at 550 nm. The transmission spectra of the window device in the bleached and colored states are shown in FIG. 9.

EXAMPLE 4

Electrochromic window device with an electrolyte solution of redox dye and UV stabilizer dissolved in ionic liquid solvent. A device was prepare according to EXAMPLE 2 with the exception that it was filled instead with an electrolyte solution of N,N'-dimethylviologen bis(trifluoromethanesulfonoyl)imide (0.015 M), ferrocene (0.015 M) and 1 weight % Uvinul 3035 (BASF, Mount Olive, N.J.) dissolved in 1-butyl-3-methylimidazolium bis(trifluoromethanesulfonoyl)imide. The cell was colored using 1.0 volt and had a transmission at 550 nm of 41% and when shorted had a transmission of 76%.

EXAMPLE 5

Electrochromic window device with an electrolyte solution of redox dye and UV stabilizer dissolved in ionic liquid solvent. A device was prepared according to EXAMPLE 2 with the exception that it was filled instead with an electrolyte solution of the charge transfer complex formed by reacting N,N'-dimethylviologen dichloride hydrate and N,N,N,N'-tetramethyl-1,4-phenylenediamine (0.015 M) and 1 weight % Uvinul 3035 (from BASF, Mount Olive, N.J.) dissolved in 1-butyl-3-methylimidazolium bis(trifluoromethanesulfonoyl)imide. The cell was colored using 1.0 volt and had a transmission at 550 nm of 19% and when shorted had a transmission of 70%.

EXAMPLE 6

Mirror device with an electrolyte solution of redox dye system and UV stabilizer dissolved in ionic liquid solvent. An EC mirror was constructed using a substrate made from TEC 15 (from LOF, Toledo, Ohio), and another using indium-tin oxide (15 ohms/square). The TEC 15 substrate was mirrored on the non-conductive side using silver. ). The substrates were assembled as in EXAMPLE 2. The drilled counter electrode was the ITO electrode. The cell gap, i.e. the width of the electrolyte layer filling the gap, was 105 microns. After filling with an electrolyte solution of methyl viologen bis(trifluoromethanesulfonyl)imide (0.015 M), ferrocene (0.015 M) and 1 weight % Uvinul 3035 (from BASF, Mount Olive, N.J.) dissolved in 1-butyl-3-methylimidazolium bis(trifluoromethanesulfonyl)imide, the resulting device was colored at 1.0 V and shorted to bleach. At 550 mn the reflectance of the cell in the bleached mode was 71% and when colored it was 26%. At 550 nm, the time to color 50% of the range between 71% and 26% was 12 seconds and to bleach back 50% of range was 9 seconds.

EXAMPLE 7

Mirror device with an electrolyte solution of redox dye system and UVstabilizer dissolved in ionic liquid solvent. A device was prepared according to EXAMPLE 6, with the exception that it was filled instead with an electrolyte solution having the composition of 0.015M of the charge transfer complex formed between N,N'-dimethylviologen dichloride hydrate and N,N,N',N'-tetramethyl-1,4-phenylenediamine and 1 weight % Uvinul 3035 dissolved in 1-butyl-3-methylimidazolium bis(trifluoromethanesulfonyl)imide. The cell was colored at 1.0 volt and shorted to bleach. At 550 nm the reflectance of the cell in the bleached mode was 77% and when colored 7.7%. When a potential of 1V was applied, the device reached 50% coloration in 1.6 seconds and 80% coloration in 3.7 seconds.

EXAMPLE 8

Figure 11:
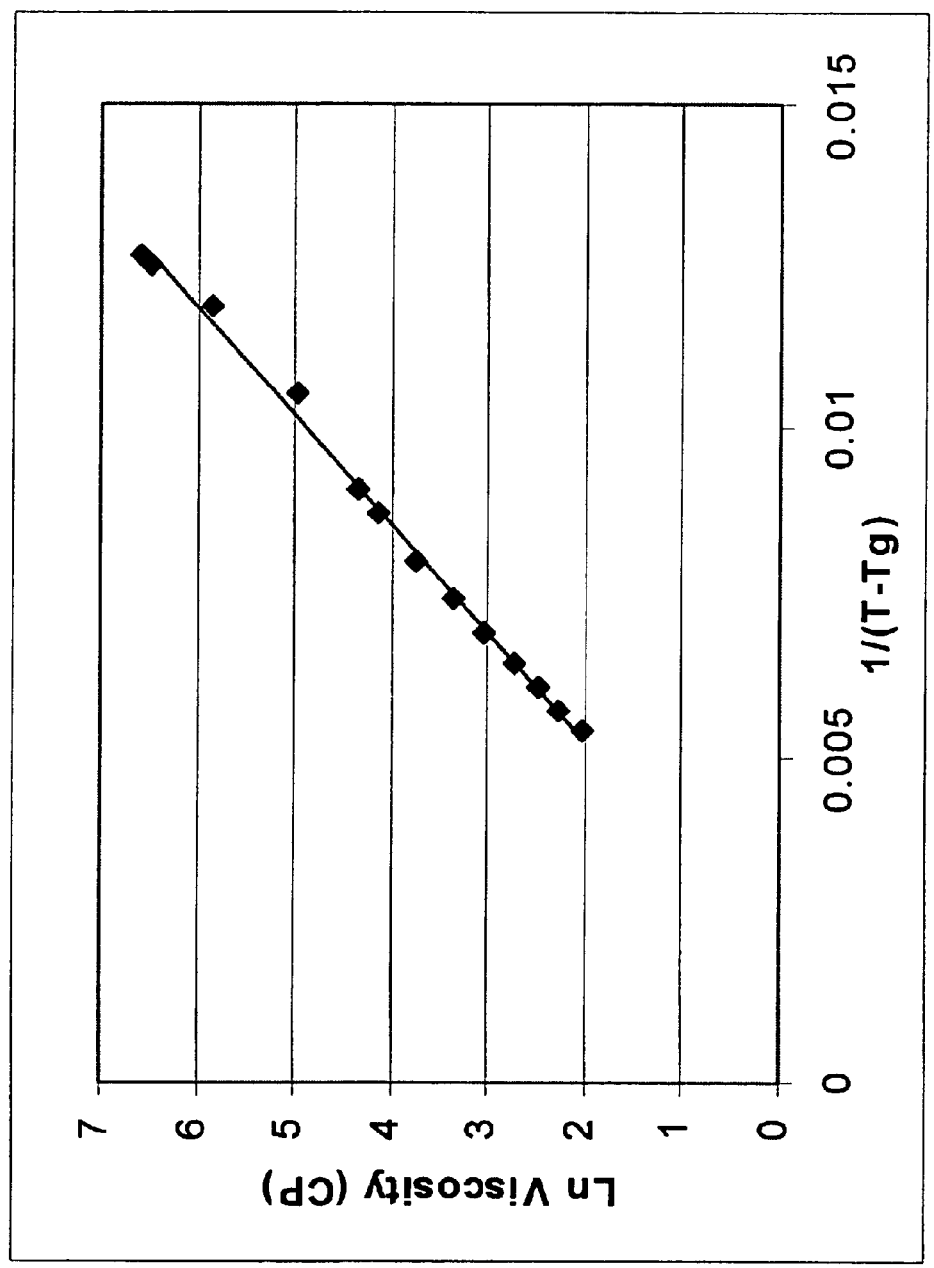
FIG. 11 shows a graph of data used to determine the Tg of an ionic liquid and a solution of an ionic liquid and a non-ionic liquid.
Figure 12:
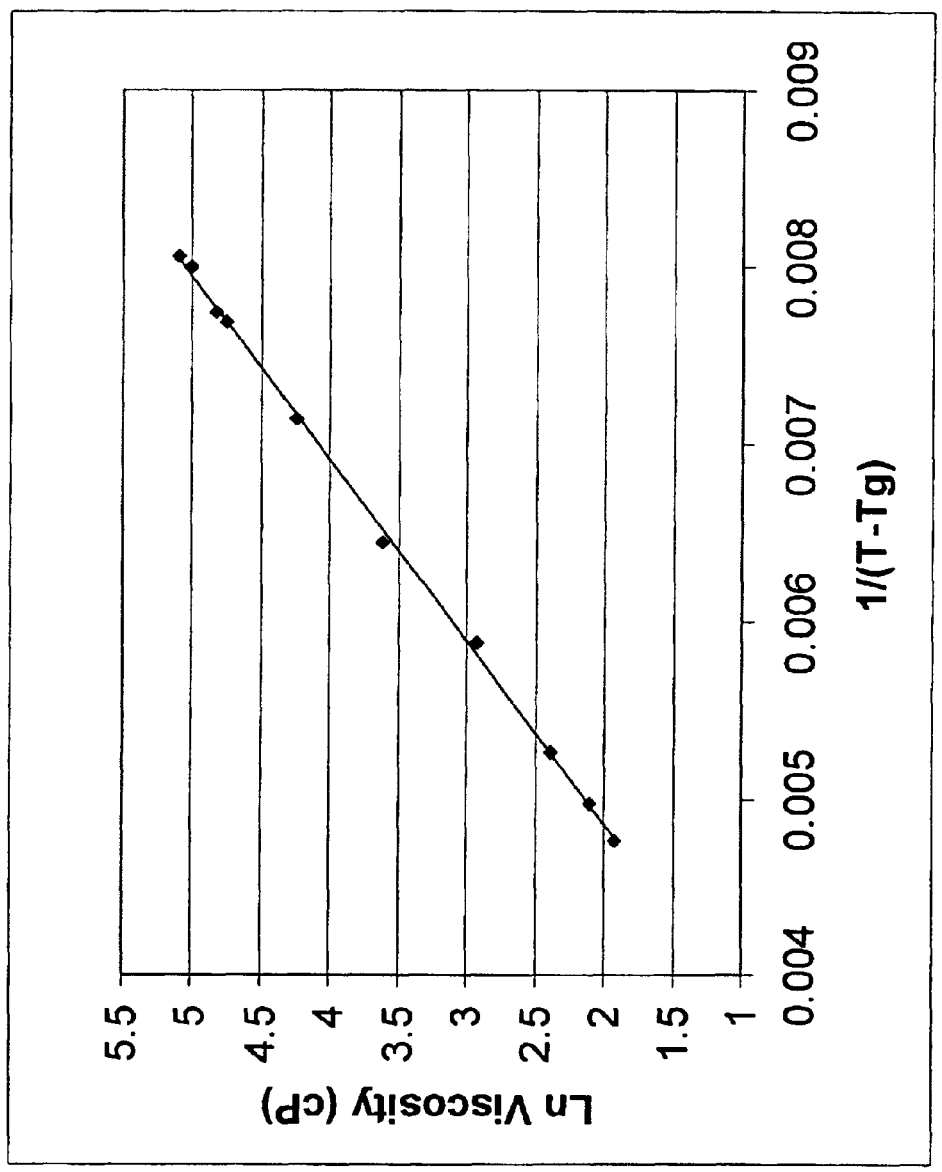
FIG. 12 shows another graph of data used to determine the Tg of an ionic liquid and a solution of an ionic liquid and a non-ionic liquid.

Measuring the viscosity and Tg of liquids. The viscosity of the 1-butyl-3-methylimidazolium bis(trifluoromethanesulfonyl)imide (BMI) and that of a mixture of BMI and propylene carbonate (PC) (90:10 by volume) were measured using a cone and plate attachment of a BROOKFIELD viscometer Model DV-III+ (Stoughton, Mass.) at different temperatures. This data obtained for each of these liquids are shown plotted in FIGS. 11 and 12. The data were fit to the following linear equation $$\ln(\text{viscosity}) = A + B/(T-Tg)$$

where T is the temperature of measurement in degrees centigrade, Tg is the glass transition temperature in degrees centigrade, and A and B are the fitting constants for the curve. The value of Tg was determined by varying the assumed value of Tg until the correlation coefficient of the curve was highest. For the fit in FIG. 11, the linear correlation coefficient ($R^2$) was 0.996 and for the solvent mixture shown in FIG. 12, the correlation constant was 0.999. The best fit equation for BMI was:

$$\ln(\text{viscosity}) = 601.41/(T-Tg) - 1.1483,$$

where the curve was best fit by a Tg of −85° C. The best fit equation for the mixture of BMI and propylene carbonate was:

$$\ln(\text{viscosity}) = 967.35/(T-Tg) - 2.694,$$

where the curve was best fit by a Tg of −130° C.

EXAMPLE 9

A comparison of EC devices employing three different electrolyte solutions. Three devices were made as described in EXAMPLE 2. The active area of each device was about 94 $cm^2$. The bifunctional redox dye was the charge transfer complex formed by reacting 5,10-dihydro-5,10-dimethylphenazine (phenazine) and N,N'-dimethylviologen bis[bis(trifluoromethanesulfonyl)imide] salt (viologen). The UV stabilizer was UVINUL™ 3035. The ionic liquid was included 1-butyl-3-methylimidazolium bis(trifluoromethanesulfonyl)imide. Table 1 below includes the weight in grams of each component of the electrolyte solution.

TABLE 1

| Component | Device 1 | Device 2 | Device 3 |
| --- | --- | --- | --- |
| Ionic Liquid | 18.765 | 20.85 | 0 |
| Propylene carbonate (PC) | 1.7835 | 0 | 17.835 |
| Phenazine | 0.1517 | 0.1517 | 0.1517 |
| Viologen | 0.5809 | 0.5809 | 0.5809 |
| UV Stabilizer | 1.064 | 0.8633 | 0.9284 |

As is shown in the Table above, Device 1 employed an electrolyte solution of ionic liquid and non-ionic additive propylene carbonate, device 2 employed ionic liquid without propylene carbonate, and device 3 employed propylene carbonate without any ionic liquid. The viscosity of the electrolyte in device 1 was 50 cP at 25° C. and 8 cP at 82° C. Tg of the electrolyte from the viscosity measurement was determined to be −140° C. The electrolyte thickness of device 1 and 2 was 63 microns. For device 3 this was 175 microns. When the thickness of device 3 was less, the leakage current was so high that the device did not color uniformly; specifically the center did not color to the same extent as the edges. The leakage current decreases with increasing electrolyte thickness, while the other parameters are held constant. Results from these devices are shown in Table 2 below. The transmission of the devices was measured using a fiber optic spectrometer while applying 0.9V for coloration.

TABLE 2

|  | Device 1 | Device 2 | Device 3 |
| --- | --- | --- | --- |
| % Transmission in bleached state at 550 nm | 85 | 85 | 83 |
| % Transmission in colored state at 550 nm | 21 | 20 | 31 |
| Leakage current (mA) in fully colored state | 27.6 | 19.8 | 44.4 |
| Normalized Leakage current (mA/$cm^2$) | 0.29 | 0.22 | 0.47 |

EXAMPLE 10

Synthesis of bifunctional redox dye, and EC device employing an electrolyte solution of the bifunctional redox dye dissolved in ionic liquid solvent. Chloromethylferrocene (1 g) was added to a solution containing 4,4'-bipyridine (681 mg) dissolved in acetonitrile (20 mL). This mixture was heated at 130° C. in a sealed tube for 24 hours. The tube was cooled and all of the solvent removed at reduced pressure affording a yellow solid that was then washed with hot toluene and dried to give methylferroceneviologen chloride (1.6 g). The methylferroceneviologen chloride (1.6 g) was dissolved in acetonitrile (20 mL) containing 5 mL of methyliodide. This was then heated at 100° C. for 24 hr, then cooled, and all solvent was removed at reduced pressure.

The resulting yellow solid was dissolved in water (100 mL) to form a clear solution. Lithium bis(trifluoromethanesulfonyl)imide (3 g) was then added to the clear solution. A dark precipitate of the N-methyl-N'-methylferroceneviologen bis(trifluoromethanesulfonyl)imide formed and was isolated by filtration (yield: 3.1 g). The product bifunctional redox dye, which has the structural formula

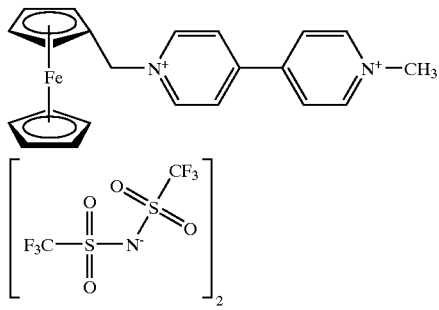

was used in an EC device by placing a solution of N-methyl-N'-methylferroceneviologen bis(trifluoromethanesulfonyl)imide in N-butyl-N-methylpyrrolidinium bis(trifluoromethylsulfonyl)imide in a chamber formed by two ITO plates and an o-ring. The resulting electrochromic device successfully colored and bleached repeatedly upon cyclic applications of a voltage across the cell.

EXAMPLE 11

EC device employing an electrolyte solution of ionic liquid solvent and bifunctional redox dye having cathodic moiety and europium anodic moiety. A mixture of 1.0 grams of Eu(II) chloride and 2 equivalents of hydrogen bis(trifluoromethanesulfonyl)imide was heated until gas evolution stopped. The product, Eu(II) bis(trifluoromethanesulfonyl)imide, was then purified by heating in a vacuum at 60° C. for four hours. Eu(II) bis(trifluoromethanesulfonyl)imide (100 mg) and N,N'-diethylviologen bis(trifluoromethanesulfonyl)imide (100 mg) were dissolved in N-butyl-N-methylpyrrolidinium bis(trifluoromethylsulfonyl)imide (2 mL). The resulting solution was placed between two ITO plates. The resulting electrochromic device successfully colored and bleached repeatedly upon cyclic applications of a voltage across the cell, presumably by oxidizing the Eu(II) to Eu(III) while at the same time reducing the diethylviologen to the corresponding radical cation.

EXAMPLE 12

Synthesis of bifunctional redox dye and use in an EC device. A mixture of 1-bromo-2-ethylhexane (1.2 g) and 4,4'-bipyridine (1 g) in acetonitrile (20 mL) was heated at 130° C. in a sealed tube for 24 hours to yield, after purification, 4-(2-ethylhexyl)-4,4'-bipyridine bromide (2 g). An aqueous solution of 4-(2-ethylhexyl)-4,4'-bipyridine bromide (0.5 g), sodium hydroxide (40 mg), and 1-bromoacetic acid (200 mg) was refluxed for 12 hrs, then lithium bis(trifluoromethylsulfonyl)imide (500 mg) was added and a white precipitate formed. The white precipitate, 4-(2-ethylhexyl)-4'-methylenecarboxylate-4,4'-viologen bis(trifluoromethylsulfonyl)imide, was filtered and dried (yield: 620 mg). 4-(2-ethylhexyl)-4'-methylenecarboxylate-4,4'-viologen bis(trifluoromethylsulfonyl)imide has the structural formula

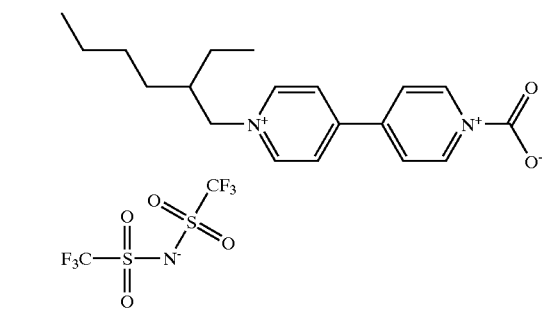

and was used in an EC device. 4-(2-ethylhexyl)-4'-methylenecarboxylate-4,4'-viologen bis(trifluoromethylsulfonyl)imide (602 mg) was mixed with Eu(II) bis(trifluoromethylsulfonyl)imide (518 mg), melted, and maintained as a melt for 15 minutes to form 4-(2-ethylhexyl)-4'-methylenecarboxylate(europium(II))-4,4'-viologen tris(bis(trifluoromethylsulfonyl)imide), which has the structural formula:

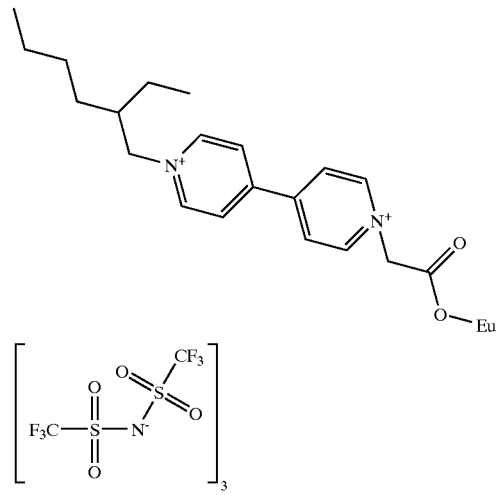

An electrochromic device using 4-(2-ethylhexyl)-4'-methylenecarboxylate(europium(II))-4,4'-viologen tris(bis(trifluoromethylsulfonyl)imide) was prepared by dissolving 4-(2-ethylhexyl)-4'-methylenecarboxylate(europium(II))-4,4'-viologen tris(bis(trifluoromethylsulfonyl)imide) (600 mg) in N-butyl-N-methylpyrrolidinium bis(trifluoromethylsulfonyl)imide (BMP, 3 mL). An EC device was prepared by placing the resulting electrolyte solution was placed in the chamber formed by an o-ring and two ITO electrodes. The device successfully colored and bleached repeatedly upon cyclic applications of a voltage to the electrodes of the device, which presumably functions by oxidizing the Eu(II) to Eu(III) and reducing the diethylviologen to the radical cation.

EXAMPLE 13

Figure 13:
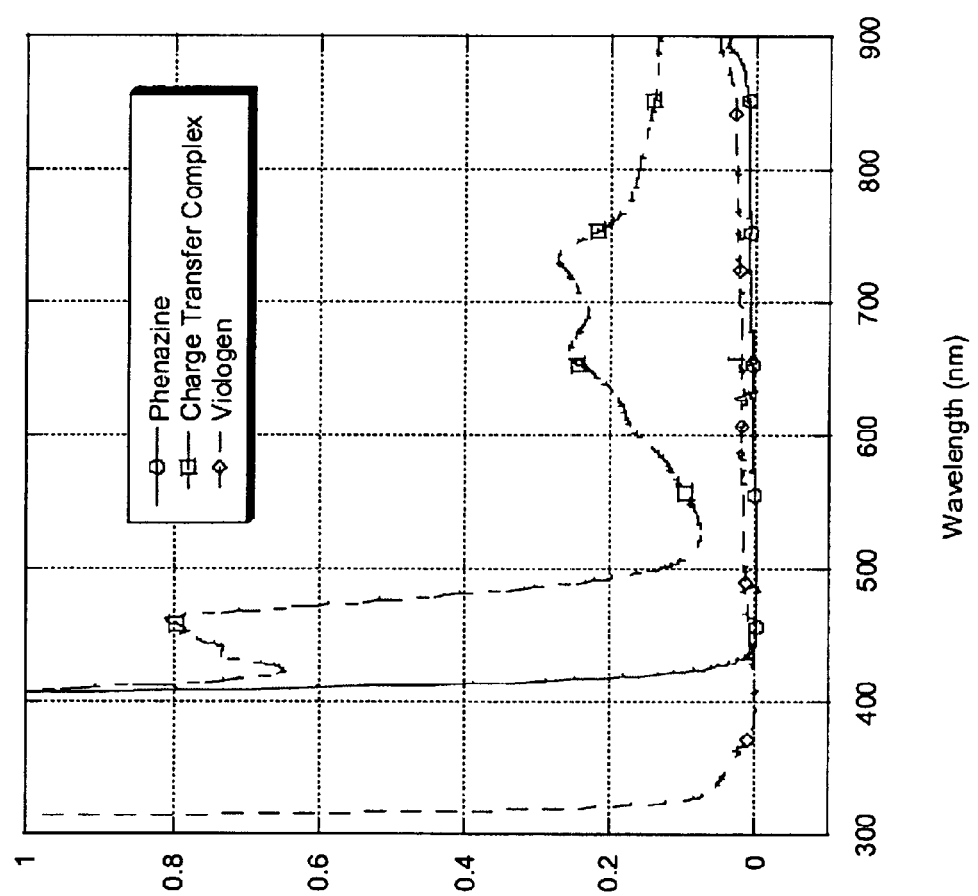
FIG. 13 shows the absorption spectra of a charge transfer complex and of the individual components.

Synthesis of bifunctional redox dye and use in an EC device. A charge transfer complex was prepared by mixing N,N'-diethylviologen bis(trifluoromethanesulfonyl)imide with one equivalent of 5,10-dihydro-5,10-dimethylphenazine (20 mg combined mass) in N-butyl-N-methylpyrrolidinium bis(trifluoromethylsulfonyl)imide solvent (10 mL). Solutions of N,N'-diethylviologen bis(trifluoromethanesulfonyl)imide (20 mg) in N-butyl-N-methylpyrrolidinium bis(trifluoromethylsulfonyl)imide (10 mL) and 5,10-dihydro- 5,10-dimethylphenazine (20 mg) in acetone (10 mL) were also prepared. The spectrum of the three solutions, measured between 300 nm and 900 nm, are shown in FIG. 13. The spectrum of N,N'-diethylviologen bis(trifluoromethanesulfonyl)imide in N-butyl-N-methylpyrrolidinium bis(trifluoromethylsulfonyl)imide is labeled "viologen"; the spectrum of 5,10-dihydro-5,10-dimethylphenazine in acetone is labeled "phenazine"; and the spectrum of the solution of N,N'-diethylviologen bis(trifluoromethanesulfonyl)imide and 5,10-dihydro-5,10-dimethylphenazine in N-butyl-N-methylpyrrolidinium bis(trifluoromethylsulfonyl)imide is labeled "charge transfer complex." The "charge transfer complex" spectrum displays new absorption bands at 450 nm, 665 mn, and 730 nm, which are not present in the spectra of the constituent N,N'-diethylviologen bis(trifluoromethanesulfonyl)imide or 5,10-dihydro-5,10-dimethylphenazine, strongly suggesting the formation of the charge transfer complex. The formation of the charge transfer complex was later confirmed by preparing a crystal of the complex and obtaining its X-ray crystal structure. An EC device was prepared as described in EXAMPLE 2, with the exception of filling the cavity with an electrolyte solution of 0.05M of the above charge transfer complex, 2-cyano-3,3-diphenyl-acrylic acid ethyl ester (5% by weight) in N-butyl-N-methylpyrrolidinium bis(trifluoromethylsulfonyl)imide solvent.

Figure 14:
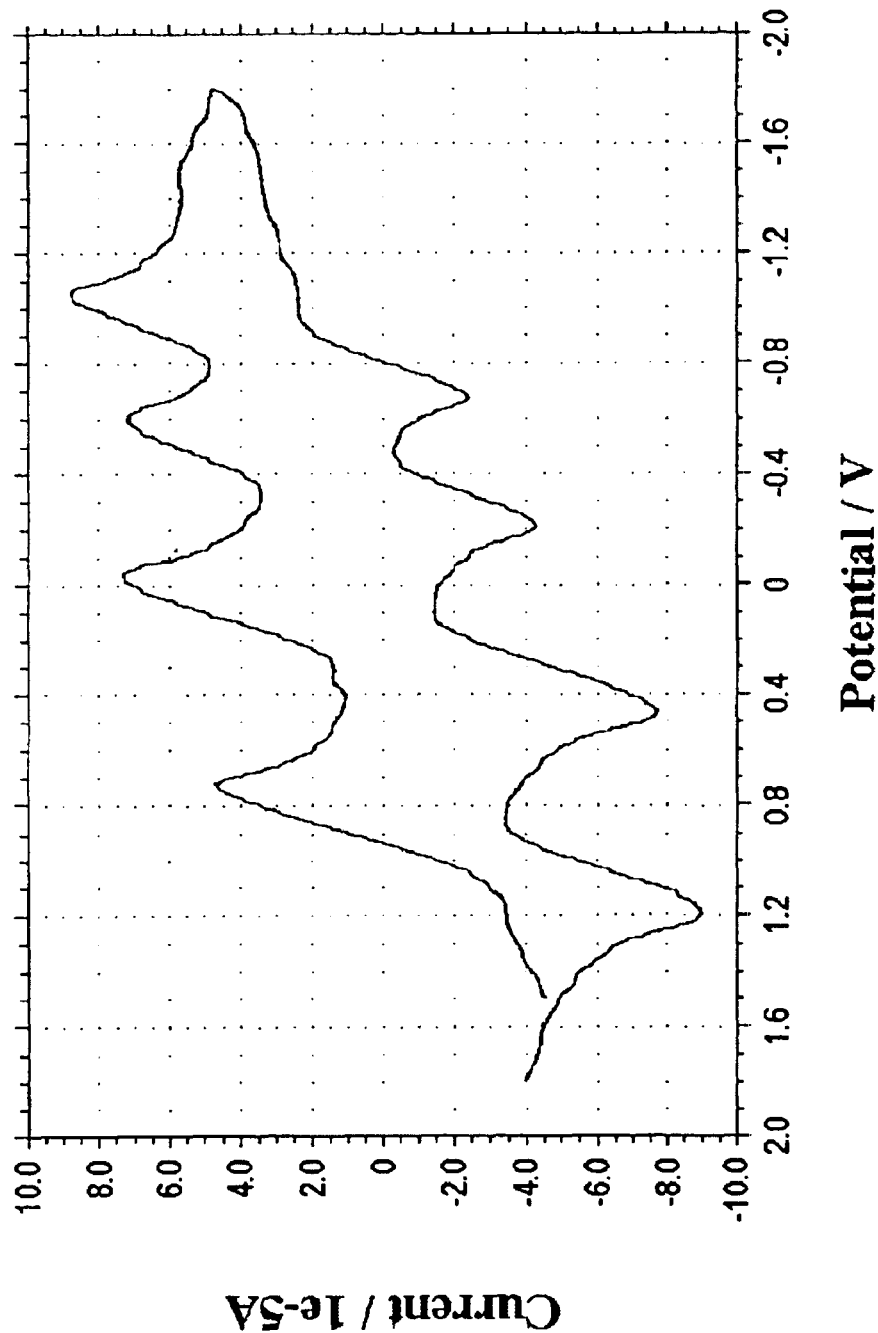
FIG. 14 shows a cyclic voltammogram of the charge transfer complex between 5,10-dihydro-5,10-dimethylphenazine and N,N'-diethylviologen bis(trifluoromethanesulfonyl)imide in N-butyl-N-methylpyrrolidinium bis(trifluoromethylsulfonyl)imide.

Devices with lower concentrations (0.03M) of the charge transfer complex and with 2% 2,4-dihydroxy benzophenone were also constructed and subjected to a set of tests including repeated cycling (79,500 cycles) at 70° C., and exposure to 2,000 kJ of UV light with no significant loss of performance. A cyclic voltammogram of the charge transfer complex between 5,10-dihydro-5,10-dimethylphenazine and N,N'-diethylviologen bis(trifluoromethanesulfonyl)imide in N-butyl-N-methylpyrrolidinium bis(trifluoromethylsulfonyl)imide solvent shows only one reversible oxidation wave, as shown in FIG. 14.

EXAMPLE 14

Weight loss of solvents in a vacuum. Propylene carbonate (1 g) was placed in a container having a surface area of 1.5 cm$^2$, which was then heated to 100° C. under a vacuum of 1 mm Hg. After 1 hour, atmospheric pressure was restored and the vial was cooled to room temperature. The sample was re-weighed, and 0.627 g of propylene carbonate remained. The ionic liquid N-butyl-N-methylpyrrolidinium bis(trifluoromethylsulfonyl)imide (BMP) (1 g) was placed in a container having a surface area of 1.5 cm$^2$, which was then heated to 100° C. under a vacuum of 1 mm Hg. After 1 hour, atmospheric pressure was restored and the vial was cooled to room temperature. The sample was re-weighed using a scale accurate to 1 mg, and no change in mass was observed.

EXAMPLE 15

An example of an electrochromic device with a multifunctional dye combining a viologen moiety and a ferrocene moiety. An EC window device was made in an interior rear-view mirror shape. This was approximately 25 cm in length and about 6 cm wide. The substrates were Sungate™ 300 glass (from PPG industries, Pittsburgh, Pa.) with a conductive tin oxide coating having a resistance of 40.5 ohms/sq. The electrolyte was backfilled through a hole left in the seal, which was plugged with a UV curing sealant after the filling operation. The electrolyte thickness was 100 microns and the electrolytic solvent was ionic liquid (1-butyl-3-methylimidazolium bis(trifluoromethanesulfonoyl)imide) and PC mixture. The electrolyte thickness was controlled by adding spacer beads to the perimeter seal material; the perimeter seal material is an epoxy resin. The electrolyte composition was 2.502 g of ionic liquid, 0.2378 g of PC and 0.0973 g of a bifunctional redox dye having a viologen moiety and a ferrocene moiety. When this device was colored at 0.9V its transmission at 550 nm decreased from 79% to 16%. This device showed good UV stability when tested in its bleached state using an exposure of 1000 kJ using UV intensity conditions prescribed in Society of Automotive Engineers' (Warrandale, Pa.) test J1960.

In summary, the present invention includes UV stabilizing, bifunctional redox dyes, electrolyte solutions of these dyes dissolved in ionic liquid solvents, and electrooptic devices employing these electrolyte solutions. These solutions typically have a Tg of −40° C. or lower, and provide electrooptic devices with excellent durability and performance.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An electrolyte solution having a Tg (glass transition temperature) of less than about −40° C., comprising at least one bifunctional redox dye dissolved in ionic liquid solvent.

2. The electrolyte solution of claim 1, wherein said bifunctional redox dye comprises at least one redox active anodic moiety and at least one redox active cathodic moiety.

3. The electrolyte solution of claim 2, wherein said anodic moiety of said bifunctional redox dye comprises a pyrazoline, metallocene, phenylenediamine, benzidine, phenoxadine, phenothiazine, tetrafulvalene or phenazine, and said cathodic moiety of said bifunctional redox dye comprises a viologen or anthraquinone.

4. The electrolyte solution of claim 1, wherein said bifunctional redox dye comprises at least one energy receptor moiety and at least one redox active anodic moiety, at least one energy receptor moiety and at least one redox active cathodic moiety, or at least one energy receptor moiety and at least one redox active anodic moiety and at least one redox active cathodic moiety.

5. The electrolyte solution of claim 4, wherein said bifunctional redox dye comprises a redox active moiety comprising a pyrazoline, metallocene, phenylenediamine, benzidine, phenoxadine, phenothiazine, tetrafulvalene, phenazine, viologen or anthraquinone, and an energy receptor moiety comprising a benzophenone, benzotraizole, or cyanoacrylate.

6. The electrolyte solution of claim 1, wherein said ionic liquid solvent comprises at least one cation selected from the group consisting of lithium cation and quaternary ammonium cations, wherein said quaternary ammonium cations are selected from the group consisting of pyridinium, pyridazinium, pyrimidinium, pyrazinium, imidazolium, pyrazolium, thiazolium, oxazolium, triazolium, tetraalkylammonium, N-methyl morpholinium, cations of the formula $[(CH_3CH_2)_3N(R_1)]^+$, wherein $R_1$ is alkyl having 2–10 carbons, cations of the formula $[(CH_3)_2(CH_3CHCH_3)N(R_2)]^+$, wherein $R_2$ is alkyl having 2–10 carbons, cations having the structural formula

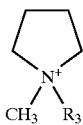

wherein $R_3$ is alkyl having 2–10 carbons, and cations having the structural formula

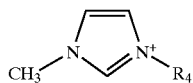

wherein $R_4$ is alkyl having 2–10 carbons.

7. The electrolyte solution of claim 1, wherein said ionic liquid comprises at least one anion selected from the group consisting of trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$).

8. The electrolyte solution of claim 1, wherein said bifunctional redox dye is a compound having the structural formula

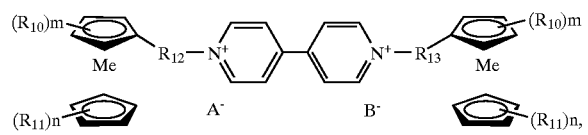

or having the structural formula

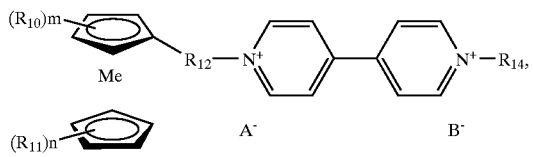

or having the structural formula

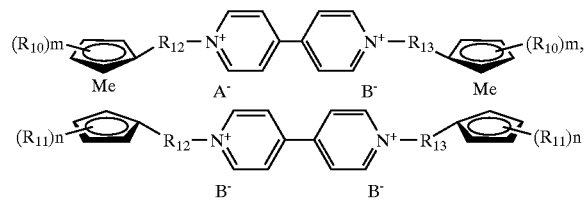

or having the structural formula

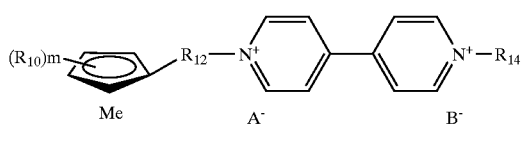
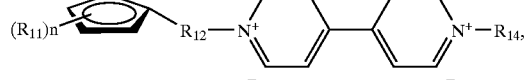

wherein $A^-$ is selected from the group consisting of trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$); $B^-$ is selected from the group consisting of a halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$); wherein $R_{10}$ and $R_{11}$ are each independently a hydrocarbon group selected from the group consisting of an alkyl, alkenyl and aryl group having 1 to 10 carbon atoms, in the case where $R_{10}$ or $R_{11}$ is an aryl group, the aryl group forms a condensed ring together with a cyclopentadienyl ring; wherein m=0–4; wherein n=0–4; wherein $R_{12}$ and $R_{13}$ are each independently a hydrocarbon residue having 1 to 20 carbon atoms, or alkylene groups having ester-bond unit, ether-bond unit, amide-bond unit, thioether-bond unit, amine-bond unit, urethane-bond unit, or silyl unit in the part of hydrocarbon groups, and $R_{14}$ is a hydrocarbon group selected from the group consisting of an alkyl, cycloalkyl, alkenyl, aryl, or aralkyl group having 1 to 20 carbon atoms, a heterocyclic group having 4 to 20 carbon atoms, and a substituted hydrocarbon or heterocyclic group obtained by substituting part of hydrogens of the hydrocarbon group or heterocyclic group with a substituent group; and Me represents Cr, Co, Fe, Mn, Ni, Os, Ru, V, Mo(X)(Q), Nb(X)(Q), Ti(X)(Q), V(X)(Q)or Zr(X)(Q) wherein X and Q are each independently selected from the group consisting of hydrogen, halogen, an alkyl group having 1 to 12 carbon atoms, $ClO_4^-$, $BF_4^-$, $PF_6^-$, $AsF_6^-$, $SbF_6^-$, $CH_3COO^-$, $CH_3(C_6H_4)SO_3^-$, trifluoromethylsulfonate ($CF_3SO_3^-$), bis(trifluoromethylsulfonyl)imide (($CF_3SO_2$)$_2N^-$), bis(perfluoroethylsulfonyl)imide (($CF_3CF_2SO_2$)$_2N^-$) and tris(trifluoromethylsulfonyl)methide (($CF_3SO_2$)$_3C^-$);

or having the formula $Cat_1$-$An_1$, or having the formula $Cat_1$-$Bridge_1$-$An_1$, or having the formula $Cat_1$-$Bridge_1$-$An_1$-$Bridge_2$-$Cat_2$, or having the formula $An_2$-$Bridge_2$-$Cat_1$-$Bridge_1$-$An_1$, wherein $Cat_1$-$An_1$ represents a charge transfer complex; wherein $Cat_1$ and $Cat_2$ independently represent a radical having the structural formula

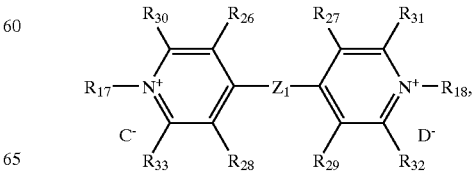

or having the structural formula

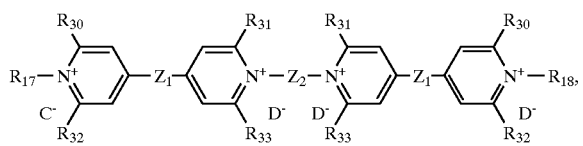

or having the structural formula

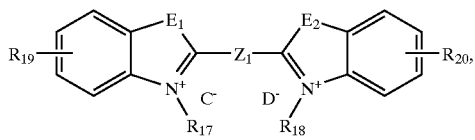

or having the structural formula

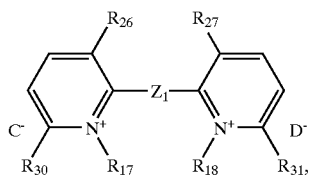

or having the structural formula

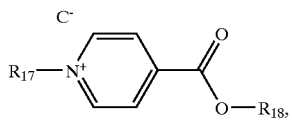

or having the structural formula

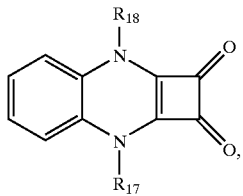

or having the structural formula

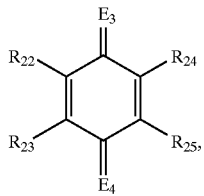

or having the structural formula

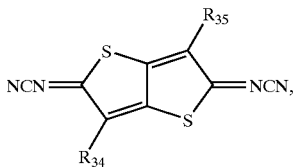

wherein $R_{17}$ and $R_{18}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl or $R_{17}$ and $R_{18}$ together form a —(CH$_2$)$_2$—, —(CH$_2$)$_3$—, or —CH=CH— bridge, $R_{19}$, $R_{20}$ and $R_{22}$ to $R_{25}$ independently of one another denote hydrogen, $C_1$ to $C_{18}$-alkyl, $C_1$ to $C_4$-alkoxy, halogen, cyano, nitro or $C_1$ to $C_{18}$-alkoxycarbonyl or $R_{22}$ and $R_{23}$ and/or $R_{24}$ and $R_{25}$ form a —CH=CH—CH=CH— bridge; $R_{26}$, $R_{27}$, $R_{28}$ and $R_{29}$ independently of one another denote hydrogen or, in pairs, a —(CH$_2$)$_2$—, —(CH$_2$)$_3$— or —CH=CH— bridge, $E_3$ and $E_4$ independently of one another denote O, N—CN, C(CN)$_2$ or N—C$_6$— to C$_{10}$-aryl, $R_{34}$ and $R_{35}$ independently denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl, $R_{30}$ to $R_{33}$ independently of one another denote hydrogen or $C_1$ to $C_6$-alkyl, or $R_{30}$ and $R_{26}$ and/or $R_{31}$ and $R_{27}$ form a —CH=CH—CH=CH— bridge, $E_1$ and $E_2$ independently of one another denote O, S, NR$_{36}$ or C(R$_{36}$)$_2$ or $E_1$ and $E_2$ together form a —N—(CH$_2$)$_2$—N— bridge, $R_{36}$ denotes $C_1$ to $C_{18}$-alkyl, $C_2$ to $C_{12}$-alkenyl, $C_4$ to $C_7$-cycloalkyl, $C_7$ to $C_{15}$-aralkyl or $C_6$ to $C_{10}$-aryl, $Z_1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z_2$ denotes —(CH$_2$)$_r$— or —CH$_2$—C$_6$H$_4$—CH$_2$—, r=1–10, C$^-$ is selected from the group consisting of bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), and D$^-$ is selected from the group consisting of halogen anion, ClO$_4^-$, BF$_4^-$, PF$_6^-$, AsF$_6^-$, SbF$_6^-$, CH$_3$COO$^-$, and CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), wherein bonding to the bridge member bridge$_1$ or bridge$_2$ is effected via one of the radicals $R_{17}$–$R_{36}$, and the radicals mentioned then represent a direct bond, and wherein An$_1$ and An$_2$ independently represent radicals having the structural formula:

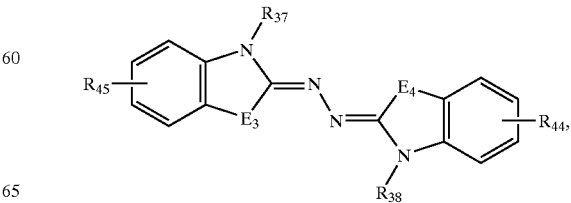

or having the structural formula

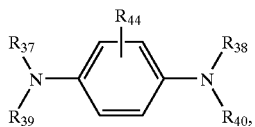

or having the structural formula

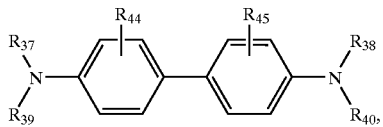

or having the structural formula

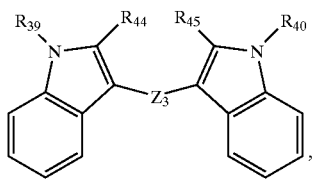

or having the structural formula

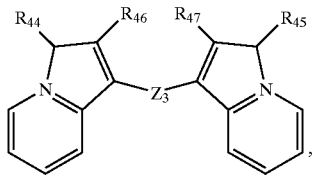

or having the structural formula

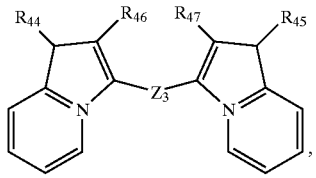

or having the structural formula

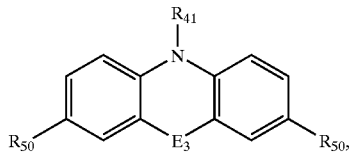

or having the structural formula

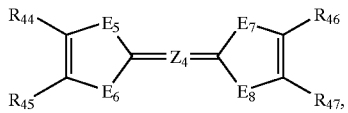

or having the structural formula

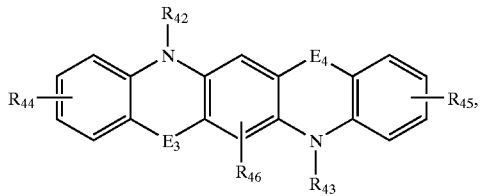

or having the structural formula

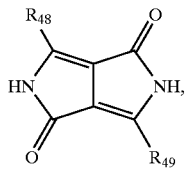

or having the structural formula

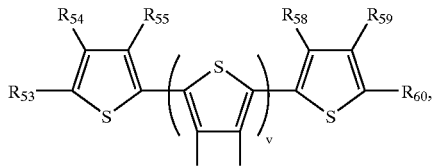

or wherein $An_1$ or $An_2$ independently represent a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II), wherein $R_{37}$ to $R_{43}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl, and $R_{41}$ to $R_{43}$ additionally denote hydrogen, $R_{44}$ to $R_{50}$ independently of one another denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl and $R_{48}$ and $R_{49}$ additionally denote an optionally benzo-fused aromatic or quasiaromatic five- or six-membered heterocyclic ring and $R_{50}$ additionally independently denotes $N(R_{51})(R_{52})$, $R_{44}$ and $R_{45}$ and/or $R_{46}$ and $R_{47}$ form a —$(CH_2)_3$—, —$(CH_2)_4$—, —$(CH_2)_5$— or —CH=CH—CH=CH— bridge, $Z_3$ denotes a direct bond or a —CH=CH— or —N=N— bridge, $=Z_4=$ denotes a direct double bond or a =CH—CH= or =N—N= bridge, $E_3$ and $E_4$ independently of one another denote O, S, $NR_{51}$, $C(R_{51})(R_{52})$, C=O or $SO_2$, $E_5$ to $E_8$ independently of one another denote S, Se or $NR_{51}$, $R_{51}$, and $R_{52}$ independently of one another denote $C_1$ to $C_{12}$-alkyl, $C_2$ to $C_8$-alkenyl, $C_3$ to $C_7$-cycloalkyl, $C_7$ to $C_{15}$-aralkyl or $C_6$ to $C_{10}$-aryl, $R_{53}$ to $R_{60}$ independently of one another denote hydrogen, $C_1$– to $C_6$-alkyl, $C_1$ to $C_{18}$-alkoxy, cyano, $C_1$ to $C_{18}$-alkoxycarbonyl or $C_6$ to $C_{10}$-aryl, or $R_{53}$ and $R_{54}$ and $R_{59}$ and $R_{60}$ independently of one another together form a —$(CH_2)_3$—, —$(CH_2)_4$— or —CH=CH—CH=CH— bridge, v=0–10, wherein bonding to the bridge member Bridge$_1$ or Bridge$_2$ is effected by one of the radicals $R_{37}$ –$R_{54}$, or $R_{60}$ and the radicals mentioned then represent a direct bond, and Bridge$_1$ or Bridge$_2$ independently represents a bridge member of the formula —$(CH_2)_n$— or —$(Y_1)_s$ $(CH_2)_m$—$(Y_2)_o$—$(CH_2)_p$—$(Y_3)_q$—, each of which is optionally substituted by $C_1$ to $C_{18}$-alkoxy, halogen or phenyl, $Y_1$ to $Y_3$ independently of one another independently represent O, S, $NR_{61}$, COO, CONH, NHCONH, cyclopentanediyl, cyclohexanediyl, phenylene or naphthylene, beta-dicarbonyls, $R_{61}$ denotes $C_1$ to $C_6$-alkyl, $C_2$ to $C_6$-alkenyl, $C_4$ to $C_7$-cycloalkyl, $C_7$ to $C_{15}$-aralkyl or $C_6$- to $C_{10}$-aryl, n=0–12, m=0–8, p=0–12, o=0–6, q=0–1, and s=0–1.

9. The electrolyte solution of claim 1, wherein said bifunctional redox dye comprises a compound having the formula $$[Cat_1][M]$$

wherein M represents a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II);

wherein $Cat_1$ represents a ligand having the structural formula

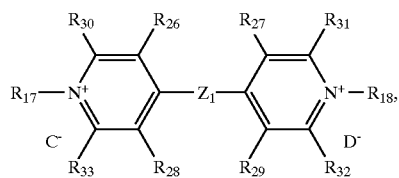

or having the structural formula

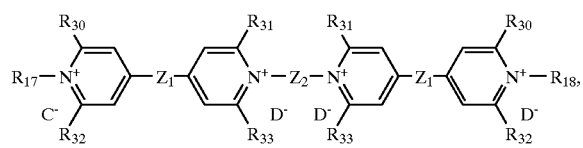

or having the structural formula

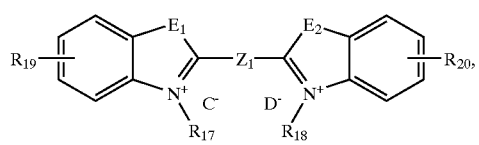

or having the structural formula

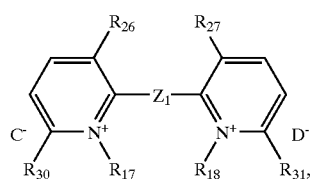

or having the structural formula

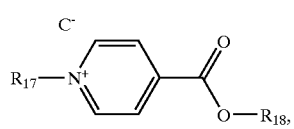

or having the structural formula

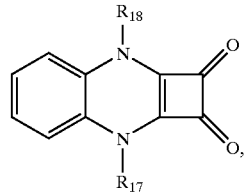

or having the structural formula

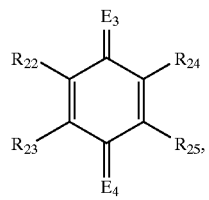

or having the structural formula

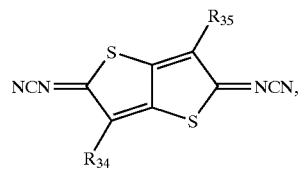

wherein $R_{17}$ and $R_{18}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl or $R_{17}$ and $R_{18}$ together form a —$(CH_2)_2$—, —$(CH_2)_3$—, or —CH=CH—, $R_{19}$, $R_{20}$ and $R_{22}$ to $R_{25}$ independently of one another denote hydrogen, $C_1$ to $C_{18}$-alkyl, $C_1$ to $C_{18}$-alkoxy, halogen, cyano, nitro or $C_1$ to $C_{18}$-alkoxycarbonyl or $R_{22}$ and $R_{23}$ and/or $R_{24}$ and $R_{25}$ form a —CH=CH—CH=CH— bridge; $R_{26}$, $R_{27}$, $R_{28}$ and $R_{29}$ independently of one another denote hydrogen or, in pairs, a —$(CH_2)_2$—, —$(CH_2)_3$— or —CH=CH— bridge, $E_3$ and $E_4$ independently of one another denote O, N—CN, $C(CN)_2$ or N—$C_6$- to $C_{10}$-aryl, $R_{34}$ and $R_{35}$ independently denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl, $R_{30}$ to $R_{33}$ independently of one another denote hydrogen or $C_1$–$C_6$ -alkyl, or $R_{30}$ and $R_{26}$ and/or $R_{31}$ and $R_{27}$ form a —CH=CH—CH=CH— bridge, $E_1$ and $E_2$ independently of one another denote O, S, $NR_{36}$ or $C(R_{36})_2$ or $E_1$ and $E_2$ together form a —N—$(CH_2)_2$—N— bridge, $R_{36}$ denotes $C_1$ to $C_{18}$-alkyl, $C_2$ to $C_{12}$-alkenyl, $C_4$ to $C_7$ -cycloalkyl, $C_7$ to $C_{15}$-aralkyl or $C_6$ to $C_{10}$-aryl, $Z_1$ denotes a direct bond, —CH=CH—, —C($CH_3$)=CH—, —C(CN)=CH—, —CCl=CCl—, —C(OH)=CH—, —CCl=CH—, —C≡C—, —CH=N—N=CH—, —C($CH_3$)=N—N=C($CH_3$)— or —CCl=N—N=CCl—, $Z_2$ denotes —$(CH_2)_r$— or —$CH_2$—$C_6H_4$—$CH_2$—, r=1–10, $C^-$ is selected from the group consisting of bis (trifluoromethylsulfonyl)imide (($CF_3SO_2$)$_2N^-$), bis (perfluoroethylsulfonyl)imide (($CF_3CF_2SO_2$)$_2N^-$) and tris (trifluoromethylsulfonyl)methide (($CF_3SO_2$)$_3C^-$), and $D^-$ is selected from the group consisting of halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis (trifluoromethylsulfonyl)imide (($CF_3SO_2$)$_2N^-$), bis (perfluoroethylsulfonyl)imide (($CF_3CF_2SO_2$)$_2N^-$) and tris (trifluoromethylsulfonyl)methide (($CF_3SO_2$)$_3C^-$).

10. The electrolyte solution claim 1, further comprising at least one additive selected from the group consisting of non-ionic cosolvents, polymers, thixotropic agents, and UV stabilizers.

11. An electro-optic device comprising at least one chamber and, as the electrolyte medium inside the chamber, an electrolyte solution having a Tg (glass transition temperature) of less than about −40° C. and comprising at least one bifunctional redox dye dissolved in an ionic liquid solvent.

12. The electro-optic device of claim 11, wherein said bifunctional redox dye comprises at least one redox active anodic moiety and at least one redox active cathodic moiety.

13. The electro-optic device of claim 12, wherein said anodic moiety of said bifunctional redox dye comprises a pyrazoline, metallocene, phenylenediamine, benzidine, phenoxadine, phenothiazine, tetrafulvalene or phenazine, and said cathodic moiety of said bifunctional redox dye comprises a viologen or anthraquinone.

14. The electro-optic device of claim 11, wherein said bifunctional redox dye comprises at least one energy receptor moiety and at least one redox active anodic moiety, at least one energy receptor moiety and at least one redox active cathodic moiety, or at least one energy receptor moiety and at least one redox active anodic moiety and at least one redox active cathodic moiety.

15. The electrolyte solution of claim 14, wherein said bifunctional redox dye comprises a redox active moiety comprising a pyrazoline, metallocene, phenylenediamine, benzidine, phenoxadine, phenothiazine, tetrafulvalene, phenazine, viologen or anthraquinone, and an energy receptor moiety comprising a benzophenone, benzotraizole, or cyanoacrylate.

16. The electro-optic device of claim 11, wherein said ionic liquid comprises at least one cation selected from the group consisting of lithium cation and quaternary ammonium cations, wherein said quaternary ammonium cations are selected from the group consisting of pyridinium, pyridazinium, pyrimidinium, pyrazinium, imidazolium, pyrazolium, thiazolium, oxazolium, triazolium, tetraalkylammonium, N-methyl morpholinium, cations of the formula $[(CH_3CH_2)_3N(R_1)]^+$, wherein $R_1$ is alkyl having 2–10 carbons, cations of the formula $[(CH_3)_2(CH_3CHCH_3)N(R_2)]^+$, wherein $R_2$ is alkyl having 2–10 carbons, cations having the structural formula

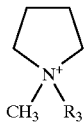

wherein $R_3$ is alkyl having 2–10 carbons, and cations having the structural formula

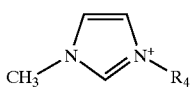

wherein $R_4$ is alkyl having 2–10 carbons.

17. The electro-optic device of claim 11, wherein said ionic liquid comprises at least one anion selected from the group consisting of trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

18. The electro-optic device of claim 11, wherein said bifunctional redox dye is a compound having the structural formula

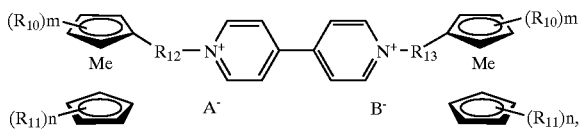

or having the structural formula

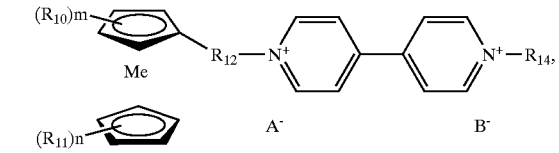

or having the structural formula

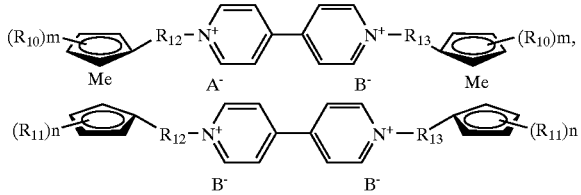

or having the structural formula

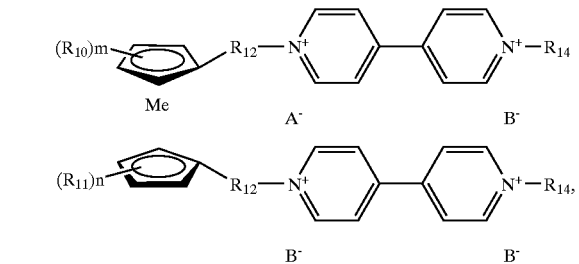

wherein $A^-$ is selected from the group consisting of trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$); $B^-$ is selected from the group consisting of a halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$); wherein $R_{10}$ and $R_{11}$ are each independently a hydrocarbon group selected from the group consisting of an alkyl, alkenyl and aryl group having 1 to 10 carbon atoms, in the case where $R_{10}$ or $R_{11}$ is an aryl group, the aryl group forms a condensed ring together with a cyclopentadienyl ring; wherein m=0–4; wherein n=0–4; wherein $R_{12}$ and $R_{13}$ are each independently a hydrocarbon residue having 1 to 20 carbon atoms, or alkylene groups having ester-bond unit, ether-bond unit, amide-bond unit, thioether-bond unit, amine-bond unit, urethane-bond unit, or silyl unit in the part of hydrocarbon groups, and $R_{14}$ is a hydrocarbon group selected from the group consisting of an alkyl, cycloalkyl, alkenyl, aryl, or aralkyl group having 1 to 20 carbon atoms, a heterocyclic group having 4 to 20 carbon atoms, and a substituted hydrocarbon or heterocyclic group obtained by substituting part of hydrogens of the hydrocarbon group or heterocyclic group with a substituent group; and Me represents Cr, Co, Fe, Mn, Ni, Os, Ru, V, Mo(X)(Q), Nb(X)(Q), Ti(X)(Q), V(X)(Q) or Zr(X)(Q) wherein X and Q are each independently selected from the group consisting of hydrogen, halogen, an alkyl group having 1 to 12 carbon atoms, $ClO_4^-$, $BF_4^-$, $PF_6^-$, $AsF_6^-$, $SbF_6^-$, $CH_3COO^-$, $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$);

or having the formula $Cat_1$-$An_1$, or having the formula $Cat_1$-$Bridge_1$-$An_1$, or having the formula $Cat_1$-$Bridge_1$-$An_1$-$Bridge_2$-$Cat_2$, or having the formula $An_2$-$Bridge_2$-$Cat_1$-$Bridge_1$-$An_1$, wherein $Cat_1$-$An_1$ represents a charge transfer complex; wherein $Cat_1$ and $Cat_2$ independently represent a radical having the structural formula

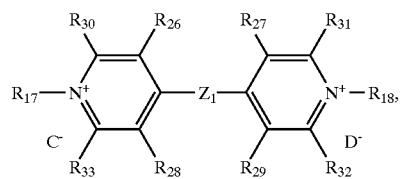

or having the structural formula

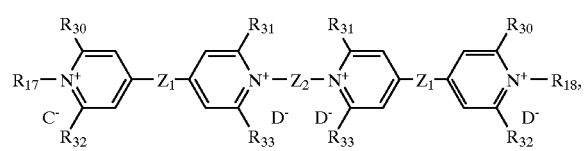

or having the structural formula

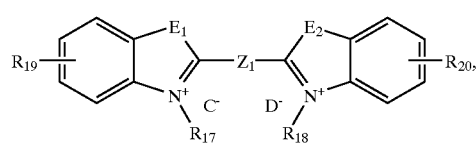

or having the structural formula

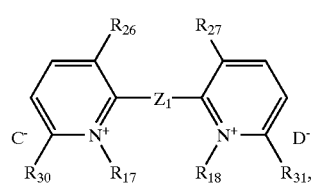

or having the structural formula

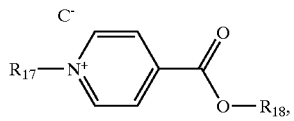

or having the structural formula

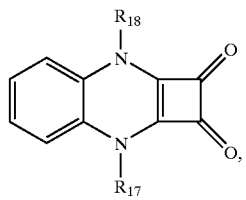

or having the structural formula

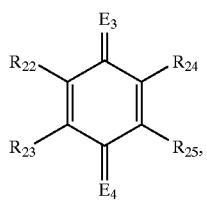

or having the structural formula

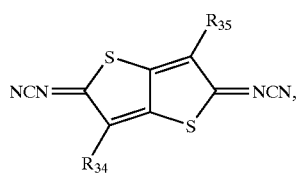

wherein $R_{17}$ and $R_{18}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl or $R_{17}$ and $R_{18}$ together form a —$(CH_2)_2$—, —$(CH_2)_3$—, or —CH=CH— bridge, $R_{19}$, $R_{20}$ and $R_{22}$ to $R_{25}$ independently of one another denote hydrogen, $C_1$ to $C_{18}$-alkyl, $C_1$ to $C_4$-alkoxy, halogen, cyano, nitro or $C_1$ to $C_{18}$-alkoxycarbonyl or $R_{22}$ and $R_{23}$ and/or $R_{24}$ and $R_{25}$ form a —CH=CH—CH=CH— bridge; $R_{26}$, $R_{27}$, $R_{28}$ and $R_{29}$ independently of one another denote hydrogen or, in pairs, a —$(CH_2)_2$—, —$(CH_2)_3$— or —CH=CH— bridge, $E_3$ and $E_4$ independently of one another denote O, N—CN, C(CN)$_2$ or N—$C_6$- to $C_{10}$-aryl, $R_{34}$ and $R_{35}$ independently denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl, $R_{30}$ to $R_{33}$ independently of one another denote hydrogen or $C_1$ to $C_6$-alkyl, or $R_{30}$ and $R_{26}$ and/or $R_{31}$ and $R_{27}$ form a —CH=CH—CH=CH— bridge, $E_1$ and $E_2$ independently of one another denote O, S, $NR_{36}$ or $C(R_{36})_2$ or $E_1$ and $E_2$ together form a —N—$(CH_2)_2$—N— bridge, $R_{36}$ denotes $C_1$ to $C_{18}$-alkyl, $C_2$ to $C_{12}$-alkenyl, $C_4$ to $C_7$-cycloalkyl, $C_7$ to $C_{15}$-aralkyl or $C_6$ to $C_{10}$-aryl, $Z_1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z_2$ denotes —$(CH_2)_r$— or —$CH_2$—$C_6H_4$—$CH_2$—, r=1–10, $C^-$ is selected from the group consisting of bis(trifluoromethylsulfonyl)imide (($CF_3SO_2)_2N^-$), bis (perfluoroethylsulfonyl)imide (($CF_3CF_2SO_2)_2N^-$) and tris (trifluoromethylsulfonyl)methide (($CF_3SO_2)_3C^-$), and $D^-$ is selected from the group consisting of halogen anion, $ClO_4^-$, $BF_4^-$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis (trifluoromethylsulfonyl)imide (($CF_3SO_2)_2N^-$), bis (perfluoroethylsulfonyl)imide (($CF_3CF_2SO_2)_2N^-$) and tris (trifluoromethylsulfonyl)methide (($CF_3SO_2)_3C^-$), wherein bonding to the bridge member bridge$_2$ or bridge$_2$ is effected via one of the radicals $R_{17}$–$R_{36}$, and the radicals mentioned then represent a direct bond, and wherein $An_1$ and $An_2$ independently represent radicals having the structural formula:

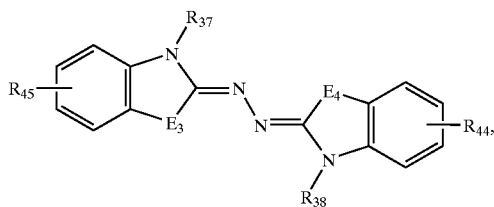

or having the structural formula

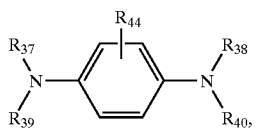

or having the structural formula

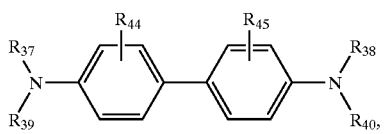

or having the structural formula

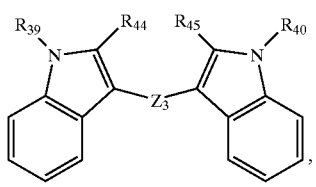

or having the structural formula

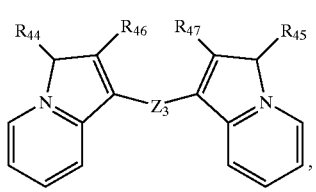

or having the structural formula

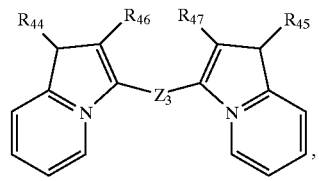

or having the structural formula

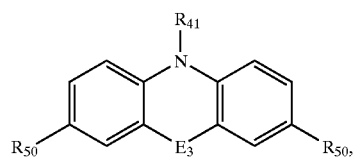

or having the structural formula

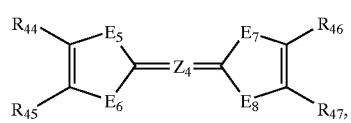

or having the structural formula

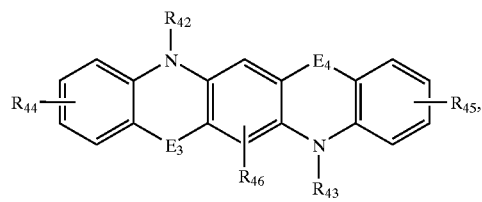

or having the structural formula

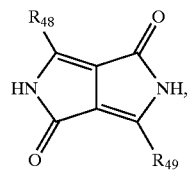

or having the structural formula

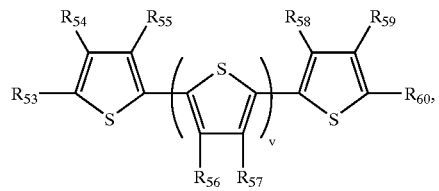

or wherein $An_1$ or $An_2$ independently represent a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II), wherein $R_{37}$ to $R_{43}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl, and $R_{41}$ to $R_{43}$ additionally denote hydrogen, $R_{44}$ to $R_{50}$ independently of one another denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl and $R_{48}$ and $R_{49}$ additionally denote an optionally benzo-fused aromatic or quasiaromatic five- or six-membered heterocyclic ring and $R_{50}$ additionally independently denotes $N(R_{51})(R_{52})$, $R_{44}$ and $R_{45}$ and/or $R_{46}$ and $R_{47}$ form a —$(CH_2)_3$—, —$(CH_2)_4$—, —$(CH_2)_5$— or —CH=CH—CH=CH— bridge, $Z_3$ denotes a direct bond or a —CH=CH— or —N=N— bridge, =$Z_4$=denotes a direct double bond or a =CH—CH= or =N—N=bridge, $E_3$ and $E_4$ independently of one another denote O, S, $NR_{51}$, $C(R_{51})(R_{52})$, C=O or $SO_2$, $E_5$ to $E_8$ independently of one another denote S, Se or $NR_{51}$, $R_{51}$ and $R_{52}$ independently of one another denote $C_1$ to $C_{12}$-alkyl, $C_2$ to $C_8$-alkenyl, $C_3$ to $C_7$-cycloalkyl, $C_7$ to $C_{15}$-aralkyl or $C_6$ to $C_{10}$-aryl, $R_{53}$ to $R_{60}$ independently of one another denote hydrogen, $C_1$– to $C_6$-alkyl, $C_1$ to $C_{18}$-alkoxy, cyano, $C_1$ to $C_{18}$-alkoxycarbonyl or $C_6$ to $C_{10}$-aryl, or $R_{53}$ and $R_{54}$ and $R_{59}$ and R60 independently of one another together form a —$(CH_2)_3$—, —$(CH_2)_4$— or —CH=CH—CH=CH— bridge, v=0–10, wherein bonding to the bridge member Bridge$_1$ or Bridge$_2$ is effected by one of the radicals $R_{37}$–$R_{54}$, or $R_{60}$ and the radicals mentioned then represent a direct bond, and Bridge$_1$ or Bridge$_2$ independently represents a bridge member of the formula —$(CH_2)_n$— or —$(Y_1)_s$ $(CH_2)_m$—$(Y_2)_o$—$(CH_2)_p$—$(Y_3)_q$—, each of which is optionally substituted by $C_1$ to $C_{18}$-alkoxy, halogen or phenyl, $Y_1$ to $Y_3$ independently of one another independently represent O, S, $NR_{61}$, COO, CONH, NHCONH, cyclopentanediyl, cyclohexanediyl, phenylene or naphthylene, beta-dicarbonyls, $R_{61}$ denotes $C_1$ to $C_6$-alkyl, $C_2$ to $C_6$-alkenyl, $C_4$ to $C_7$-cycloalkyl, $C_7$ to $C_{15}$-aralkyl or $C_6$– to $C_{10}$-aryl, n=0–12, m=0–8, p=0–12, o=0–6, q=0–1, and s=0–1.

19. The electrolyte solution claim 11, further comprising at least one additive selected from the group consisting of non-ionic cosolvents, polymers, thixotropic agents, and UV stabilizers.

20. The electrolyte solution of claim 11, wherein said bifunctional redox dye comprises a compound having the formula

[Cat$_1$][M]

wherein M represents a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II);

wherein Cat$_1$ represents a ligand having the structural formula

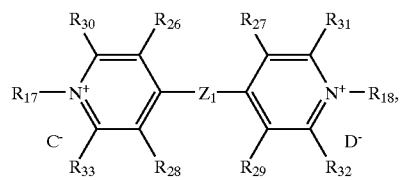

or having the structural formula

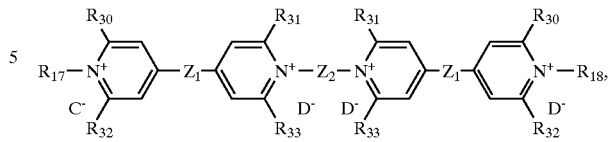

or having the structural formula

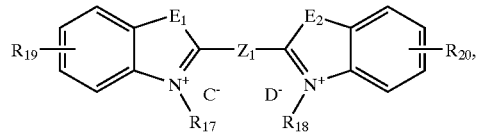

or having the structural formula

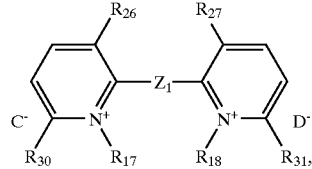

or having the structural formula

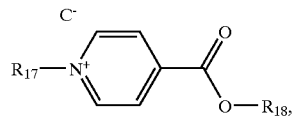

or having the structural formula

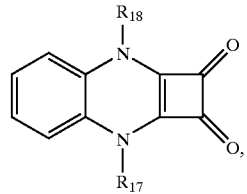

or having the structural formula

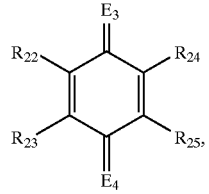

or having the structural formula

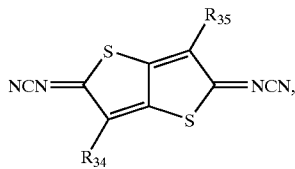

wherein R$_{17}$ and R$_{18}$ independently of one another denote C$_1$ to C$_{18}$-alkyl, C$_2$ to C$_{12}$-alkenyl, C$_3$ to C$_7$-cycloalkyl, C$_7$ to C$_{15}$-aralkyl or C$_6$ to C$_{10}$-aryl or R$_{17}$ and R$_{18}$ together form a —(CH$_2$)$_2$—, —(CH$_2$)$_3$—, or —CH=CH—, R$_{19}$, R$_{20}$ and R$_{22}$ to R$_{25}$ independently of one another denote hydrogen, C$_1$ to C$_{18}$-alkyl, C$_1$ to C$_{18}$-alkoxy, halogen, cyano, nitro or C$_1$ to C$_{18}$-alkoxycarbonyl or R$_{22}$ and R$_{23}$ and/or R$_{24}$ and R$_{25}$ form a —CH=CH—CH=CH— bridge; R$_{26}$, R$_{27}$, R$_{28}$ and R$_{29}$ independently of one another denote hydrogen or, in pairs, a —(CH$_2$)$_2$—, —(CH$_2$)$_3$— or —CH=CH— bridge, E$_3$ and E$_4$ independently of one another denote O, N—CN, C(CN)$_2$ or N—C$_6$— to C$_{10}$-aryl, R$_{34}$ and R$_{35}$ independently denote hydrogen, C$_1$ to C$_{18}$-alkyl, C$_1$ to C$_{18}$-alkoxy, halogen, cyano, nitro, C$_1$ to C$_{18}$-alkoxycarbonyl or C$_6$ to C$_{10}$-aryl, R$_{30}$ to R$_{33}$ independently of one another denote hydrogen or C$_1$–C$_6$-alkyl, or R$_{30}$ and R$_{26}$ and/or R$_{31}$ and R$_{27}$ form a —CH=CH—CH=CH— bridge, E$_1$ and E$_2$ independently of one another denote O, S, NR$_{36}$ or C(R$_{36}$)$_2$ or E$_1$ and E$_2$ together form a —N—(CH$_2$)$_2$—N— bridge, R$_{36}$ denotes C$_1$ to C$_{18}$-alkyl, C$_2$ to C$_{12}$-alkenyl, C$_4$ to C$_7$-cycloalkyl, C$_7$ to C$_{15}$-aralkyl or C$_6$ to C$_{10}$-aryl, Z$_1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, Z$_2$ denotes —(CH$_2$)$_r$— or —CH$_2$—C$_6$H$_4$—CH$_2$—, r=1–10, C$^-$ is selected from the group consisting of bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), and D$^-$ is selected from the group consisting of halogen anion, ClO$_4^-$, BF$_4^-$, PF$_6^-$, AsF$_6^-$, SbF$_6^-$, CH$_3$COO$^-$, and CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$).

21. A compound having the structural formula

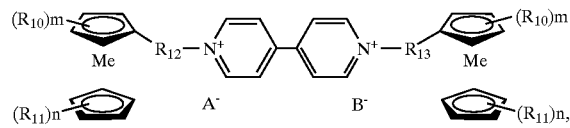

or having the structural formula

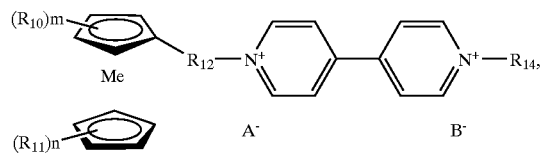

or having the structural formula

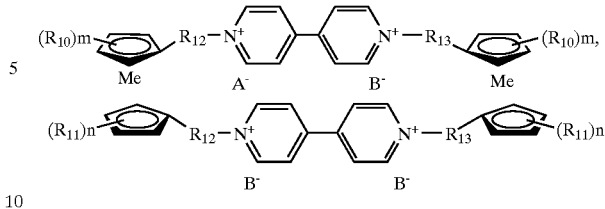

or having the structural formula

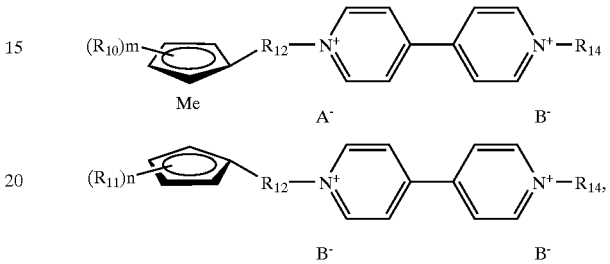

wherein A$^-$ is selected from the group consisting of trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$); B$^-$ is selected from the group consisting of a halogen anion, ClO$_4^-$, BF$_4^-$, PF$_6^-$, AsF$_6^-$, SbF$_6^-$, CH$_3$COO$^-$, and CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$); wherein R$_{10}$ and R$_{11}$ are each independently a hydrocarbon group selected from the group consisting of an alkyl, alkenyl and aryl group having 1 to 10 carbon atoms, in the case where R$_{10}$ or R$_{11}$ is an aryl group, the aryl group forms a condensed ring together with a cyclopentadienyl ring; wherein m=0–4; wherein n=0–4; wherein R$_{12}$ and R$_{13}$ are each independently a hydrocarbon residue having 1 to 20 carbon atoms, or alkylene groups having ester-bond unit, ether-bond unit, amide-bond unit, thioether-bond unit, amine-bond unit, urethane-bond unit, or silyl unit in the part of hydrocarbon groups, and R$_{14}$ is a hydrocarbon group selected from the group consisting of an alkyl, cycloalkyl, alkenyl, aryl, or aralkyl group having 1 to 20 carbon atoms, a heterocyclic group having 4 to 20 carbon atoms, and a substituted hydrocarbon or heterocyclic group obtained by substituting part of hydrogens of the hydrocarbon group or heterocyclic group with a substituent group; and Me represents Cr, Co, Fe, Mn, Ni, Os, Ru, V, Mo(X)(Q), Nb(X)(Q), Ti(X)(Q), V(X)(Q)or Zr(X)(Q) wherein X and Q are each independently selected from the group consisting of hydrogen, halogen, an alkyl group having 1 to 12 carbon atoms, ClO$_4^-$, BF$_4^-$, PF$_6^-$, AsF$_6^-$, SbF$_6^-$, CH$_3$COO$^-$, CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$);

or having the formula

Cat$_1$-An$_1$, or having the formula

Cat$_1$-Bridge$_1$-An$_1$, or having the formula

Cat$_1$-Bridge$_1$-An$_1$-Bridge$_2$-Cat$_2$, or having the formula

An$_2$-Bridge$_2$-Cat$_1$-Bridge$_1$-An$_1$, wherein Cat$_1$-An$_1$ represents a charge transfer complex;

wherein Cat$_1$ and Cat$_2$ independently represent a radical having the structural formula

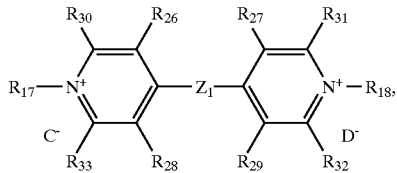

or having the structural formula

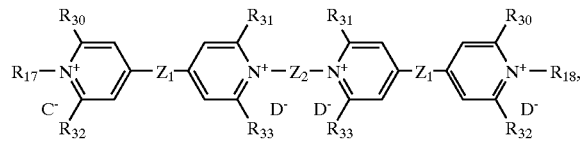

or having the structural formula

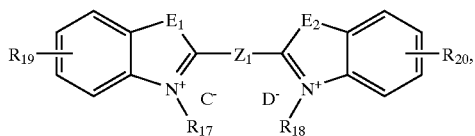

or having the structural formula

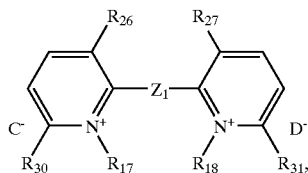

or having the structural formula

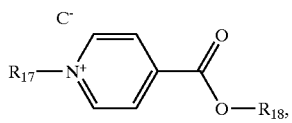

or having the structural formula

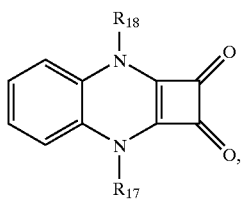

or having the structural formula

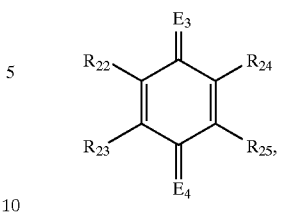

or having the structural formula

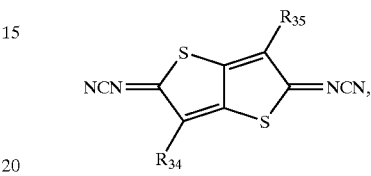

wherein $R_{17}$ and $R_{18}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl or $R_{17}$ and $R_{18}$ together form a —(CH$_2$)$_2$—, —(CH$_2$)$_3$—, or —CH=CH— bridge, $R_{19}$, $R_{20}$ and $R_{22}$ to $R_{25}$ independently of one another denote hydrogen, $C_1$ to $C_{18}$-alkyl, $C_1$ to $C_4$-alkoxy, halogen, cyano, nitro or $C_1$ to $C_{18}$-alkoxycarbonyl or $R_{22}$ and $R_{23}$ and/or $R_{24}$ and $R_{25}$ form a —CH=CH—CH=CH— bridge; $R_{26}$, $R_{27}$, $R_{28}$ and $R_{29}$ independently of one another denote hydrogen or, in pairs, a —(CH$_2$)$_2$—, —(CH$_2$)$_3$— or —CH=CH— bridge, $E_3$ and $E_4$ independently of one another denote O, N—CN, C(CN)$_2$ or N—C$_6$– to C$_{10}$-aryl, $R_{34}$ and $R_{35}$ independently denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl, $R_{30}$ to $R_{33}$ independently of one another denote hydrogen or $C_1$ to $C_6$-alkyl, or $R_{30}$ and $R_{26}$ and/or $R_{31}$ and $R_{27}$ form a —CH=CH—CH=CH— bridge, $E_1$ and $E_2$ independently of one another denote O, S, NR$_{36}$ or C(R$_{36}$)$_2$ or $E_1$ and $E_2$ together form a —N—(CH$_2$)$_2$—N— bridge, $R_{36}$ denotes $C_1$ to $C_{18}$-alkyl, $C_2$ to $C_{12}$-alkenyl, $C_4$ to $C_7$-cycloalkyl, $C_7$ to $C_{15}$-aralkyl or $C_6$ to $C_{10}$-aryl, $Z_1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z_2$ denotes —(CH$_2$)$_r$— or —CH$_2$—C$_6$H$_4$—CH$_2$—, r=1–10, C$^-$ is selected from the group consisting of bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), and D$^-$ is selected from the group consisting of halogen anion, ClO$_4^-$, BF$_4^-$, PF$_6^-$, AsF$_6^-$, SbF$_6^-$, CH$_3$COO$^-$, and CH$_3$(C$_6$H$_4$)SO$_3^-$, trifluoromethylsulfonate (CF$_3$SO$_3^-$), bis(trifluoromethylsulfonyl)imide ((CF$_3$SO$_2$)$_2$N$^-$), bis(perfluoroethylsulfonyl)imide ((CF$_3$CF$_2$SO$_2$)$_2$N$^-$) and tris(trifluoromethylsulfonyl)methide ((CF$_3$SO$_2$)$_3$C$^-$), wherein bonding to the bridge member bridge$_1$ or bridge$_2$ is effected via one of the radicals R$_{17}$–R$_{36}$, and the radicals mentioned then represent a direct bond, and wherein An$_1$ and An$_2$ independently represent radicals having the structural formula:

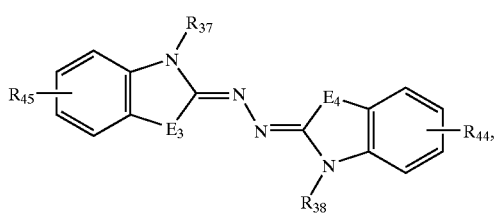

or having the structural formula

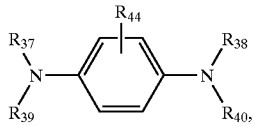

or having the structural formula

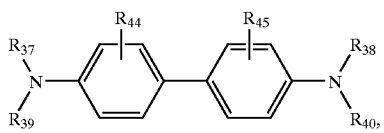

or having the structural formula

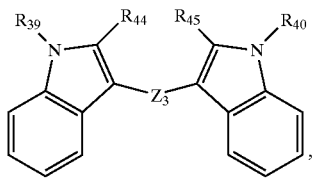

or having the structural formula

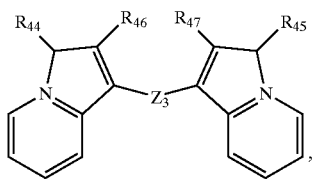

or having the structural formula

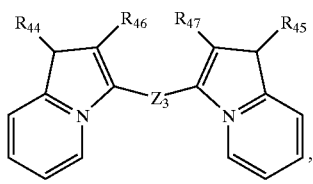

or having the structural formula

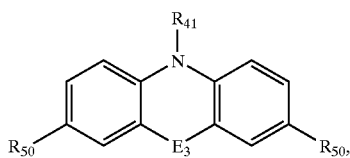

or having the structural formula

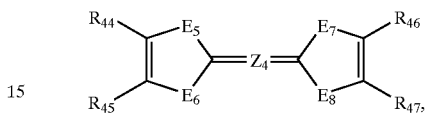

or having the structural formula

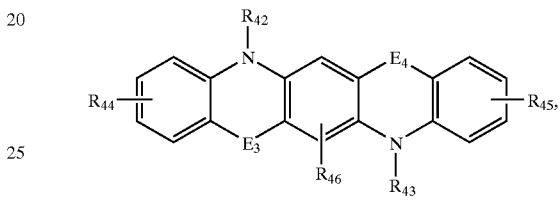

or having the structural formula

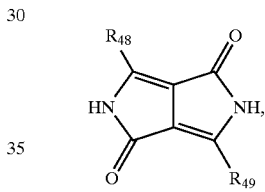

or having the structural formula

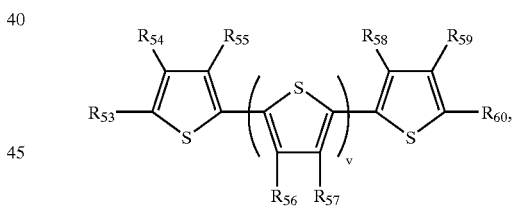

or wherein $An_1$ or $An_2$ independently represent a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II), wherein $R_{37}$ to $R_{43}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl, and $R_{41}$ to $R_{43}$ additionally denote hydrogen, $R_{44}$ to $R_{50}$ independently of one another denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl and $R_{48}$ and $R_{49}$ additionally denote an optionally benzo-fused aromatic or quasiaromatic five- or six-membered heterocyclic ring and $R_{50}$ additionally independently denotes $N(R_{51})(R_{52})$, $R_{44}$ and $R_{45}$ and/or $R_{46}$ and $R_{47}$ form a —$(CH_2)_3$—, —$(CH_2)_4$—, —$(CH_2)_5$— or —CH=CH—CH=CH— bridge, $Z_3$ denotes a direct bond or a —CH=CH— or —N=N— bridge, =$Z_4$=denotes a direct double bond or a =CH—CH= or =N—N= bridge, $E_3$ and $E_4$ independently of one another denote O, S, $NR_{51}$, $C(R_{51})(R_{52})$, C=O or $SO_2$, $E_5$ to $E_8$ independently of one another denote S, Se or $NR_{51}$, $R_{51}$ and $R_{52}$ independently of one another denote $C_1$ to $C_{12}$-alkyl, $C_2$ to $C_8$-alkenyl, $C_3$ to $C_7$-cycloalkyl, $C_7$ to $C_{15}$-aralkyl or $C_6$ to $C_{10}$-aryl, $R_{53}$ to R60 independently of one another denote hydrogen, $C_1$- to $C_6$-alkyl, $C_1$ to $C_{18}$-alkoxy, cyano, $C_1$ to $C_{18}$-alkoxycarbonyl or $C_6$ to $C_{10}$-aryl, or $R_{53}$ and $R_{54}$ and $R_{59}$ and R60 independently of one another together form a —$(CH_2)_3$—, —$(CH_2)_4$— or —CH=CH—CH=CH— bridge, v=0–10, wherein bonding to the bridge member Bridge$_1$ or Bridge$_2$ is effected by one of the radicals $R_{37}$–$R_{54}$, or $R_{60}$ and the radicals mentioned then represent a direct bond, and Bridge$_1$ or Bridge$_2$ independently represents a bridge member of the formula —$(CH_2)_n$— or —$(Y_1)_s(CH_2)_m$—$(Y_2)_o$—$(CH_2)_p$—$(Y_3)_q$—, each of which is optionally substituted by $C_1$ to $C_{18}$-alkoxy, halogen or phenyl, $Y_1$ to $Y_3$ independently of one another independently represent O, S, $NR_{61}$, COO, CONH, NHCONH, cyclopentanediyl, cyclohexanediyl, phenylene or naphthylene, beta-dicarbonyls, $R_{61}$ denotes $C_1$ to $C_6$-alkyl, $C_2$ to $C_6$-alkenyl, $C_4$ to $C_7$-cycloalkyl, $C_7$ to $C_{15}$-aralkyl or $C_6$– to $C_{10}$-aryl, n=0–12, m=0–8, p=0–12, o=0–6, q=0–1, and s=0–1.

22. A compound having the structure the formula, wherein said bifunctional redox dye comprises a compound having the formula

[Cat$_1$][M]

wherein M represents a metal salt comprising titanium (III), vanadium (III), vanadium (IV), iron (II), cobalt (II), copper (I), silver (I), indium (I), tin (II), antimony (III), bismuth (III), cerium (III), samarium (II), dysprosium (II), ytterbium (II), or europium (II);

wherein Cat$_1$ represents a ligand having the structural formula

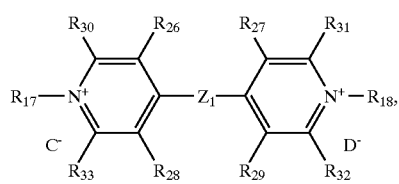

or having the structural formula

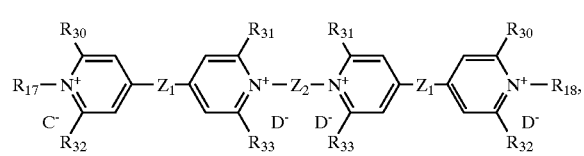

or having the structural formula

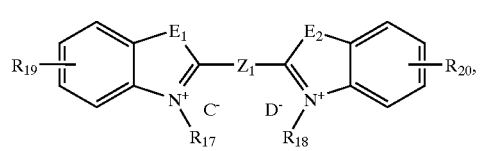

or having the structural formula

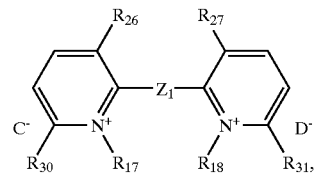

or having the structural formula

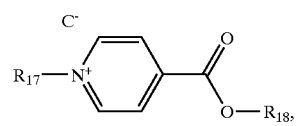

or having the structural formula

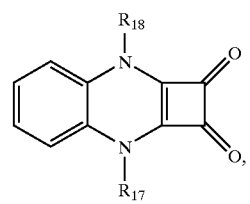

or having the structural formula

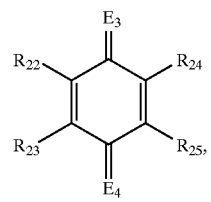

or having the structural formula

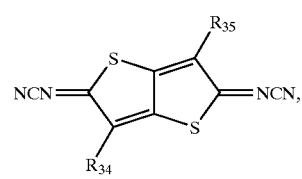

wherein $R_{17}$ and $R_{18}$ independently of one another denote $C_1$ to $C_{18}$-alkyl, $C_2$ to $C_{12}$-alkenyl, $C_3$ to $C_7$-cycloalkyl, $C_7$ to $C_{15}$-aralkyl or $C_6$ to $C_{10}$-aryl or $R_{17}$ and $R_{18}$ together form a —$(CH_2)_2$—, —$(CH_2)_3$—, or —CH=CH—, $R_{19}$, $R_{20}$ and $R_{22}$ to $R_{25}$ independently of one another denote hydrogen, $C_1$ to $C_{18}$-alkyl, $C_1$ to $C_{18}$-alkoxy, halogen, cyano, nitro or $C_1$ to $C_{18}$-alkoxycarbonyl or $R_{22}$ and $R_{23}$ and/or $R_{24}$ and $R_{25}$ form a —CH=CH—CH=CH— bridge; $R_{26}$, $R_{27}$, $R_{28}$ and $R_{29}$ independently of one another denote hydrogen or, in pairs, a —$(CH_2)_2$—, —$(CH_2)_3$— or —CH=CH— bridge, $E_3$ and $E_4$ independently of one another denote O, N—CN, C(CN)$_2$ or N—$C_6$– to $C_{10}$-aryl, $R_{34}$ and $R_{35}$ independently denote hydrogen, $C_1$ to $C_{18}$-alkyl, $C_1$ to $C_{18}$-alkoxy, halogen, cyano, nitro, $C_1$ to $C_{18}$-alkoxycarbonyl or $C_6$ to $C_{10}$-aryl, $R_{30}$ to $R_{33}$ independently of one another denote hydrogen or $C_1$–$C_6$-alkyl, or $R_{30}$ and $R_{26}$ and/or $R_{31}$ and $R_{27}$ form a —CH=CH—CH=CH— bridge, $E_1$ and $E_2$ independently of one another denote O, S, $NR_{36}$ or $C(R_{36})_2$ or $E_1$ and $E_2$ together form a —N—$(CH_2)_2$—N— bridge, $R_{36}$ denotes $C_1$ to $C_{18}$-alkyl, $C_2$ to $C_{12}$-alkenyl, $C_4$ to $C_7$-cycloalkyl, $C_7$ to $C_{15}$-aralkyl or $C_6$ to $C_{10}$-aryl, $Z_1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z_2$ denotes —$(CH_2)_r$— or —$CH_2$—$C_6H_4$—$CH_2$—, r=1–10, $C^-$ is selected from the group consisting of bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$), and $D^-$ is selected from the group consisting of halogen anion, $ClO_4^-$, $BF_4^{31}$, $PF_6^-$, $AsF_6^-$, $SbF_6^-$, $CH_3COO^-$, and $CH_3(C_6H_4)SO_3^-$, trifluoromethylsulfonate ($CF_3SO_3^-$), bis(trifluoromethylsulfonyl)imide (($CF_3SO_2)_2N^-$), bis(perfluoroethylsulfonyl)imide (($CF_3CF_2SO_2)_2N^-$) and tris(trifluoromethylsulfonyl)methide (($CF_3SO_2)_3C^-$).

23. A method for filling an empty electrooptic device with fluid comprising warm ionic liquid electrolyte solution, the device having relatively closely spaced plates, each plate having an inwardly facing conductive surface, the plates being sealed around their periphery by a seal that encloses an area of each plate, comprising:

(a) introducing a small opening into the seal of an empty device;

(b) placing the empty device into a chamber along with a container of fluid comprising ionic liquid electrolyte solution;

(c) evacuating the chamber;

(d) lowering the empty device into the fluid such that the opening in the seal is located under the surface of the fluid;

(e) warming at least a portion of the fluid to a temperature of at least 40° C.;

(f) exposing the fluid to a gas pressure greater than the pressure in the empty device to send the warm fluid into the device; and (g) sealing the gap in the peripheral seal of the device.

* * * * *

UNITED STATES PATENT AND TRADEMARK OFFICE
CERTIFICATE OF CORRECTION

PATENT NO.        : 6,853,472 B2
APPLICATION NO. : 10/600807
DATED             : January 18, 2005
INVENTOR(S)       : Harold H. Henry, III et al.

It is certified that error appears in the above-identified patent and that said Letters Patent is hereby corrected as shown below:

Col. 4 line 12 (Amend. dated 7/14/04, pg. 2, line 20), delete "seal"; and

Col. 4, line 18 (Amend. dated 7/14/04, pg. 3, line 2), "unnecessarily" should be -- unnecessary-- .

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 6,853,472 B2  
APPLICATION NO. : 10/600807  
DATED : February 8, 2005  
INVENTOR(S) : Benjamin P. Warner et al.

Page 1 of 1

It is certified that error appears in the above-identified patent and that said Letters Patent is hereby corrected as shown below:

This certificate supersedes Certificate of Correction issued May 29, 2007. The certificate should be vacated since no Certificate of Correction was granted for this patent number.

Signed and Sealed this

Nineteenth Day of June, 2007

JON W. DUDAS  
*Director of the United States Patent and Trademark Office*